US008633207B2

(12) United States Patent
Hadd et al.

(10) Patent No.: US 8,633,207 B2
(45) Date of Patent: Jan. 21, 2014

(54) QUINAZOLINE COMPOUNDS AND METHODS OF USE THEREOF

(75) Inventors: Michael J. Hadd, San Diego, CA (US); Mark W. Holladay, San Diego, CA (US); Martin Rowbottom, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 13/222,937

(22) Filed: Aug. 31, 2011

(65) Prior Publication Data

US 2012/0053174 A1    Mar. 1, 2012

Related U.S. Application Data

(60) Provisional application No. 61/379,309, filed on Sep. 1, 2010.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............ 514/266.1; 544/283; 544/284

(58) Field of Classification Search
USPC ................ 514/266.1; 544/283, 284
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,436,233 A | 7/1995 | Lee et al. | |
| 5,591,767 A | 1/1997 | Mohr et al. | |
| 5,612,059 A | 3/1997 | Cardinal et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,698,220 A | 12/1997 | Cardinal et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,798,119 A | 8/1998 | Herbig et al. | |
| 5,840,674 A | 11/1998 | Yatvin et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,972,366 A | 10/1999 | Haynes et al. | |
| 5,972,891 A | 10/1999 | Kamei et al. | |
| 5,980,945 A | 11/1999 | Ruiz | |
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,080,747 A | 6/2000 | Uckun et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,197,350 B1 | 3/2001 | Yamagata et al. | |
| 6,204,267 B1 | 3/2001 | Tang et al. | |
| 6,248,363 B1 | 6/2001 | Patel et al. | |
| 6,253,872 B1 | 7/2001 | Neumann | |
| 6,264,970 B1 | 7/2001 | Hata et al. | |
| 6,267,981 B1 | 7/2001 | Okamoto et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,350,458 B1 | 2/2002 | Modi | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |

(Continued)

FOREIGN PATENT DOCUMENTS

| | | |
|---|---|---|
| CN | 101463014 | 6/2009 |
| EP | 0579496 | 11/2001 |

(Continued)

OTHER PUBLICATIONS

Vippagunta et al (2000).*
Burger et al (1995).*
Wolff et al (1995).*
Barton et al., Mol. Canc. Ther. (2004) 3(1):11-20.
Baxter et al., Lancet (2005) 365:1054-1061.
Bedingdield et al., British Journal of Pharmacology (1995) 116:3323-3329.
Blume-Jensen et al., Nature (2001) 411(6835):355-365.
Borie et al., Transplantation (2005) 79(7):791-801.
Bousquet et al., Oncogene (2005) 24:7248-7252.
Bromberg, J Clin Invest. (2002) 109(9):1139-1142.
Campbell et al., Blood (2006) 107(5):2098-2100.

(Continued)

*Primary Examiner* — Paul V. Ward
(74) *Attorney, Agent, or Firm* — Jones Day

(57) ABSTRACT

Provided herein are quinazoline compounds for treatment of JAK kinase mediated diseases, including JAK2 kinase-, JAK3 kinase- or TYK2 kinase-mediated diseases. Also provided are pharmaceutical compositions comprising the compounds and methods of using the compounds and compositions.

18 Claims, No Drawings

(56) References Cited

U.S. PATENT DOCUMENTS

| | | | |
|---|---|---|---|
| 6,653,301 | B2 | 11/2003 | Bebbington et al. |
| 6,656,939 | B2 | 12/2003 | Bebbington et al. |
| 6,699,500 | B2 | 3/2004 | Okada et al. |
| 6,727,251 | B2 | 4/2004 | Bebbington et al. |
| 6,740,634 | B1 | 5/2004 | Saikawa et al. |
| 6,989,385 | B2 | 1/2006 | Bebbington et al. |
| 7,008,948 | B2 | 3/2006 | Bebbington et al. |
| 7,087,603 | B2 | 8/2006 | Bebbington et al. |
| 7,390,815 | B2 | 6/2008 | Bebbington et al. |
| 7,427,681 | B2 | 9/2008 | Bebbington et al. |
| 7,432,275 | B2 | 10/2008 | Bakthavatchalam et al. |
| 7,625,913 | B2 | 12/2009 | Bebbington et al. |
| 2003/0105090 | A1 | 6/2003 | Bebbington et al. |
| 2004/0157893 | A1 | 8/2004 | Bebbington et al. |
| 2005/0038023 | A1 | 2/2005 | Bebbington et al. |
| 2006/0194805 | A1 | 8/2006 | Bakthavatchalam et al. |
| 2008/0312258 | A1 | 12/2008 | Rodgers et al. |
| 2008/0312259 | A1 | 12/2008 | Rodgers et al. |
| 2010/0317659 | A1 | 12/2010 | Abraham et al. |
| 2012/0053176 | A1 | 3/2012 | Armstrong et al. |

FOREIGN PATENT DOCUMENTS

| | | |
|---|---|---|
| EP | 0944616 | 6/2003 |
| WO | WO 02/17918 | 3/2002 |
| WO | WO 02/50065 | 6/2002 |
| WO | WO 02/057259 | 7/2002 |
| WO | WO 02/059111 | 8/2002 |
| WO | WO 02/062789 | 8/2002 |
| WO | WO 02/066461 | 8/2002 |
| WO | WO 02/068415 | 9/2002 |
| WO | WO 03/062209 | 7/2003 |
| WO | WO 2004/015142 | 2/2004 |
| WO | WO 2004/020441 | 3/2004 |
| WO | WO 2004037814 | 5/2004 |
| WO | WO 2004/054582 | 7/2004 |
| WO | WO 2004/055003 | 7/2004 |
| WO | WO 2004/080463 | 9/2004 |
| WO | WO 2006/067614 | 6/2006 |
| WO | WO 2008/005310 | 1/2008 |
| WO | WO 2008116139 | 9/2008 |
| WO | WO 2010/038060 | 4/2010 |
| WO | WO 2010/099379 | 9/2010 |
| WO | WO 2012/030894 | 3/2012 |
| WO | WO 2012/030910 | 3/2012 |
| WO | WO 2012/030912 | 3/2012 |
| WO | WO 2012/030914 | 3/2012 |
| WO | WO 2012/030924 | 3/2012 |
| WO | WO 2012/030944 | 3/2012 |

OTHER PUBLICATIONS

Erba et al., (1997) J. Chem. Soc., Perkin Trans. 1:3021-3024.
Fabian et al., Nature Biotechnology (2005) 23(3):329-336.
Gatley et. al., J. Nucl. Med. (1986) 27:388.
Glossary of Terms Used in Medicinal Chemistry (IUPAC Recommendations 1998).
Gordon et. al., Drug Metab. Dispos. (1987) 15:589.
Griesinger F. et al., Genes Chromosomes Cancer (2005) 44:329-333.
Jones et al., Blood (2005) 106(6):2162-2168.
Lacronique et al., Blood (2000) 95(6):2076-2083.
Lacronique et al., Science (1997) 278:1309-1312.
Levine et al., Blood (2006) 107(10):4139-4141.
Lijinsky et. al., Food Cosmet. Toxicol. (1982) 20:393.
Lijinsky et. al., J. Nat. Cancer Inst. (1982) 69:1127.
Mangold et. al., Mutation Res. (1994) 308:33.
Mercher et al., Blood (2006) 108(8):2770-2779.
Middleton et al., J. Org. Chem. (1980) 45(14):2883-2887.
Milici et al., Arthritis Research (2008) 10(R14):1-9.
Pakrashi, J. Org. Chem (1971) 36(5):642-645.
Pardanani et al., Leukemia (2007) 21:1658-1668.
Pardanani, A. Leukemia (2008) 22:23-30.
Rane, S.G. and Reddy E.P., Oncogene (2000) 19:5662-5679.
Samanta et al., Cancer Res (2006) 66(13):6468-6472.
Santus and Baker, J. Controlled Release (1995) 35:1-21.
Sawyers et al., Cell, (1992) 70:901-910.
Schwaller et al., Mol. Cell. (2000) 6:693-704.
Scott et al., N Eng J Med 2007 356(5):459-468.
Still et al. J. Org. Chem. (1978) 43(14):2923-2925.
Tang, JACS Communications (2002) 124(12):2870-2871.
Tefferi N. ,Eng. J. Med. (2007) 356(5):444-445.
Verma et al., Drug Development and Industrial Pharmacy (2000) 26:695-708.
Verma et al., J. Controlled Release (2002) 79:7-27.
Wade D, Chem. Biol. Interact. (1999) 117:191.
Wright et al., Bioorganic & Medicinal Chem Lett. (2001) 11:17-21.
Wright et al., J. Med. Chem. (2002) 45:3865-3877.
Zello et. al., Metabolism (1994) 43:487.
Zhao et al., EMBO (2002) 21(9):2159-2167.

* cited by examiner

QUINAZOLINE COMPOUNDS AND METHODS OF USE THEREOF

CROSS REFERENCE TO RELATED APPLICATIONS

This application claims the benefit of the priority of U.S. Provisional Application No. 61/379,309, filed Sep. 1, 2010, the disclosure of which is incorporated herein by reference in its entirety.

FIELD

Provided herein are compounds that are modulators of JAK kinases, compositions comprising the compounds and methods of use thereof. The compounds provided are useful in the treatment, prevention, or amelioration of a disease or disorder related to JAK, including JAK2, JAK3 or TYK2 kinases, or one or more symptoms associated with such diseases or disorders. Further provided are methods for treatment of cancer, including blood borne and solid tumors.

BACKGROUND

The JAK kinase family is a cytoplasmic protein kinase family comprising the members JAK1, JAK2, JAK3 and TYK2. Growth factor or cytokine receptors that recruit JAK kinases include the interferon receptors, interleukin receptors (receptors for the cytokines IL-2 to IL-7, IL-9 to IL-13, IL-15, IL-23), various hormone receptors (erythropoietin (Epo) receptor, the thrombopoietin (Tpo) receptor, the leptin receptor, the insulin receptor, the prolactin (PRL) receptor, the Granulocyte Colony-Stimulating Factor (G-CSF) receptor and the growth hormone receptor, receptor protein tyrosine kinases (such as EGFR and PDGFR), and receptors for other growth factors such as leukemia inhibitory factor (LIF), Oncostatin M (OSM), IFNα/β/γ, Granulocyte-macrophage colony-stimulating factor (GM-CSF), Ciliary neurotrophic factor (CNTF), cardiotrophin-1 (CT-1) (See, Rane, S. G. and Reddy E. P., *Oncogene* 2000 19, 5662-5679).

Phosphorylated receptors serve as docking sites for other SH-2 domain containing signaling molecules that interact with JAKs such as the STAT family of transcription factors, Src family of kinases, MAP kinases, PI3 kinase and protein tyrosine phosphatases (Rane S. G. and Reddy E. P., *Oncogene* 2000 19, 5662-5679). The family of latent cytoplasmic transcription factors, STATs, is the most well characterized downstream substrates for JAKs. The STAT proteins bind to phosphorylated cytokine receptors through their SH2 domains to become phosphorylated by JAKs, which leads to their dimerization and release and eventual translocation to the nucleus where they activate gene transcription. The various members of STAT which have been identified thus far, are STAT1, STAT2, STAT3, STAT4, STATS (including STAT5a and STAT5b) and STATE.

Since the JAK kinases may play an important signaling role via such receptors, disorders of fat metabolism, growth disorders and disorders of the immune system are all potential therapeutic targets.

The JAK kinases and JAK2 mutations are implicated in myeloproliferative disorders, cancers, including blood borne and solid tumors. Exemplary disorders include chronic myeloid leukemia (CML), polycythemia vera (PV), essential thrombocythemia (ET), primary myelofibrosis (PMF), chronic eosinophilic leukemia (CEL), chronic myelomonocytic leukemia (CMML) and systemic mastocytosis (SM). Myeloproliferative disorders are believed to arise from either gain-of-function mutations to JAK itself or from activation by the oncoprotein BCR-ABL, which specifically activates the JAK2 pathway. Several literature reports describe role of JAK2 mutations in various disorders. See, Samanta et al. *Cancer Res* 2006, 66(13), 6468-6472, Sawyers et al. *Cell,* 1992, 70, 901-910, Tefferi *N. Eng. J. Med.* (2007) 356(5): 444-445) Baxter et al. *Lancet* (2005) 365:1054-1056, Levine et al. *Blood* (2006, Jones et al. *Blood* (2005) 106:2162-2168) 107:4139-4141, Campbell et al. *Blood* (2006) 107(5): 2098-2100, Scott et al. *N Eng J Med* 2007 356(5): 459-468, Mercher et al. *Blood* (2006) 108(8): 2770-2778, Lacronique et al. *Science* (1997) 278:1309-1312, Lacronique et al. *Blood* (2000) 95:2535-2540, Griesinger F. et al. *Genes Chromosomes Cancer* (2005) 44:329-333, Bousquet et al. *Oncogene* (2005) 24:7248-7252, Schwaller et al. *Mol. Cell.* 2000 6,693-704, Zhaoi et al. *EMBO* 2002 21(9), 2159-2167.

Literature indicates that JAK may also serve as a target for prostate cancer, including androgen-resistant prostate cancer. See, Barton et al. *Mol. Canc. Ther.* 2004 3(1), 11-20, Blume-Jensen et al. *Nature* (2001) 411(6835):355-356 and Bromberg *J Clin Invest.* (2002) 109(9):1139-1142, Rane *Oncogene* (2000) 19(49):5662-5679. JAK as a prominent mediator of the cytokine signaling pathway, is considered to be a therapeutic target for inflammation and transplant rejections. See, Borie et al., *Transplantation* (2005) 79(7):791-801 and Milici et al., *Arthritis Research* (2008) 10(R14):1-9

Given the multitude of diseases attributed to the dysregulation of JAK signaling, many small molecule inhibitors of JAK are currently being developed. Examples of compounds in preclinical development include TG101209 (TargeGen). Examples of compounds being investigated in clinical studies include INCB018424 (Incyte), XL019 (Exelixis) and TG101348 (TargeGen). See, Pardanani et al. *Leukemia* 2007, 21:1658-1668; and Pardanai, A. *Leukemia* 2008 22:23-20.

There is, however, an ever-existing need to provide novel classes of compounds that are useful as inhibitors of enzymes in the JAK signaling pathway.

SUMMARY

Provided herein are compounds of formula (I)

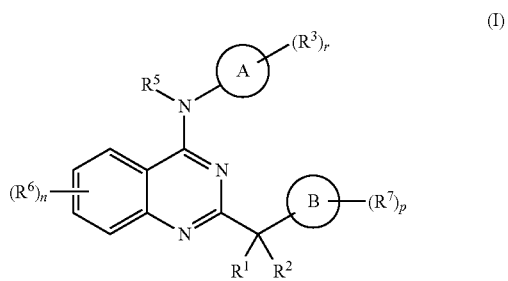

or pharmaceutically acceptable salts, solvates or hydrates thereof, wherein

A is azolyl;

B is 6-membered nitrogen containing heteroaryl;

$R^1$ and $R^2$ are selected from (i), (ii), (iii), (iv), and (v) as follows:

(i) $R^1$ and $R^2$ together form =O, =S, =NR$^9$ or =CR$^{10}$R$^{11}$;

(ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substitutents selected from halo, deutero, alkyl, cycloalkyl, heterocyclyl, aryl, heteroaryl, cyano, =O, =N—$OR^{21}$, —$R^xOR^{21}$, —$R^xN(R^{22})_2$, —$R^xS(O)_qR^{23}$, —$C(O)R^{21}$, —$C(O)OR^{21}$ and —$C(O)N(R^{22})_2$ and wherein the heterocyclyl contains one to two heteroatoms selected from O, $NR^{24}$, S, S(O) and $S(O)_2$;

(iii) $R^1$ is hydrogen or halo; and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —$C(O)OR^w$; and $R^2$ is hydrogen, halo or —$OR^8$; and (v) $R^1$ is halo, deutero, —$OR^{12}$; —$NR^{13}R^{14}$, or —$S(O)_qR^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substituents selected from halo, cyano, alkyl, —$R^xOR^w$, —$R^xS(O)_qR^v$ and —$R^xNR^yR^z$;

each $R^3$ is independently hydrogen, deutero, halo, alkyl, cyano, haloalkyl, deuteroalkyl, cycloalkyl, cycloalkylalkyl, hydroxy or alkoxy;

$R^5$ is hydrogen or alkyl;

each $R^6$ is independently selected from deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —$R^xOR^{18}$, —$R^xNR^{19}R^{20}$, —$R^xC(O)NR^yR^z$, —$R^xS(O)_qR^v$, —$R^xNR^{19}C(O)R^{18}$, —$R^xC(O)OR^{18}$ and —$R^xNR^{19}S(O)_qR^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:

(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^v$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —$C(O)NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:

(i) $R^y$ and $R^z$ are each independently hydrogen, alkyl, alkenyl, alkynyl, cycloalkyl, haloalkyl or heterocyclyl;

(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;

r is 1-3;

p is 0-4; and each q is independently 0, 1 or 2.

In certain embodiments, the compounds have activity as JAK kinase, including JAK2 kinase, modulators. The compounds are useful in medical treatments, pharmaceutical compositions and methods for modulating the activity of JAK kinase, including wildtype and/or mutated forms of JAK kinase. In certain embodiments, the compounds provided herein have activity as JAK2 kinase modulators. In certain embodiments, the compounds are inhibitors of JAK kinase, including JAK2 kinase.

In one embodiment, the compounds for use in the compositions and methods provided herein are compounds of formula (I).

In one embodiment, the compound provided herein is a compound of formula (I). In one embodiment, the compound provided herein is a pharmaceutically acceptable salt of the compound of formula (I). In one embodiment, the compound provided herein is a solvate of the compound of formula (I). In one embodiment, the compound provided herein is a hydrate of compound of formula (I).

Also provided are pharmaceutical compositions formulated for administration by an appropriate route and means containing effective concentrations of one or more of the compounds provided herein, or pharmaceutically acceptable salts, solvates and hydrates thereof, and optionally comprising at least one pharmaceutical carrier.

Such pharmaceutical compositions deliver amounts effective for the treatment, prevention, or amelioration of diseases or disorders that include without limitation, myeloproliferative disorders such as polycythemia vera (PCV), essential thrombocythemia (ET), primary myelofibrosis (PMF), chronic eosinophilic leukemia (CEL), chronic myelomonocytic leukemia (CMML), systemic mastocytosis (SM) and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer such as cancer of the head and neck, prostate cancer, breast cancer, ovarian cancer, melanoma, lung cancers, brain tumors, pancreatic cancer and renal cancer; and inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma chronic obstructive pulmonary disease (COPD) and dry eye syndrome (or keratoconjunctivitis sicca (KCS)). In one embodiment, such diseases or disorders are modulated or otherwise affected by the JAK kinases, including JAK2, JAK3 or TYK2.

In certain embodiments, the compounds provided herein are modulators of the activity of an adenosine $A_3$ receptor. In certain embodiments, the compounds provided herein are useful in preventing, treating, or ameliorating one or more symptoms of an adenosine $A_3$-mediated condition, disorder, or disease. In certain embodiments, the compounds provided herein are useful in preventing, treating, or ameliorating one or more symptoms of glaucoma or ocular hypertension.

In certain embodiments, provided herein is a method of modulating the activity of an adenosine $A_3$ receptor, comprising contacting the adenosine $A_3$ receptor with an effective amount of a compound of formula I, or a pharmaceutically acceptable salt, solvate, or prodrug thereof.

In certain embodiments, provided herein is a method of down regulating the activity of an adenosine $A_3$ receptor, comprising contacting the adenosine $A_3$ receptor with an effective amount of a compound of formula I, or a pharmaceutically acceptable salt, solvate, or prodrug thereof.

Also provided herein are combination therapies using one or more compounds or compositions provided herein, or pharmaceutically acceptable salts, solvates or hydrates thereof, in combination with other pharmaceutically active agents for the treatment of the diseases and disorders described herein.

In one embodiment, such additional pharmaceutical agents include one or more chemotherapeutic agents, anti-proliferative agents, anti-inflammatory agents, immunomodulatory agents or immunosuppressive agents.

The compounds or compositions provided herein, or pharmaceutically acceptable salts, solvates or hydrates thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by JAK kinases, including JAK2 kinase such as wild type and/or mutant JAK2 kinase, or one or more symptoms or causes thereof. In another embodiment, provided herein are methods of treating, preventing or ameliorating a disease or disorder by modulating the JAK2 kinase selectively over JAK3 kinase. In yet another embodiment, provided herein are methods of treating, preventing or ameliorating a disease or disorder by modulating the JAK3 kinase selectively over JAK2 kinase. In another embodiment, provided herein are methods of treating, preventing or ameliorating a disease or disorder by modulating both JAK2 and JAK3. In one embodiment, provided are methods for treatment of cancer, including blood borne and solid tumors.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

These and other aspects of the subject matter described herein will become evident upon reference to the following detailed description.

DETAILED DESCRIPTION

Provided herein are compounds of formula (I) that have activity as JAK kinase, including JAK2 kinase, modulators. Further provided are methods of treating, preventing or ameliorating diseases that are modulated by JAK kinases, including JAK2 kinase, and pharmaceutical compositions and dosage forms useful for such methods. The methods and compositions are described in detail in the sections below.

In certain embodiments, the compounds provided herein are JAK2 selective, i.e., the compounds bind or interact with JAK2 at substantially lower concentrations than they bind or interact with other JAK receptors, including JAK3 receptor, at that same concentration. In certain embodiments, the compounds bind to JAK3 receptor at a binding constant at least about 3-fold higher, about 5-fold higher, about 10-fold higher, about 20-fold higher, about 25-fold higher, about 50-fold higher, about 75-fold higher, about 100-fold higher, about 200-fold higher, about 225-fold higher, about 250 fold higher, or about 300 fold higher than they bind JAK2 receptor.

In certain embodiments, the compounds provided herein are JAK3 selective, i.e., the compounds bind or interact with JAK3 at substantially lower concentrations than they bind or interact with other JAK receptors, including JAK2 receptor, at that same concentration. In certain embodiments, the compounds bind to JAK2 receptor at a binding constant at least about 3-fold higher, about 5-fold higher, about 10-fold higher, about 20-fold higher, about 25-fold higher, about 50-fold higher, about 75-fold higher, about 100-fold higher, about 200-fold higher, about 225-fold higher, about 250 fold higher, or about 300 fold higher than they bind with JAK3 receptor.

In certain embodiments, the compounds provided herein have Kd of greater than about 10 nM, 20 nM, 25 nM, 40 nM, 50 nM, or 70 nM against Aurora B kinase. Methods for determining binding constant against Aurora B kinase are known to one of skill in the art. Exemplary methods are described in U.S. provisional application No. 61/294,413, International Publication No. WO 2011/088045 and Fabian et al., *Nature Biotechnology* 2005, 23, 329-336.

A. DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain group consisting solely of carbon and hydrogen atoms, containing at least one double bond, in certain embodiment, having from 2 to 10 carbon atoms, from 2 to 8 carbon atoms, or from 2 to 6 carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain group consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkoxy" refers to the group having the formula —OR wherein R is alkyl or haloalkyl, where the alkyl may be optionally substituted by one or more substituents, in one embodiment, one, two or three substitutents independently selected from the group consisting of nitro, halo, hydroxyl, alkoxy, oxo, thioxo, amino, carbony, carboxy, azido, cyano, cycloalkyl, heteroaryl, and heterocyclyl.

"Alkoxyalkyl" refers to a group having the formula —$R_h$OR wherein $R_h$ is a straight or branched alkylene chain and OR is alkoxy as defined above.

"Alkylthio" refers to a group having the formula —SR wherein R is alkyl or haloalkyl.

"aryloxy" refers to the group —OR, in which R is aryl, including lower aryl, such as phenyl.

"Amine" or "amino" refers to a group having the formula —NR'R" wherein R' and R" are each independently hydrogen, alkyl, haloalkyl, hydroxyalkyl or alkoxyalkyl or wherein R' and R", together with the nitrogen atom to which they are attached form a heterocyclyl optionally substituted with halo, oxo, hydroxy or alkoxy.

"Aminoalkyl" refers to a group having the formula —$R_h$NR'R" wherein $R_h$ is a straight or branched alkylene chain and wherein NR'R$^{11}$ is amino as defined above.

"Aminocarbonyl" refers to a group having the formula —C(O)NR'R" wherein —NR'R" is amino as defined above.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene. The term includes both substituted and unsubstituted moieties. The aryl group can be substituted with any described moiety, including, but not limited to, one or more moieties selected from the group consisting of halo (fluoro, chloro, bromo or iodo), alkyl, hydroxyl, amino, alkoxy, aryloxy, nitro and cyano.

"Cycloalkyl" refers to a stable monovalent monocyclic or bicyclic hydrocarbon group consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a group of the formula —$R_aR_d$ where $R_a$ is an alkyl group as defined above and $R_d$ is a cycloalkyl group as defined above. The alkyl group and the cylcoalkyl group may be optionally substituted as defined herein.

"Deutero" or "deuterium" refers to the hydrogen isotope deuterium having the chemical symbol D.

"Deuteroalkyl" refers to an isotopically enriched alkyl group in which one or more of the hydrogen atoms are replaced by deuterium.

"Halo", "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl, 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

"Heterocyclyl" refers to a stable 3- to 15-membered ring group which consists of carbon atoms and from one to five heteroatoms selected from a group consisting of nitrogen, oxygen and sulfur. In one embodiment, the heterocyclic ring system group may be a monocyclic, bicyclic or tricyclic ring or tetracyclic ring system, which may include fused or bridged ring systems; and the nitrogen or sulfur atoms in the heterocyclic ring system group may be optionally oxidized; the nitrogen atom may be optionally quaternized; and the heterocyclyl group may be partially or fully saturated or aromatic. The heterocyclic ring system may be attached to the main structure at any heteroatom or carbon atom which results in the creation of a stable compound. Exemplary heterocylic radicals include, azetidinyl, benzopyranonyl, benzopyranyl, benzotetrahydrofuranyl, benzotetrahydrothienyl, chromanyl, chromonyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4 dithianyl, isobenzotetrahydrofuranyl, isobenzotetrahydrothienyl, isochromanyl, isocoumarinyl, benzo[1,3]dioxol-5-yl, benzodioxolyl, 1,3-dioxolan-2-yl, dioxolanyl, morpholinyl, octahydroindolyl, octahydroisoindolyl, tetrahydrofuran, oxazolidin-2-onyl, oxazolidinonyl, piperidinyl, piperazinyl, pyranyl, tetrahydrofuryl, tetrahydrofuranyl, tetrahydroisoquinolinyl, tetrahydropyranyl, tetrahydrothienyl, pyrrolidinonyl, oxathiolanyl, and pyrrolidinyl.

"Heteroaryl" refers to a heterocyclyl group as defined above which is aromatic. The heteroaryl group may be attached to the main structure at any heteroatom or carbon atom which results in the creation of a stable compound. Examples of such heteroaryl groups include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, isoxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thienyl, triazinyl and triazolyl.

"Azolyl" refers to a 5-membered heterocyclic or heteroaryl ring system containing at least one nitrogen atom. Exemplary azolyl rings include pyrazolyl, imidazolyl, oxazolyl, isoxazolyl, oxadiazolyl, thiazolyl, isothiazolyl, thiadiazolyl, diazolyl, and triazolyl.

"Aralkyl" refers to a group of the formula —$R_aR_b$ where $R_a$ is an alkyl group as defined above, substituted by $R_b$, an aryl group, as defined above, e.g., benzyl. Both the alkyl and aryl groups may be optionally substituted as defined herein.

"Heteroaralkyl" refers to a group of the formula —$R_aR_f$ where $R_a$ is an alkyl group as defined above and $R_f$ is a heteroaryl group as defined herein. The alkyl group and the heteroaryl group may be optionally substituted as defined herein.

"Heterocyclylalkyl" refers to a group of the formula —$R_aR_e$ wherein $R_a$ is an alkyl group as defined above and $R_e$ is a heterocyclyl group as defined herein, where the alkyl group $R_a$ may attach at either the carbon atom or the heteroatom of the heterocyclyl group $R_e$. The alkyl group and the heterocyclyl group may be optionally substituted as defined herein.

"Alkoxycarbonyl" refers to a group having the formula —C(O)OR in which R is alkyl, including lower alkyl.

The term "dioxacycloalkyl" as used herein means a heterocyclic group containing two oxygen ring atoms and two or more carbon ring atoms.

"Oxo" refers to the group =O attached to a carbon atom.

"Thioalkyl" refers to a group having the formula —$R_hSR_i$, where the $R_h$ is a straight or branched alkylene chain and $R_i$ is alkyl or haloalkyl.

"Thioxo" refers to the group =S attached to a carbon atom.

"$IC_{50}$" refers to an amount, concentration or dosage of a particular test compound that achieves a 50% inhibition of a maximal response, such as cell growth or proliferation measured via any the in vitro or cell based assay described herein.

Unless stated otherwise specifically described in the specification, it is understood that the substitution can occur on any atom of the alkyl, alkenyl, alkynyl, cycloalkyl, heterocyclyl, aryl or heteroaryl group.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides, hydrobromides, phosphates and sulfates; and salts of organic acids, such as but not limited to acetates, lactates, malates, tartrates, citrates, ascorbates, succinates, butyrates, valerates, mesylates, esylates, tosylates, besylates, trifluoroacetates, benzoates, fumarates, maleates, and oxalates.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein. Thus, the compounds provided herein may be enantiomerically pure, or be stereoisomeric or diastereomeric mixtures.

It is to be understood that the compounds provided herein may contain chiral centers. Such chiral centers may be of either the (R) or (5) configuration, or may be a mixture thereof.

Optically active (+) and (−), (R)- and (S)-, or (D)- and (L)-isomers may be prepared using chiral synthons or chiral reagents, or resolved using conventional techniques, such as reverse phase HPLC or by crystallization.

As used herein, the term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the desired enantiomer.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure preferably controls.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

In certain embodiments, compounds herein having one or more deutero substituents have an isotopic enrichment factor for each designated deuterium atom of from about 50% to about 99.5%, 60% to about 99.5%, 70% to about 99.5% deuterium incorporation.

In certain embodiments, compounds herein having one or more deutero substituents have an isotopic enrichment factor for each designated deuterium atom of at least about 3500 (about 52.5% deuterium incorporation), at least about 4000 (about 60% deuterium incorporation), at least about 4500 (about 67.5% deuterium incorporation), at least about 5000 (about 75% deuterium incorporation), at least about 5500 (82.5% deuterium incorporation), at least about 6000 (about 90% deuterium incorporation), at least about 6466.7 (about 97% deuterium incorporation), at least about 6600 (about 99% deuterium incorporation), or at least about 6633.3 (99.5% deuterium incorporation).

In certain embodiments, compounds herein having one or more deutero substituents have an isotopic enrichment factor for each designated deuterium atom of about 3500 (about 52.5% deuterium incorporation), about 4000 (about 60% deuterium incorporation), about 4500 (about 67.5% deuterium incorporation), about 5000 (about 75% deuterium incorporation), about 5500 (82.5% deuterium incorporation), about 6000 (about 90% deuterium incorporation), about 6466.7 (about 97% deuterium incorporation), about 6600 (about 99% deuterium incorporation), or about 6633.3 (99.5% deuterium incorporation).

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to methotrexate, matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds, are, unless indicated otherwise, in accord with their common usage or recognized abbreviations including abbreviations found in *J. Org. Chem.* 2007 72(1): 23A-24A or abbreviations established by the IUPAC-IUB Commission on Biochemical Nomenclature (see, *Biochem.* 1972, 11:942-944).

B. COMPOUNDS

Provided herein are compounds of formula (I)

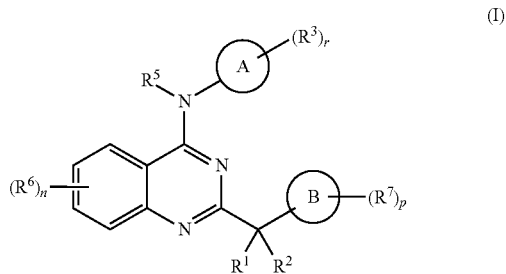

or pharmaceutically acceptable salts, solvates or hydrates thereof, wherein

A is azolyl;

B is 6-membered nitrogen containing heteroaryl;

$R^1$ and $R^2$ are selected from (i), (ii), (iii), (iv), and (v) as follows:

(i) $R^1$ and $R^2$ together form =O, =S, =NR$^9$ or =CR$^{10}$R$^{11}$;

(ii) $R^1$ and $R^2$ are both —$OR^8$, or $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substitutents selected from halo, deutero, alkyl, cycloalkyl, heterocyclyl, aryl, heteroaryl, cyano, =O, =N—$OR^{21}$, —$R^xOR^{21}$, —$R^xN(R^{22})_2$, $R^xS(O)_qR^{23}$, —C(O)$OR^{21}$ and —C(O)N$(R^{22})_2$ and wherein the heterocyclyl contains one to two heteroatoms selected from O, $NR^{24}$, S, S(O) and S(O)$_2$;

(iii) $R^1$ is hydrogen or halo; and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —C(O)$OR^w$; and $R^2$ is hydrogen, halo or —$OR^8$; and (v) $R^1$ is halo, deutero, —$OR^{12}$; —$NR^{13}R^{14}$, or —S(O)$_qR^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two, or three, substitutents selected from halo, cyano, alkyl, —$R^xOR^w$, —$R^xS(O)_qR^v$ and —$R^xNR^yR^z$;

each $R^3$ is independently hydrogen, deutero, halo, alkyl, cyano, haloalkyl, cycloalkyl, cycloalkylalkyl, hydroxy or alkoxy;

$R^5$ is hydrogen or alkyl;

each $R^6$ is independently selected from deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —$R^xOR^{18}$, —$R^xNR^{19}R^{20}$, —$R^xC(O)NR^yR^z$ and —$R^xS(O)_qR^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)$OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)$R^v$, —C(O)$OR^w$ and —C(O)$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:
(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)$R^v$, —C(O)$OR^w$, —C(O)$NR^yR^z$ and —S(O)$_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)$NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:
(i) $R^y$ and $R^z$ are each independently hydrogen, alkyl, alkenyl, alkynyl, cycloalkyl or haloalkyl; or
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;

r is 1-3;

p is 0-4; and each q is independently 0, 1 or 2.

In certain embodiment, provided herein are compounds of formula (II)

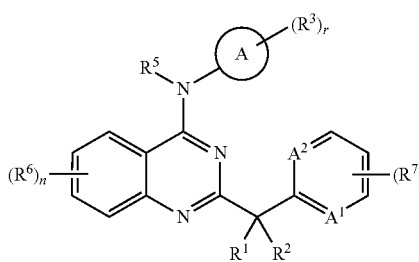

or pharmaceutically acceptable salts, solvates or hydrates thereof, wherein

A is azolyl;

$A^1$ and $A^2$ are selected from N and $CR^{7a}$, such that at least one of $A^1$ or $A^2$ is N; $R^{7a}$ is hydrogen or alkyl; and the other variables are as described elsewhere herein.

In certain embodiment, provided herein are compounds of formula (II) or pharmaceutically acceptable salts, solvates or hydrates thereof, wherein A is azolyl;

$A^1$ and $A^2$ are selected from N and $CR^{7a}$, such that at least one of $A^1$ or $A^2$ is N; $R^{7a}$ is hydrogen or alkyl;

$R^1$ and $R^2$ are selected from (i), (ii), (iii), (iv), and (v) as follows:

(i) $R^1$ and $R^2$ together form =O, =S, =$NR^9$ or =$CR^{10}R^{11}$;

(ii) $R^1$ and $R^2$ are both —$OR^8$, or $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substitutents selected from halo, deutero, alkyl, cycloalkyl, heterocyclyl, aryl, heteroaryl, cyano, =O, =N—$OR^{21}$, —$R^xOR^{21}$, —$R^xN(R^{22})_2$, —$R^xS(O)_qR^{23}$, —$C(O)R^{21}$ and —$C(O)N(R^{22})_2$ and wherein the heterocyclyl contains one to two heteroatoms selected from O, $NR^{24}$, S, S(O) and $S(O)_2$;

(iii) $R^1$ is hydrogen or halo; and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —$C(O)OR^w$; and $R^2$ is hydrogen, halo or —$OR^8$; and (v) $R^1$ is halo, deutero, —$OR^{12}$; —$NR^{13}R^{14}$, or —$S(O)_qR^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$ and —$R^xNR^yR^z$;

each $R^3$ is independently hydrogen, deutero, halo, alkyl, cyano, haloalkyl, deuteroalkyl, cycloalkyl, cycloalkylalkyl, hydroxy or alkoxy;

$R^5$ is hydrogen or alkyl;

each $R^6$ is independently selected from deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —$R^xOR^{18}$, —$R^xNR^{19}R^{20}$, —$R^xC(O)NR^yR^z$, —$R^xS(O)_qR^v$, —$R^xNR^{19}C(O)R^{18}$, —$R^xC(O)OR^{18}$ and —$R^xNR^{19}S(O)_qR^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:

(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^v$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —$C(O)NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:
  (i) $R^y$ and $R^z$ are each independently hydrogen, alkyl, alkenyl, alkynyl, cycloalkyl, haloalkyl or heterocyclyl; or
  (ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;
r is 1-3;
p is 0-4; and
each q is independently 0, 1 or 2.

In certain embodiments, provided herein are compounds of formula (III)

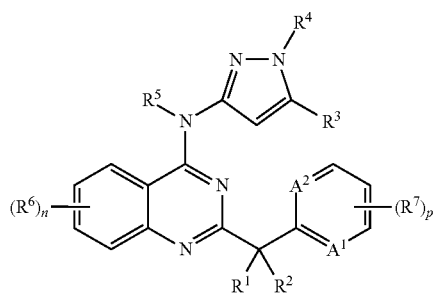

(III)

or pharmaceutically acceptable salts, solvates or hydrates thereof, wherein $A^1$ and $A^2$ are selected from N and CH, such that at least one of $A^1$ or $A^2$ is N;

$R^1$ and $R^2$ are selected from (i), (ii), (iii), (iv) and (v) as follows:
  (i) $R^1$ and $R^2$ together form =O, =S, =NR$^9$ or =CR$^{10}$R$^{11}$;
  (ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substitutents selected from halo, deutero, alkyl, cycloalkyl, heterocyclyl, aryl, heteroaryl, cyano, =O, =N—OR$^{21}$, —R$^x$OR$^{21}$, —R$^x$N(R$^{22}$)$_2$, —R$^x$S(O)$_q$R$^{23}$, —C(O)R$^{21}$, —C(O)OR$^{21}$ and —C(O)N(R$^{22}$)$_2$ and wherein the heterocyclyl contains one to two heteroatoms wherein each heteroatom is independently selected from O, NR$^{24}$, S, S(O) and S(O)$_2$;
  (iii) $R^1$ is hydrogen or halo; and $R^2$ is halo;
  (iv) $R^1$ is alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —R$^x$OR$^w$, —R$^x$S(O)$_q$R$^v$, —R$^x$NR$^y$R$^z$ and —C(O)OR$^w$; and $R^2$ is hydrogen, halo or —OR$^8$; and
  (v) $R^1$ is halo, deutero, —OR$^{12}$, —NR$^{13}$R$^{14}$, or —S(O)$_q$R$^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substituents selected from halo, cyano, alkyl, —R$^x$OR$^w$, —R$^x$S(O)$_q$R$^v$ and —R$^x$NR$^y$R$^z$;

$R^3$ is hydrogen, deutero, halo, alkyl, cyano, haloalkyl, cycloalkyl, cycloalkylalkyl, deuteroalkyl, hydroxy or alkoxy;

$R^4$ and $R^5$ are each independently hydrogen or alkyl;

each $R^6$ is independently selected from deutero, halo, cyano, nitro, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$, —R$^x$S(O)$_q$R$^v$, —R$^x$NR$^{19}$C(O)R$^{18}$, —R$^x$C(O)OR$^{18}$ and —R$^x$NR$^{19}$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —R$^x$OR$^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)OR$^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:
  (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or
  (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:
- (i) $R^{19}$ and $R^{20}$ are each independently hydrogen or alkyl; or
- (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:
- (i) $R^y$ and $R^z$ are each independently hydrogen, alkyl, alkenyl, alkynyl, cycloalkyl, haloalkyl or heterocyclyl;
- (ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;
p is 0-4; and
each q is independently 0, 1 or 2.

In certain embodiments, provided herein are compounds of formula (III)
or pharmaceutically acceptable salts, solvates or hydrates thereof, wherein $A^1$ and $A^2$ are selected from N and CH, such that at least one of $A^1$ or $A^2$ is N;

$R^1$ and $R^2$ are selected from (i), (ii), (iii), (iv) and (v) as follows:
- (i) $R^1$ and $R^2$ together form =O, =S, =NR$^9$ or =CR$^{10}$R$^{11}$;
- (ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substituents selected from halo, deutero, alkyl, cycloalkyl, heterocyclyl, aryl, heteroaryl, cyano, =O, =N—OR$^{21}$, —R$^x$OR$^{21}$, —R$^x$N(R$^{22}$)$_2$, —R$^x$S(O)$_q$R$^{23}$, —C(O)R$^{21}$ and —C(O)N(R$^{22}$)$_2$ and wherein the heterocyclyl contains one to two heteroatoms wherein each heteroatom is independently selected from O, NR$^{24}$, S, S(O) and S(O)$_2$;
- (iii) $R^1$ is hydrogen or halo; and $R^2$ is halo;
- (iv) $R^1$ is alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —R$^x$OR$^w$, —R$^x$S(O)$_q$R$^v$, —R$^x$NR$^y$R$^z$ and —C(O)OR$^w$; and R$^2$ is hydrogen, halo or —OR$^8$; and
- (v) $R^1$ is halo, deutero, —OR$^{12}$; —NR$^{13}$R$^{14}$, or —S(O) R$^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one or more, in one embodiment, one to four, in one embodiment, one to three, in one embodiment, one, two or three, substitutents selected from halo, cyano, alkyl, —R$^x$OR$^w$, —R$^x$S(O)$_q$R$^v$ and —R$^x$NR$^y$R$^z$;

$R^3$ is hydrogen, deutero, halo, alkyl, cyano, haloalkyl, cycloalkyl, cycloalkylalkyl, hydroxy or alkoxy;

$R^4$ and $R^5$ are each independently hydrogen or alkyl;

each $R^6$ is independently selected from deutero, halo, cyano, nitro, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$ and —R$^x$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —R$^x$—OR$^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)OR$^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:
- (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or
- (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;
$R^{24}$ is hydrogen or alkyl;
each $R^x$ is independently alkylene or a direct bond;
$R^v$ is hydrogen, alkyl, alkenyl or alkynyl;
$R^w$ is independently hydrogen, alkyl, alkenyl, alkynyl or haloalkyl;

$R^y$ and $R^z$ are selected as follows:
(i) $R^y$ and $R^z$ are each independently hydrogen, alkyl, alkenyl, alkynyl, cycloalkyl or haloalkyl;
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;
p is 0-4; and
each q is independently 0, 1 or 2.

In certain embodiments, provided herein are compounds of formula (IV)

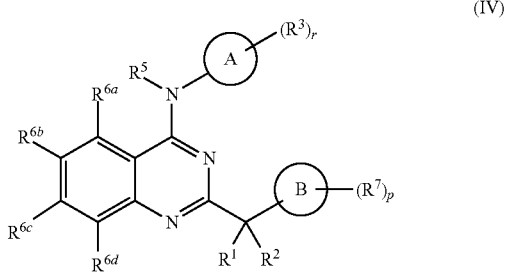

(IV)

or pharmaceutically acceptable salts, solvates or hydrates thereof, wherein
A is azolyl;
B is 6-membered nitrogen containing heteroaryl;

$R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one or two substituents selected from halo, deutero, alkyl, haloalkyl, —OR$^{21}$, —N(R$^{22}$)$_2$, and —S(O)$_q$R$^{23}$ and wherein the heterocyclyl contains one to two heteroatoms wherein each heteroatom is selected from O, NR$^{24}$, S, S(O) and S(O)$_2$;
(iii) $R^1$ is hydrogen or halo, and $R^2$ is halo;
(iv) $R^1$ is alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$ and $R^2$ is hydrogen, halo and —OR$^8$; and
(v) $R^1$ is halo, —OR$^{12}$, —NR$^{13}$R$^{14}$, —S(O)$_q$R$^{15}$ or —R$^{17}$C(O)OR$^{12}$, and $R^2$ is hydrogen, alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$;

$R^3$ is hydrogen, deutero, alkyl, haloalkyl, deuteroarlkyl or cycloalkyl;

$R^5$ are each independently hydrogen or alkyl;

$R^{6a}$, $R^{6b}$, $R^{6c}$, and $R^{6d}$ are each independently selected from hydrogen, deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$, —R$^x$S(O)$_q$R$^v$, —R$^x$NR$^{19}$C(O)R$^{18}$, —R$^x$C(O)OR$^{18}$ and —R$^x$NR$^{19}$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —R$^x$OR$^w$;

$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
each $R^{12}$ is independently hydrogen, alkyl, haloalkyl, hydroxyalkyl, alkoxyalkyl, aminoalkyl, thioalkyl, heterocyclylalkyl or —C(O)NR$^y$R$^z$;

$R^{13}$ and $R^{14}$ are selected as follows:
(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocycylalkyl, —C(O)R$^v$, —C(O)OR$^w$, —C(O)NR$^y$R$^z$ and —S(O)$_q$R$^v$; or
(ii) $R^{13}$ and $R^{14}$, together with the nitrogen atom to which they are attached, form heterocyclyl optionally substituted with one more substituents independently selected from halo, oxo, alkyl, hydroxy, alkoxy, amino and alkylthio; $R^{15}$ is selected from hydrogen, alkyl, haloalkyl, hydroxyalkyl, alkoxyalkyl, aminoalkyl, thioalkyl, heterocycylalkyl, —C(O)NR$^y$R$^z$ or —NR$^y$R$^z$;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;
$R^{24}$ is hydrogen or alkyl;
$R^v$ is hydrogen, alkyl, alkenyl or alkynyl;
each $R^x$ is independently alkylene or a direct bond;
$R^w$ is independently hydrogen or alkyl;
$R^y$ and $R^z$ are selected as follows:
(i) $R^y$ and $R^z$ are each independently hydrogen, alkyl, alkenyl, alkynyl, cycloalkyl, haloalkyl or heterocyclyl;
(ii) $R^y$ and $R^z$, together with the nitrogen atom to which they are attached, form a heterocyclyl or heteroaryl which are each optionally substituted with 1 to 2 groups each independently selected from halo, alkyl, haloalkyl, hydroxyl and alkoxy;

each q is independently 0, 1 or 2;
r is 1-3; and
p is 0-2.

In certain embodiments, provided herein are compounds of formula (IV) or pharmaceutically acceptable salts, solvates or hydrates thereof, wherein A is azolyl;
B is 6-membered nitrogen containing heteroaryl;
$R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one or two substituents selected from halo, deutero, alkyl, haloalkyl, —OR$^{21}$, —N(R$^{22}$)$_2$, and —S(O)$_q$R$^{23}$ and wherein the heterocyclyl contains one to two heteroatoms wherein each heteroatom is selected from O, NR$^{24}$, S, S(O) and S(O)$_2$;
(iii) $R^1$ is hydrogen or halo, and $R^2$ is halo;
(iv) $R^1$ is alkyl, alkenyl, alkynyl, cycloalkyl or aryl, wherein the alkyl, alkenyl, alkynyl, cycloalkyl and aryl are each optionally substituted with one or more substituents selected from halo, alkyl, —R$^x$OR$^w$, —R$^x$S(O)$_q$R$^v$ and —R$^x$NR$^y$R$^z$ and $R^2$ is hydrogen, halo and —OR$^8$; and
(v) $R^1$ is halo, —OR$^{12}$, —NR$^{13}$R$^{14}$, —S(O)$_q$R$^{15}$ or —R$^{17}$C(O)OR$^{12}$, and $R^2$ is hydrogen, alkyl, alkenyl, alkynyl, cycloalkyl or aryl, wherein the alkyl, alkenyl, alkynyl, cycloalkyl and aryl are each optionally substituted with one or more substituents selected from halo, alkyl, —R$^x$OR$^w$, —R$^x$S(O)$_q$R$^v$ and —R$^x$NR$^y$R$^z$;

$R^3$ is hydrogen, deutero, alkyl, haloalkyl, deuteroarlkyl or cycloalkyl;
$R^5$ are each independently hydrogen or alkyl;

$R^{6a}$, $R^{6b}$, $R^{6c}$, and $R^{6d}$ are each independently selected from hydrogen, deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$, —R$^x$S(O)$_q$R$^v$, —R$^x$NR$^{19}$C(O)R$^{18}$, —R$^x$C(O)OR$^{18}$ and —R$^x$NR$^{19}$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —R$^x$OR$^w$;

$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
each $R^{12}$ is independently hydrogen, alkyl, haloalkyl, hydroxyalkyl, alkoxyalkyl, aminoalkyl, thioalkyl, heterocyclylalkyl or —C(O)NR$^y$R$^z$;
$R^{13}$ and $R^{14}$ are selected as follows:
(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocycylalkyl, —C(O)R$^v$, —C(O)OR$^w$, —C(O)NR$^y$R$^z$ and —S(O)$_q$R$^v$; or
(ii) $R^{13}$ and $R^{14}$, together with the nitrogen atom to which they are attached, form heterocyclyl optionally substituted with one more substituents independently selected from halo, oxo, alkyl, hydroxy, alkoxy, amino and alkylthio; $R^{15}$ is selected from hydrogen, alkyl, haloalkyl, hydroxyalkyl, alkoxyalkyl, aminoalkyl, thioalkyl, heterocycylalkyl, —C(O)NR$^y$R$^z$ or —NR$^y$R$^z$;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;
$R^{24}$ is hydrogen or alkyl;
$R^v$ is hydrogen, alkyl, alkenyl or alkynyl;
each $R^x$ is independently alkylene or a direct bond;
$R^w$ is independently hydrogen or alkyl;
$R^y$ and $R^z$ are selected as follows:
(i) $R^y$ and $R^z$ are each independently hydrogen, alkyl, alkenyl, alkynyl, cycloalkyl, haloalkyl or heterocylyl;
(ii) $R^y$ and $R^z$, together with the nitrogen atom to which they are attached, form a heterocyclyl or heteroaryl which are each optionally substituted with 1 to 2 groups each independently selected from halo, alkyl, haloalkyl, hydroxyl and alkoxy;

each q is independently 0, 1 or 2;

r is 1-3; and p is 0-2.

In certain embodiments, provided herein are compounds of formula (IV) or pharmaceutically acceptable salts, solvates or hydrates thereof, wherein A is azolyl;

B is 6-membered nitrogen containing heteroaryl;

$R^1$ and $R^2$ are selected from (i), (ii), (iii), (iv) and (v) as follows:

(i) $R^1$ and $R^2$ together form =O, =S, =NR$^9$ or =CR$^{10}$R$^{11}$;

(ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one or two substituents selected from halo, deutero, alkyl, haloalkyl, —OR$^{21}$, —N(R$^{22}$)$_2$, and —S(O)$_q$R$^{23}$ and wherein the heterocyclyl contains one to two heteroatoms wherein each heteroatom is selected from O, NR$^{24}$, S, S(O) and S(O)$_2$;

(iii) $R^1$ is hydrogen or halo, and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$ and $R^2$ is hydrogen, halo and —OR$^8$; and (v) $R^1$ is halo —OR$^{12}$, —NR$^{13}$R$^{14}$, —S(O)$_q$R$^{15}$ or R$^{17}$C(O)OR$^{12}$, and $R^2$ is hydrogen, alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$;

$R^3$ is hydrogen, deutero, alkyl or cycloalkyl;

$R^5$ are each independently hydrogen or alkyl;

$R^{6a}$, $R^{6b}$, $R^{6c}$, and $R^{6d}$ are each independently selected from hydrogen, deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$ and —R$^x$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —R$^x$-OR$^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)OR$^8$;

each $R^{12}$ is independently hydrogen, alkyl, haloalkyl, hydroxyalkyl, alkoxyalkyl, aminoalkyl, thioalkyl, heterocyclylalkyl or —C(O)NR$^y$R$^z$;

$R^{13}$ and $R^{14}$ are selected as follows:

(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocycylalkyl, —C(O)R$^v$, —C(O)OR$^w$, —C(O)NR$^y$R$^z$ and —S(O)$_q$R$^v$; or (ii) $R^{13}$ and $R^{14}$, together with the nitrogen atom to which they are attached, form heterocyclyl optionally substituted with one more substituents independently selected from halo, oxo, alkyl, hydroxy, alkoxy, amino and alkylthio; $R^{15}$ is selected from hydrogen, alkyl, haloalkyl, hydroxyalkyl, alkoxyalkyl, aminoalkyl, thioalkyl, heterocycylalkyl, —C(O)NR$^y$R$^z$ or —NR$^y$R$^z$;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups Q$^1$, each Q$^1$ independently selected from alkyl, hydroxyl, halo, oxo, haloalkyl, alkoxy, aryloxy, alkoxyalkyl, alkoxycarbonyl, carboxyl, cycloalkyl, heterocyclyl, aryl, heteroaryl, haloaryl and amino;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

$R^v$ is hydrogen, alkyl, alkenyl or alkynyl;

each $R^x$ is independently alkylene or a direct bond;

$R^w$ is independently hydrogen or alkyl;

$R^y$ and $R^z$ are selected as follows:

(i) $R^y$ and $R^z$ are each independently hydrogen, alkyl, alkenyl, alkynyl, cycloalkyl or haloalkyl;

(ii) $R^y$ and $R^z$, together with the nitrogen atom to which they are attached, form a heterocyclyl or heteroaryl which are each optionally substituted with 1 to 2 groups each independently selected from halo, alkyl, haloalkyl, hydroxyl and alkoxy;

each q is independently 0, 1 or 2;

r is 1-3; and p is 0-2.

In certain embodiments, provided herein are compounds of formula (IV) or pharmaceutically acceptable salts, solvates or hydrates thereof, wherein A is azolyl;

B is 6-membered nitrogen containing heteroaryl;

$R^1$ and $R^2$ are selected from (i), (ii), (iii), (iv) and (v) as follows:

(i) $R^1$ and $R^2$ together form =O, =S, =NR$^9$ or =CR$^{10}$R$^{11}$;

(ii) $R^1$ and $R^2$ are both —OR$^8$, or $R^1$ and $R^2$, together with the carbon atom to which they are attached, form cycloalkyl or heterocyclyl wherein the cycloalkyl is substituted with one or more, in one embodiment, one or two substituents selected from halo, deutero, alkyl, haloalkyl, —OR$^{21}$, —N(R$^{22}$)$_2$, and —S(O)$_q$R$^{23}$ and wherein the heterocyclyl contains one to two heteroatoms wherein each heteroatom is selected from O, NR$^{24}$, S, S(O) and S(O)$_2$;

(iii) $R^1$ is hydrogen or halo, and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$ and $R^2$ is hydrogen, halo and —OR$^8$; and (v) $R^1$ is halo, —OR$^{12}$, —NR$^{13}$R$^{14}$, —S(O)$_q$R$^{15}$ or —R$^{17}$C(O)OR$^{12}$, and $R^2$ is hydrogen, alkyl, alkenyl, alkynyl, cycloalkyl or aryl, wherein the alkyl, alkenyl, alkynyl, cycloalkyl and aryl are each optionally substituted with one or more substitutents selected from halo, alkyl, —R$^x$OR$^w$, —R$^x$S(O)$_q$R$^v$ and —R$^x$NR$^y$R$^z$;

$R^3$ is hydrogen, deutero, alkyl, haloalkyl, deuteroalkyl or cycloalkyl;

$R^5$ are each independently hydrogen or alkyl;

$R^{6a}$, $R^{6b}$, $R^{6c}$, and $R^{6d}$ are each independently selected from hydrogen, deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —$R^xOR^{18}$, —$R^xNR^{19}R^{20}$, —$R^xC(O)NR^yR^z$, —$R^xS(O)_qR^y$, —$R^xNR^{19}C(O)R^{18}$, —$R^xC(O)OR^{18}$ and —$R^xNR^{19}S(O)_qR^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

each $R^{12}$ is independently hydrogen, alkyl, haloalkyl, hydroxyalkyl, alkoxyalkyl, aminoalkyl, thioalkyl, heterocyclylalkyl or —$C(O)NR^yR^z$;

$R^{13}$ and $R^{14}$ are selected as follows:

(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocycylalkyl, —$C(O)R^v$, —$C(O)OR^w$, —$C(O)NR^yR^z$ and —$S(O)_qR^v$; or (ii) $R^{13}$ and $R^{14}$, together with the nitrogen atom to which they are attached, form heterocyclyl optionally substituted with one more substituents independently selected from halo, oxo, alkyl, hydroxy, alkoxy, amino and alkylthio; $R^{15}$ is selected from hydrogen, alkyl, haloalkyl, hydroxyalkyl, alkoxyalkyl, aminoalkyl, thioalkyl, heterocycylalkyl, —$C(O)NR^yR^z$ or —$NR^yR^z$;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, carboxyl, cycloalkyl, heterocyclyl, aryl, heteroaryl, haloaryl and amino;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

$R^v$ is hydrogen, alkyl, alkenyl or alkynyl;

each $R^x$ is independently alkylene or a direct bond;

$R^w$ is independently hydrogen or alkyl;

$R^y$ and $R^z$ are selected as follows:

(i) $R^y$ and $R^z$ are each independently hydrogen, alkyl, alkenyl, alkynyl, cycloalkyl, haloalkyl or heterocylyl;

(ii) $R^y$ and $R^z$, together with the nitrogen atom to which they are attached, form a heterocyclyl or heteroaryl which are each optionally substituted with 1 to 2 groups each independently selected from halo, alkyl, haloalkyl, hydroxyl and alkoxy;

each q is independently 0, 1 or 2;

r is 1-3; and p is 0-2.

In one embodiment, provided herein is a compound of formula IV wherein B is

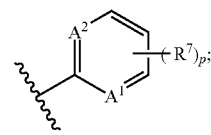

$A^1$ and $A^2$ are selected from N and $CR^{7a}$, such that at least one of $A^1$ or $A^2$ is N; each $R^7$ is independently halo, alkyl, haloalkyl or —$R^xOR^w$; each $R^{7a}$ is independently hydrogen, halo, alkyl, haloalkyl or —$R^xOR^w$; $R^x$ is independently alkylene or a direct bond; $R^w$ is independently hydrogen or alkyl; and the other variables are as described elsewhere herein.

In certain embodiments, provided herein are compounds of formula (V)

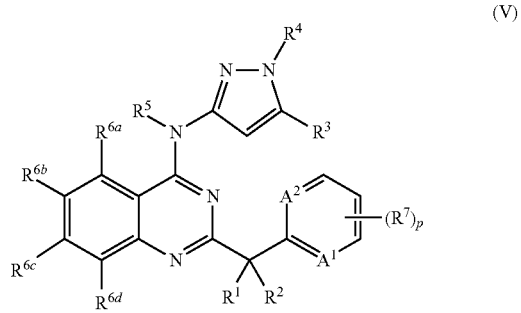

or pharmaceutically acceptable salts, solvates or hydrates thereof, wherein $A^1$ and $A^2$ are selected from N and $CR^{7a}$, such that at least one of $A^1$ or $A^2$ is N; each $R^{7a}$ is independently hydrogen, halo, alkyl, haloalkyl or —$R^xOR^w$; $R^x$ is independently alkylene or a direct bond;

$R^w$ is independently hydrogen or alkyl; and the other variables are as described elsewhere herein. In another embodiment, $A^1$ and $A^2$ are selected from N and CH.

In certain embodiments, provided herein are compounds of formula (VIa) or (VIb)

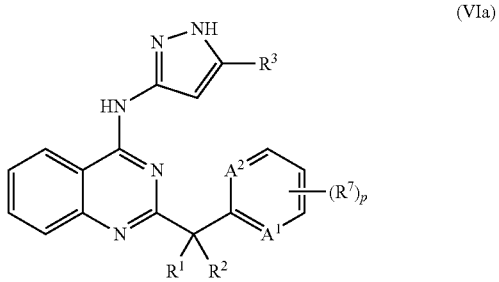

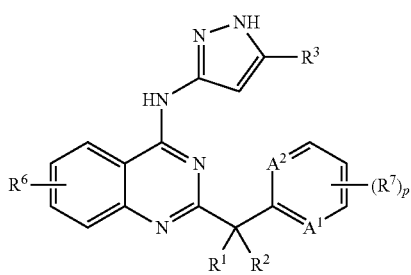

(VIb)

or pharmaceutically acceptable salts, solvates or hydrates thereof, wherein $A^1$ and $A^2$ are selected from N and $CR^{7a}$, such that at least one of $A^1$ or $A^2$ is N;

$R^3$ is hydrogen, deutero, alkyl, haloalkyl, deuteroarlkyl or cycloalkyl;

$R^6$ is selected from deutero, halo, cyano, nitro, alkyl, cycloalkyl, alkoxy, haloalkyl, aryl, heteroaryl, heterocyclyl, —$R^xOR^{18}$, —$R^xNR^{19}R^{20}$, —$R^xC(O)NR^yR^z$, —$R^xS(O)_qR^y$, —$R^xNR^{19}C(O)R^{18}$, —$R^xC(O)OR^{18}$ and —$R^xNR^{19}S(O)_qR^y$; where the alkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or alkoxy;

each $R^{7a}$ is independently hydrogen, halo, alkyl, haloalkyl or alkoxy; p is 1 or 2; and the other variables are as described elsewhere herein. In certain embodiments, p is 1.

In certain embodiments, provided herein are compounds of formula (VIa) or (VIb)

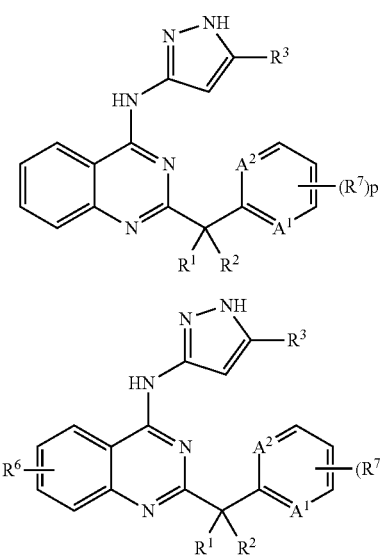

or pharmaceutically acceptable salts, solvates or hydrates thereof, wherein $R^3$ is hydrogen, deutero, alkyl, haloalkyl or cycloalkyl;

$R^6$ is selected from deutero, halo, cyano, nitro, alkyl, cycloalkyl, alkoxy, haloalkyl, aryl, heteroaryl, heterocyclyl, —$R^xOR^{18}$, —$R^xNR^{19}R^{20}$, —$R^xC(O)NR^yR^z$ and —$R^xS(O)_qR^y$; where the alkyl, cycloalkyl, aryl, heteroaryl and heterocyclyl groups are optionally substi-tuted with one, two or three halo, oxo, hydroxy, alkoxy, alkyl, alkenyl, alkynyl, haloalkyl, or cycloalkyl groups;

each $R^7$ is independently halo, alkyl, haloalkyl or alkoxy; p is 1 or 2; and the other variables are as described elsewhere herein. In certain embodiments, p is 1.

In certain embodiments, provided herein are compounds of formula (VIa) or (VIb) or pharmaceutically acceptable salts, solvates or hydrates thereof, wherein $R^3$ is hydrogen, deutero, deuteroalkyl, alkyl, haloalkyl or cycloalkyl;

$R^6$ is selected from deutero, halo, cyano, nitro, alkyl, cycloalkyl, alkoxy, haloalkyl, aryl, heteroaryl, heterocyclyl, —$R^xOR^{18}$, —$R^xNR^{19}R^{20}$, —$R^xC(O)NR^yR^z$ and —$R^xS(O)_qR^y$; where the alkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each $R^7$ is independently halo, alkyl, haloalkyl or alkoxy; p is 1 or 2; and the other variables are as described elsewhere herein. In certain embodiments, p is 1.

In certain embodiments, provided herein are compounds of formula (VIIa), (VIIb) or (VIIc)

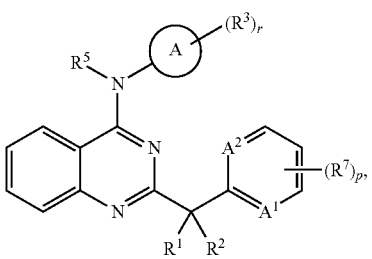

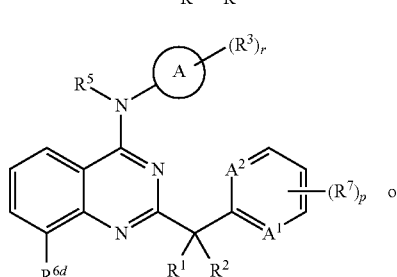

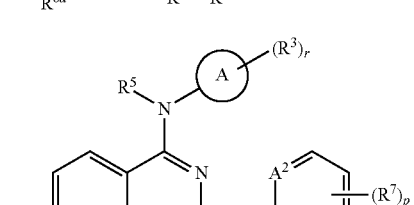

or pharmaceutically acceptable salts, solvates or hydrates thereof, wherein the variables are as described elsewhere herein.

In one embodiment, provided herein are compounds of formula formula (VIIa), (VIIb) or (VIIc), or pharmaceutically acceptable salts, solvates or hydrates thereof, wherein A is azolyl;

$A^1$ and $A^2$ are selected from N and CH, such that at least one of $A^1$ or $A^2$ is N;

$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is deutero, alkyl, haloalkyl, deuteroalkyl or cycloalkyl,
$R^5$ are each independently hydrogen or alkyl;
$R^{6c}$ or $R^{6d}$ is selected from deutero, halo, cyano, nitro, alkyl, cycloalkyl, alkoxy, haloalkyl, aryl, heteroaryl, heterocyclyl, $-R^xOR^{18}$, $-R^xNR^{19}R^{20}$, $-R^xC(O)NR^yR^z$, $-R^xS(O)_qR^v$, $-R^xNR^{19}C(O)R^{18}$, $-R^xC(O)OR^{18}$ and $-R^xNR^{19}S(O)_qR^v$;
each $R^7$ is independently halo, alkyl or haloalkyl; and
$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;
$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;
each $R^x$ is independently alkylene or a direct bond;
$R^v$ is hydrogen, alkyl, alkenyl or alkynyl;
$R^y$ and $R^z$ are selected as follows:
(i) $R^y$ and $R^z$ are each independently hydrogen, alkyl, alkenyl, alkynyl, cycloalkyl, haloalkyl or heterocyclyl;
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;
p is 0-2; and
q is 0-2.

In one embodiment, provided herein are compounds of formula formula (VIIa), (VIIb) or (VIIc), or pharmaceutically acceptable salts, solvates or hydrates thereof, wherein
A is azolyl;
$A^1$ and $A^2$ are selected from N and CH, such that at least one of $A^1$ or $A^2$ is N;
$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is deutero, alkyl, haloalkyl, deuteroalkyl or cycloalkyl,
$R^5$ are each independently hydrogen or alkyl;
$R^{6c}$ is selected from deutero, halo, cyano, alkyl, haloalkyl and alkoxy
$R^{6d}$ is selected from deutero, halo, cyano, nitro, amino, alkyl, cycloalkyl, haloalkyl, alkoxy, haloalkoxy, alkylsulfonyl, alkylsulfonylamino, aminocarbonyl, heterocyclylaminocarbonyl, oxo-substituted heterocylyl, carboxyl, formylamino and acetylamino;
each $R^7$ is independently halo, alkyl or haloalkyl; and
p is 0-2.

In one embodiment, provided herein are compounds of formula formula (VIIa), (VIIb) or (VIIc), or pharmaceutically acceptable salts, solvates or hydrates thereof, wherein
A is azolyl;
$A^1$ and $A^2$ are selected from N and CH, such that at least one of $A^1$ or $A^2$ is N;

$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is hydrogen, deutero, alkyl or cycloalkyl,
$R^5$ are each independently hydrogen or alkyl;
$R^{6c}$ is selected from deutero, halo, cyano, alkyl, haloalkyl and alkoxy;
$R^{6d}$ is selected from deutero, halo, cyano, alkyl, haloalkyl and alkoxy;
each $R^7$ is independently halo, alkyl or haloalkyl; and
p is 0-2.

In one embodiment, provided herein are compounds of formula formula (VIIa), (VIIb) or (VIIc), or pharmaceutically acceptable salts, solvates or hydrates thereof, wherein
A is azolyl;
$A^1$ is N;
$A^2$ is CH;
$R^{6c}$ is selected from deutero, halo, cyano, alkyl, haloalkyl, hydroxyalkyl, alkoxyalkyl and carboxyl;
$R^{6d}$ is selected from deutero, halo, cyano, alkyl, haloalkyl, hydroxyalkyl, alkoxyalkyl and carboxyl;
each $R^7$ is independently halo, alkyl or haloalkyl; and
p is 0-2.

In certain embodiments, $R^{6c}$ is selected from cyano, alkyl, haloalkyl, hydroxyalkyl and carboxyl; and $R^{6d}$ is selected from cyano, alkyl, haloalkyl, hydroxyalkyl and carboxyl. In certain embodiments, $R^{6c}$ is selected from cyano and carboxyl and $R^{6d}$ is selected from cyano and carboxyl.

In certain embodiments, provided herein are compounds of Formula (VIIa), (VIIb) or (VIIc), or pharmaceutically acceptable salts, solvates or hydrates thereof, wherein p is 1 to 2. In certain embodiments, p is 1.

In certain embodiments, provided herein are compounds of formula (VIIIa), (VIIIb) or (VIIIc)

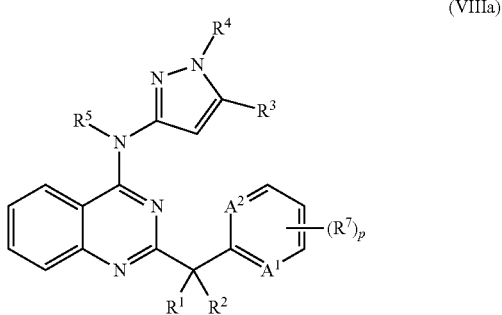
(VIIIa)

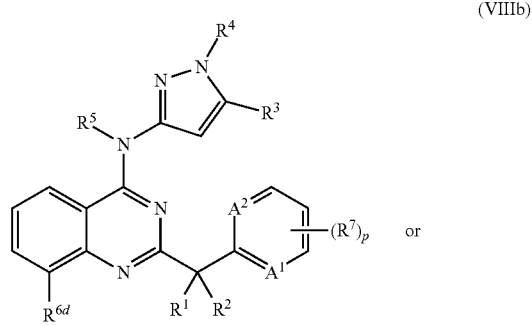
(VIIIb)

or

-continued

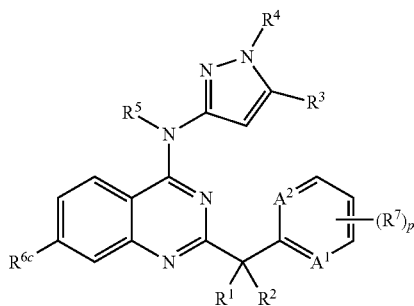

(VIIIc)

or pharmaceutically acceptable salts, solvates or hydrates thereof, wherein the variables are as described elsewhere herein.

In one embodiment, provided herein are compounds of formula (VIIIa), (VIIIb) or (VIIIc), or pharmaceutically acceptable salts, solvates or hydrates thereof, wherein
A is azolyl;
$A^1$ and $A^2$ are selected from N and CH, such that at least one of $A^1$ or $A^2$ is N;
$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is deutero, alkyl, haloalkyl, deuteroalkyl or cycloalkyl,
$R^5$ are each independently hydrogen or alkyl;
$R^{6c}$ or $R^{6d}$ is selected from deutero, halo, cyano, nitro, alkyl, cycloalkyl, alkoxy, haloalkyl, aryl, heteroaryl, heterocyclyl, $-R^xOR^{18}$, $-R^xNR^{19}R^{20}$, $-R^xC(O)NR^yR^z$, $-R^xS(O)_qR^v$, $-R^xNR^{19}C(O)R^{18}$, $-R^xC(O)OR^{18}$ and $-R^xNR^{19}S(O)_qR^v$;
each $R^7$ is independently halo, alkyl or haloalkyl; and
$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;
$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;
each $R^x$ is independently alkylene or a direct bond;
$R^v$ is hydrogen, alkyl, alkenyl or alkynyl;
$R^y$ and $R^z$ are selected as follows:
(i) $R^y$ and $R^z$ are each independently hydrogen, alkyl, alkenyl, alkynyl, cycloalkyl, haloalkyl or heterocyclyl;
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;
p is 0-2; and
q is 0-2.

In one embodiment, provided herein are compounds of formula (VIIIa), (VIIIb) or (VIIIc), or pharmaceutically acceptable salts, solvates or hydrates thereof, wherein $A^1$ and $A^2$ are selected from N and CH, such that at least one of $A^1$ or $A^2$ is N;
$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is hydrogen, alkyl or cycloalkyl;
$R^4$ and $R^5$ are each independently hydrogen or alkyl;
$R^{6c}$ is selected from deutero, halo, cyano, alkyl, haloalkyl and alkoxy;
$R^{6d}$ is selected from deutero, halo, cyano, nitro, amino, alkyl, cycloalkyl, haloalkyl, alkoxy, haloalkoxy, alkylsulfonyl, alkylsulfonylamino, aminocarbonyl, heterocyclylaminocarbonyl, oxo-substituted heterocylyl, carboxyl, formylamino and acetylamino;
each $R^7$ is independently halo, alkyl or haloalkyl; and
p is 1 or 2.

In one embodiment, provided herein are compounds of formula (VIIIa), (VIIIb) or (VIIIc), or pharmaceutically acceptable salts, solvates or hydrates thereof, wherein
A is azolyl;
$A^1$ is N;
$A^2$ is CH;
$R^{6c}$ is selected from deutero, halo, cyano, alkyl, haloalkyl, hydroxyalkyl, alkoxyalkyl and carboxyl;
$R^{6d}$ is selected from deutero, halo, cyano, alkyl, haloalkyl, hydroxyalkyl, alkoxyalkyl and carboxyl;
each $R^7$ is independently halo, alkyl or haloalkyl; and
p is 0-2.

In certain embodiments, $R^{6c}$ is selected from cyano, alkyl, haloalkyl, hydroxyalkyl and carboxyl; and $R^{6d}$ is selected from cyano, alkyl, haloalkyl, hydroxyalkyl and carboxyl. In certain embodiments, $R^{6c}$ is selected from cyano and carboxyl and $R^{6d}$ is selected from cyano and carboxyl.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;
$R^3$ is hydrogen, alkyl or cycloalkyl;
$R^4$ and $R^5$ are each independently hydrogen or alkyl;
$R^{6c}$ is selected from deutero, halo, cyano, alkyl, haloalkyl and alkoxy;
$R^{6d}$ is selected from deutero, halo, cyano, alkyl, haloalkyl and alkoxy;
each $R^7$ is independently halo, alkyl or haloalkyl; and
p is 1 or 2.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ together form =O; or $R^1$ and $R^2$ are both halo;
$R^3$ is hydrogen or alkyl;
$R^4$ and $R^5$ are each hydrogen;
$R^{6c}$ and $R^{6d}$ are each independently selected from deutero, halo, cyano, nitro, amino, alkyl, cycloalkyl, haloalkyl, alkoxy, haloalkoxy, alkylsulfonyl, alkylsulfonylamino, aminocarbonyl, heterocyclylaminocarbonyl, oxo-substituted heterocylyl, carboxyl, formylamino and acetylamino;
each $R^7$ is independently halo, alkyl or haloalkyl; and
p is 1.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ together form =O; or $R^1$ and $R^2$ are both halo;
$R^3$ is hydrogen or alkyl;
$R^4$ and $R^5$ are each hydrogen;
$R^{6c}$ and $R^{6d}$ are each independently selected from deutero, halo, cyano, alkyl, haloalkyl, haloalkoxy, alkoxy, aryl, heteroaryl and heterocyclyl;
each $R^7$ is independently halo, alkyl or haloalkyl; and
p is 1.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ together form =O; or $R^1$ and $R^2$ are both fluoro;
$R^3$ is hydrogen, alkyl or cycloalkyl, $R^4$ and $R^5$ are each independently hydrogen or alkyl;
$R^{6c}$ is selected from deutero, halo, cyano, alkyl haloalkoxy, and alkoxy;
$R^{6d}$ is selected from deutero, halo, haloalkoxy, and alkyl;
each $R^7$ is halo; and
p is 1 or 2.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ together form =O; or $R^1$ and $R^2$ are both fluoro;
$R^3$ is hydrogen, alkyl or cycloalkyl,
$R^4$ and $R^5$ are each independently hydrogen or alkyl;
$R^{6c}$ is selected from deutero, halo, cyano, alkyl haloalkoxy, and alkoxy;
$R^{6d}$ is selected from deutero, halo, haloalkoxy, and alkyl;
each $R^7$ is halo; and
p is 1 or 2.

In one embodiment, provided herein are compounds of formula (VIIIa), (VIIIb) or (VIIIc), or pharmaceutically acceptable salts, solvates or hydrates thereof, wherein
$A^1$ and $A^2$ are selected from N and CH, such that at least one of $A^1$ or $A^2$ is N;
$R^1$ and $R^2$ together form =O; or $R^1$ and $R^2$ are both fluoro;
$R^3$ is hydrogen, alkyl or cycloalkyl,
$R^4$ and $R^5$ are each independently hydrogen or alkyl;
$R^{6c}$ is selected from deutero, halo, cyano, alkyl, haloalkoxy and alkoxy;
$R^{6d}$ is selected from deutero, halo, haloalkoxy and alkyl;
$R^7$ is fluoro; and
p is 1.

In one embodiment, A is pyrazolyl, imidazolyl, oxazolyl, thiazolyl, thiadiazolyl, or triazolyl. In one embodiment, A is pyrazolyl. In one embodiment, A is imidazolyl.
In one embodiment, A is

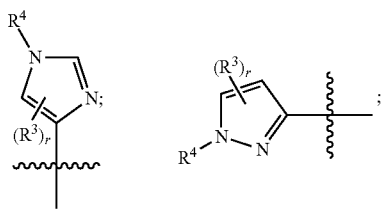

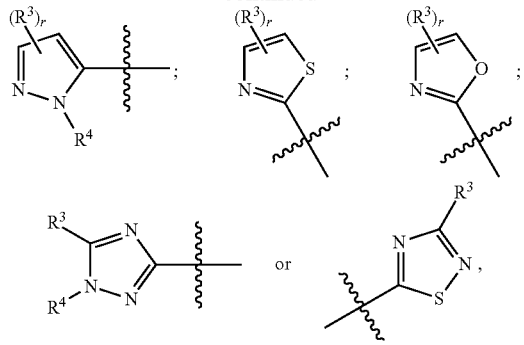

wherein each $R^3$ is independently hydrogen, halo, alkyl, cyano, haloalkyl, deuteroarlkyl, cycloalkyl, cycloalkylalkyl, hydroxy or alkoxy; r is 1 or 2; and each $R^4$ is independently hydrogen, or alkyl.

In one embodiment, A is

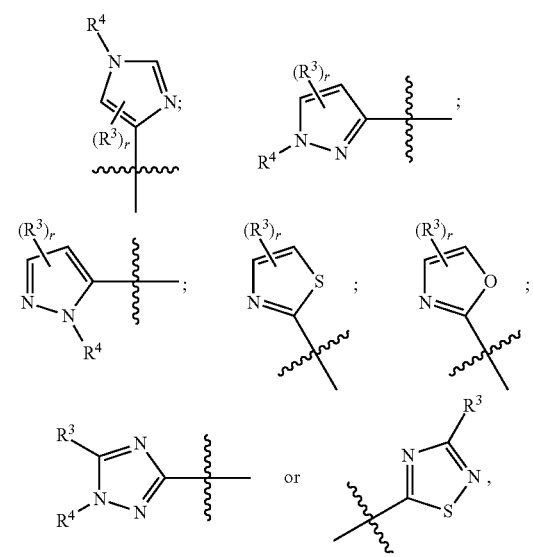

wherein each $R^3$ is independently hydrogen, halo, alkyl, cyano, haloalkyl, cycloalkyl, cycloalkylalkyl, hydroxy or alkoxy; r is 1 or 2; and each $R^4$ is independently hydrogen, or alkyl.

In one embodiment, A is

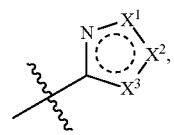

wherein $X^1$, $X^2$ and $X^3$ are selected from (i) and (ii) as follows
(i) $X^1$ is $NR^4$, $X^2$ is $CR^3$ and $X^3$ is CH;
(ii) $X^1$ is $CR^3$, $X^2$ is $NR^4$ and $X^3$ is $CR^3$;
(iii) $X^1$ is $CR^3$, $X^2$ is S or O and $X^3$ is $CR^3$;
(iv) $X^1$ is $CR^3$, $X^2$ is $CR^3$ and $X^3$ is S, O or N; or
(v) $X^1$ is $CR^3$, $X^2$ is N and $X^3$ is S, O or N; and the other variables are as described elsewhere herein.

In one embodiment, A is

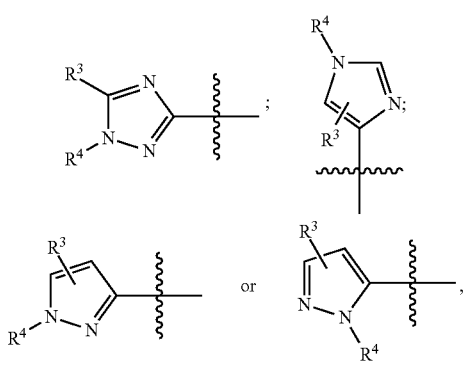

wherein each $R^3$ is independently hydrogen, halo, alkyl, haloalkyl, deuteroarlkyl, hydroxy or alkoxy; and each $R^4$ is independently hydrogen, or alkyl.

In one embodiment, A is

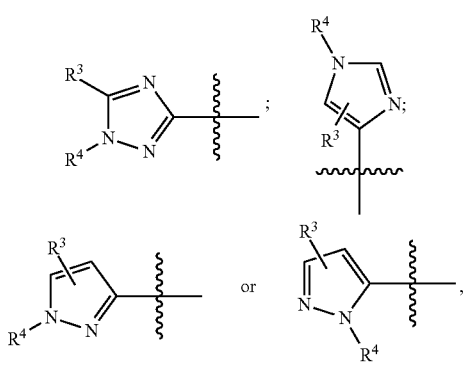

wherein each $R^3$ is independently hydrogen, halo, alkyl, hydroxy or alkoxy; and each $R^4$ is independently hydrogen, or alkyl.

In one embodiment, A is

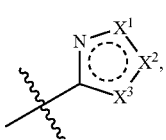

wherein $X^1$, $X^2$ and $X^3$ are selected from (i) and (ii) as follows
(vi) $X^1$ is $NR^4$, $X^2$ is $CR^3$ and $X^3$ is CH; and
(vii) $X^1$ is CH, $X^2$ is $CR^3$ and $X^3$ is S,
and the other variables are as described elsewhere herein.
In one embodiment, A is

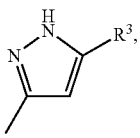

where $R^3$ is alkyl, haloalkyl, deuteroalkyl, alkoxy or haloalkoxy. In one embodiment, A is

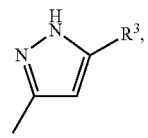

where $R^3$ is hydrogen or alkyl. In one embodiment, $R^3$ is hydrogen or methyl.

In one embodiment, $A^1$ is CH and $A^2$ is N. In one embodiment, $A^1$ is N and $A^2$ is CH. In one embodiment, $A^1$ is N and $A^2$ is N.

In one embodiment, $R^1$ and $R^2$ together form =O.

In one embodiment, $R^1$ and $R^2$ are both halo. In one embodiment, $R^1$ and $R^2$ are both fluoro.

In one embodiment, $R^1$ is hydrogen or alkyl, and $R^2$ is hydroxy. In one embodiment, $R^1$ is hydrogen or methyl, and $R^2$ is hydroxy.

In one embodiment, $R^1$ and $R^2$, together with the carbon atom to which they are attached, form cycloalkyl or heterocyclyl wherein the cycloalkyl is substituted with one or more, in one embodiment, one to four, in one embodiment, one to three, in one embodiment, one or two, substitutents selected from halo, deutero, alkyl, cycloalkyl, heterocyclyl, aryl, heteroaryl, cyano, =O, =N—$OR^{21}$, —$R^xOR^{21}$, —$R^xN(R^{22})_2$, —$R^xS(O)_qR^{23}$, —$C(O)R^{21}$, —$C(O)OR^{21}$ and —$C(O)N(R^{22})_2$ and wherein the heterocyclyl contains not more than two heteroatoms wherein the first heteroatom is selected from O, $NR^{24}$, S, S(O) and $S(O)_2$ and the second optional heteroatom is selected from $NR^{24}$, S, S(O) and $S(O)_2$.

In one embodiment, $R^3$ is hydrogen, alkyl or alkoxy. In another embodiment, $R^3$ is hydrogen, alkyl, haloalkyl, deuteroalkyl, deutero or alkoxy. In another embodiment, $R^3$ is alkyl, haloalkyl, deuteroalkyl, deutero or alkoxy. In another embodiment, $R^3$ is alkyl, haloalkyl or deuteroalkyl. In another embodiment, $R^3$ is hydrogen, alkyl, haloalkyl, deuteroalkyl or deutero. In one embodiment, $R^3$ is hydrogen, deutero or alkyl. In another embodiment, $R^3$ is hydrogen or methyl. In another embodiment, $R^3$ is hydrogen. In one embodiment, $R^4$ is hydrogen. In one embodiment, $R^5$ is hydrogen.

In one embodiment, each $R^6$ is independently selected from deutero, halo, cyano, nitro, alkyl, alkenyl, haloalkyl, hydroxyalkyl, alkoxyalkyl, cycloalkyl, alkoxy, haloalkoxy, aryl, haloaryl, heterocyclyl, heterocyclylalkyl, heterocyclylalkoxy, —$R^xOR^{18}$, —$R^xNR^{19}R^{20}$, —$R^xC(O)NR^yR^z$, —$R^xS(O)_qR^v$, where $R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino; $R^x$ is independently alkylene or a direct bond; $R^v$ is hydrogen, or alkyl; $R^y$ and $R^z$ are each independently hydrogen or alkyl; and $R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy.

In one embodiment, each $R^6$ is independently selected from deutero, halo, cyano, nitro, alkyl, alkenyl, haloalkyl, hydroxyalkyl, alkoxyalkyl, cycloalkyl, aryl, haloaryl, heterocyclyl, heterocyclylalkyl, —$R^xNR^{19}R^{20}$, —$R^xC(O)NR^yR^z$, —$R^xS(O)_qR^v$, where $R^x$ is independently alkylene or a direct bond; $R^v$ is hydrogen, or alkyl; $R^y$ and $R^z$ are each independently hydrogen or alkyl; and $R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy.

In one embodiment, each $R^6$ is independently selected from deutero, cyano, halo, alkyl, alkoxy, haloalkoxy, and cycloalkyl. In one embodiment, each $R^6$ is independently selected from deutero, cyano, halo, alkyl, and cycloalkyl.

In one embodiment, each $R^6$ is independently selected from cyano, fluoro, bromo, chloro, methyl, methoxy, and cyclopropyl.

In one embodiment, $R^{6c}$ is deutero, cyano, halo, alkyl, haloalkoxy, alkoxy or cycloalkyl. In one embodiment, $R^{6c}$ is cyano, bromo, methoxy or cyclopropyl. In one embodiment, $R^{6d}$ is fluoro, chloro or methyl.

In one embodiment, $R^7$ is halo. In one embodiment, $R^7$ is fluoro.

In one embodiment, p is 1 or 2. In one embodiment, p is 1.

In certain embodiments, provided herein are compounds of formula (IX)

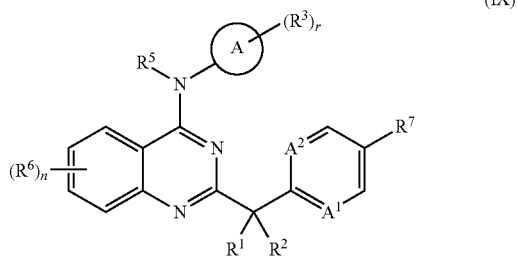

or pharmaceutically acceptable salts, solvates or hydrates thereof, where the variables are as described elsewhere herein. In certain embodiments, provided herein are compounds of formula (IX), wherein A is azolyl;

$A^1$ and $A^2$ are selected from N and CH, such that at least one of $A^1$ or $A^2$ is N;

$R^1$ and $R^2$ are selected as follows:

(i) $R^1$ and $R^2$ together form =O;

(ii) $R^1$ is hydrogen or halo, and $R^2$ is halo; or (iii) $R^1$ is OH; and $R^2$ is hydrogen, or alkyl;

$R^3$ is hydrogen, alkyl, cycloalkyl or alkoxy;

$R^4$ and $R^5$ are each independently hydrogen or alkyl;

each $R^6$ is independently selected from deutero, halo, cyano, nitro, alkyl, alkenyl, haloalkyl, hydroxyalkyl, alkoxyalkyl, cycloalkyl, haloalkoxy, alkoxy, aryl, haloaryl, heterocyclyl, heterocyclylalkyl, heterocyclylalkoxy, —$R^xOR^{18}$, —$R^xNR^{19}R^{20}$, —$R^xC(O)NR^yR^z$, —$R^xS(O)_qR^v$, where $R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^7$ is halo;

$R^x$ is independently alkylene or a direct bond;

$R^v$ is hydrogen, or alkyl;

$R^y$ and $R^z$ are each independently hydrogen or alkyl;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy n is 0 or 1;

r is 1-3; and p is 1.

In certain embodiments, provided herein are compounds of formula (IX), wherein $R^6$ is selected from deutero, halo, cyano, alkyl, haloalkyl, haloalkoxy and alkoxy, and the other variables are as described elsewhere herein.

In certain embodiments, provided herein are compounds of formula (Xa), (Xb) or (Xc),

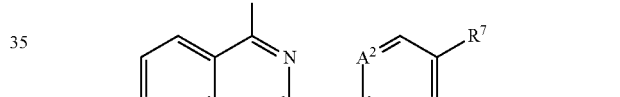

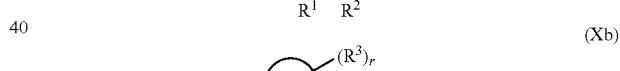

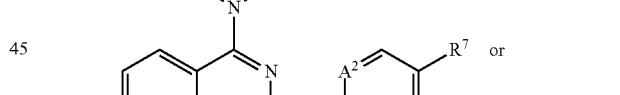

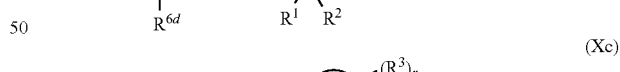

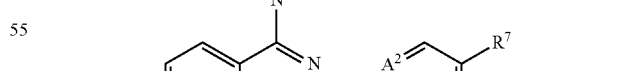

or pharmaceutically acceptable salts, solvates or hydrates thereof, where the variables are as described elsewhere herein. In one embodiment, $R^7$ is fluoro.

In certain embodiments, provided herein are compounds of formula (XIa), (XIb) or (XIc),

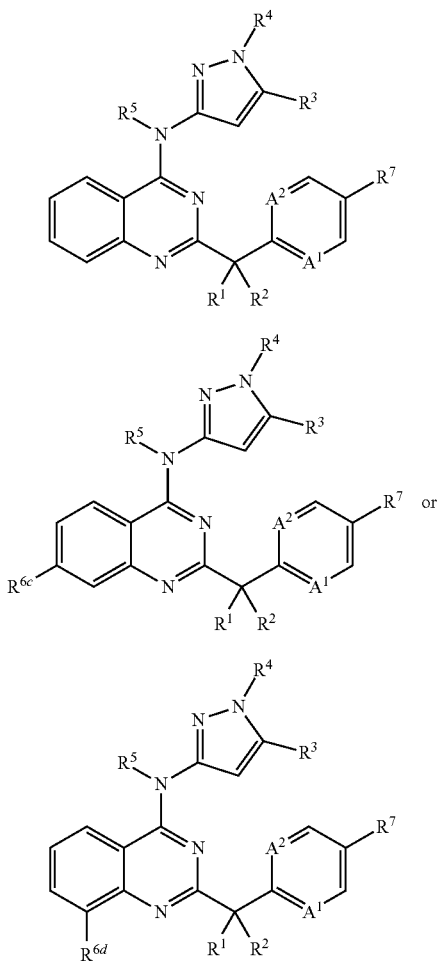

(XIa)

(XIb)

(XIc)

or pharmaceutically acceptable salts, solvates or hydrates thereof, where the variables are as described elsewhere herein. In certain embodiments, provided herein are compounds of formula (XIa), (XIb) or (XIc), wherein $A^1$ and $A^2$ are selected from N and CH, such that at least one of $A^1$ or $A^2$ is N;

$R^1$ and $R^2$ are selected as follows:
(i) $R^1$ and $R^2$ together form =O;
(ii) $R^1$ is hydrogen or halo, and $R^2$ is halo; or
(iii) $R^1$ is OH; and $R^2$ is hydrogen, or alkyl;

$R^3$ is hydrogen, alkyl or alkoxy;

$R^4$ and $R^5$ are each independently hydrogen or alkyl;

$R^{6c}$ and $R^{6d}$ are each independently selected from deutero, halo, cyano, nitro, alkyl, alkenyl, haloalkyl, hydroxyalkyl, alkoxyalkyl, cycloalkyl, alkoxy, haloalkoxy, aryl, haloaryl, heterocyclyl, heterocyclylalkyl, heterocyclylalkoxy, $-R^xOR^{18}$, $-R^xNR^{19}R^{20}$, $-R^xC(O)NR^yR^z$, $-R^xS(O)_qR^v$, where $R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^x$ is independently alkylene or a direct bond;

$R^v$ is hydrogen, or alkyl;

$R^y$ and $R^z$ are each independently hydrogen or alkyl;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy; and $R^7$ is halo.

In certain embodiments, provided herein are compounds of formula (XIa), (XIb) or (XIc), wherein $R^{6d}$ is selected from deutero, halo, cyano, alkyl, haloalkyl, haloalkoxy and alkoxy; and $R^{6c}$ is selected from deutero, halo, cyano, alkyl, haloalkyl, haloalkoxy and alkoxy; and the other variables are as described elsewhere herein.

In certain embodiments, provided herein are compounds of formula (XIIa), (XIIb) or (XIIc),

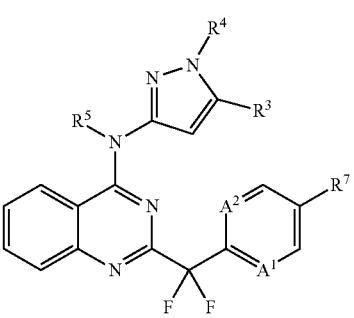

(XIIa)

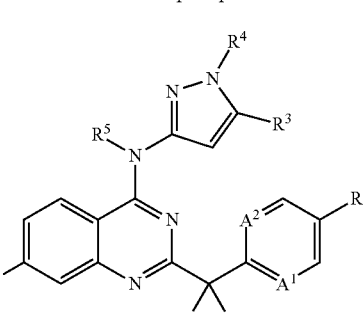

(XIIb)

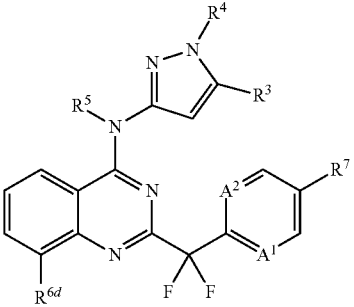

(XIIc)

or pharmaceutically acceptable salts, solvates or hydrates thereof, where the variables are as described elsewhere herein. In certain embodiments, provided herein are compounds of formula (XIIa), (XIIb) or (XIIc), wherein $A^1$ is N, and $A^2$ is CH and the other variables are as described elsewhere herein. In certain embodiments, provided herein are compounds of formula (XIa), (XIb) or (XIc), wherein $A^1$ and $A^2$ are selected from N and CH, such that at least one of $A^1$ or $A^2$ is N;

R³ is hydrogen, alkyl or alkoxy;

R⁴ and R⁵ are each independently hydrogen or alkyl;

R$^{6c}$ and R$^{6d}$ are each independently selected from deutero, halo, cyano, nitro, alkyl, alkenyl, haloalkyl, hydroxyalkyl, alkoxyalkyl, cycloalkyl, alkoxy, haloalkoxy, aryl, haloaryl, heterocyclyl, heterocyclylalkyl, heterocyclylalkoxy, —R$^x$OR$^{18}$, —R$^x$NR$^{19}$R$^{20}$, —R$^x$C(O)NR$^y$R$^z$, —R$^x$S(O)$_q$R$^v$, where R$^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein R$^{18}$ is optionally substituted with 1 to 3 groups Q¹, each Q¹ independently selected from alkyl, hydroxyl, halo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

R$^x$ is independently alkylene or a direct bond;

R$^v$ is hydrogen, or alkyl;

R$^y$ and R$^z$ are each independently hydrogen or alkyl;

R$^{19}$ and R$^{20}$ are selected as follows:

(i) R$^{19}$ and R$^{20}$ are each independently hydrogen or alkyl; or (ii) R$^{19}$ and R$^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy; and R⁷ is halo.

In certain embodiments, provided herein are compounds of formula (XIIa), (XIIb) or (XIIc), wherein R$^{6d}$ is selected from deutero, halo, cyano, alkyl, haloalkyl, alkoxy and haloalkoxy; and R$^{6c}$ is selected from deutero, halo, cyano, alkyl, haloalkyl, haloalkoxy and alkoxy, and the other variables are as described elsewhere herein.

In one embodiment, provided herein is a compound selected from (5-fluoropyridin-2-yl)(4-((5-methyl-1H-pyrazol-3-yl)amino)quinazolin-2-yl)methanone;

2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-N-(5-methyl-1H-pyrazol-3-yl)quinazolin-4-amine;

2-(difluoro(5-fluoropyrimidin-2-yl)methyl)-N-(5-methyl-1H-pyrazol-3-yl)quinazolin-4-amine;

2-(difluoro(5-fluoropyridin-2-yl)methyl)-N-(1H-pyrazol-3-yl)quinazolin-4-amine;

N-(2-(difluoro(5-fluoropyridin-2-yl)methyl)quinazolin-4-yl)-5-methylthiazol-2-amine;

2-(difluoro(5-fluoropyridin-2-yl)methyl)-N-(1H-1,2,4-triazol-3-yl)quinazolin-4-amine;

2-(difluoro(5-fluoropyridin-2-yl)methyl)-N-(5-methoxy-1H-pyrazol-3-yl)quinazolin-4-amine;

2-(difluoro(5-fluoropyridin-2-yl)methyl)-7-methoxy-N-(5-methyl-1H-pyrazol-3-yl)quinazolin-4-amine;

7-bromo-2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-8-methyl-N-(5-methyl-1H-pyrazol-3-yl)quinazolin-4-amine;

8-bromo-2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-8-fluoro-N-(5-methyl-1H-pyrazol-3-yl)quinazolin-4-amine;

7-cyclopropyl-2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-4-((5-methyl-1H-pyrazol-3-yl)amino)quinazoline-7-carbonitrile;

8-chloro-2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-7-methyl-N-(5-methyl-1H-pyrazol-3-yl)quinazolin-4-amine;

2-(difluoro(5-fluoropyridin-2-yl)methyl)-7-fluoro-N-(5-methyl-1H-pyrazol-3-yl)quinazolin-4-amine; and 7-chloro-2-(difluoro(5-fluoropyridin-2-yl)methyl)-N-(5-methyl-1H-pyrazol-3-yl)quinazolin-4-amine, or pharmaceutically acceptable salts, solvates or hydrates thereof.

In one embodiment, provided herein is a compound selected from 2-(difluoro(5-fluoropyridin-2-yl)methyl)-N-(5-methyl-1H-pyrazol-3-yl)-8-(trifluoromethyl)quinazolin-4-amine;

2-(difluoro(5-fluoropyridin-2-yl)methyl)-N-(5-methyl-1H-pyrazol-3-yl)-8-(trifluoromethoxy)quinazolin-4-amine;

2-(difluoro(5-fluoropyridin-2-yl)methyl)-4-((5-methyl-1H-pyrazol-3-yl)amino)quinazoline-8-carbonitrile;

2-(difluoro(5-fluoropyridin-2-yl)methyl)-8-ethyl-N-(5-methyl-1H-pyrazol-3-yl)quinazolin-4-amine;

2-(difluoro(5-fluoropyridin-2-yl)methyl)-N-(5-methyl-1H-pyrazol-3-yl)-8-(methylsulfonyl)quinazolin-4-amine;

2-(difluoro(5-fluoropyridin-2-yl)methyl)-N-(5-methyl-1H-pyrazol-3-yl)-7-(methylsulfonyl)quinazolin-4-amine;

2-(difluoro(5-fluoropyridin-2-yl)methyl)-4-((5-methyl-1H-pyrazol-3-yl)amino)quinazoline-8-carboxamide;

8-chloro-2-(difluoro(5-fluoropyrimidin-2-yl)methyl)-N-(5-methyl-1H-pyrazol-3-yl)quinazolin-4-amine;

2-(difluoro(5-fluoropyridin-2-yl)methyl)-4-((5-methyl-1H-pyrazol-3-yl)amino)quinazoline-7-carboxamide;

4-(2-(difluoro(5-fluoropyridin-2-yl)methyl)-4-((5-methyl-1H-pyrazol-3-yl)amino)quinazolin-8-yl)morpholin-3-one;

2-(difluoro(5-fluoropyridin-2-yl)methyl)-8-methoxy-N-(5-methyl-1H-pyrazol-3-yl)quinazolin-4-amine;

N-(2-(difluoro(5-fluoropyridin-2-yl)methyl)-4-((5-methyl-1H-pyrazol-3-yl)amino)quinazolin-8-yl)formamide;

2-(difluoro(5-fluoropyridin-2-yl)methyl)-4-((5-methyl-1H-pyrazol-3-yl)amino)-N-(oxetan-3-yl)quinazoline-8-carboxamide;

2-(difluoro(5-fluoropyridin-2-yl)methyl)-4-((5-methyl-1H-pyrazol-3-yl)amino)quinazolin-8-ol;

methyl 2-(difluoro(5-fluoropyridin-2-yl)methyl)-4-((5-methyl-1H-pyrazol-3-yl)amino)quinazoline-8-carboxylate;

N-(2-(difluoro(5-fluoropyridin-2-yl)methyl)-4-((5-methyl-1H-pyrazol-3-yl)amino)quinazolin-8-yl)acetamide;

2-(difluoro(5-fluoropyridin-2-yl)methyl)-N-(5-methyl-1H-pyrazol-3-yl)-8-nitroquinazolin-4-amine;

2-(difluoro(5-fluoropyridin-2-yl)methyl)-N4-(5-methyl-1H-pyrazol-3-yl)quinazoline-4,8-diamine;

8-cyclopropyl-2-(difluoro(5-fluoropyridin-2-yl)methyl)-N-(5-methyl-1H-pyrazol-3-yl)quinazolin-4-amine;

N-(2-(difluoro(5-fluoropyridin-2-yl)methyl)-4-((5-methyl-1H-pyrazol-3-yl)amino)quinazolin-8-yl)methanesulfonamide; and 2-(difluoro(5-fluoropyridin-2-yl)methyl)-4-((5-methyl-1H-pyrazol-3-yl)amino)quinazoline-8-carboxylic acid;

or pharmaceutically acceptable salts, solvates or hydrates thereof.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589

(1987); Zello et. al., *Metabolism,* 43: 487 (1994); Gately et. al., *J. Nucl. Med.,* 27: 388 (1986); and Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., *Adv. Drug Res., vol.* 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

C. FORMULATION OF PHARMACEUTICAL COMPOSITIONS

Provided herein are pharmaceutical compositions comprising a compound provided herein, e.g., a compound of Formula I, as an active ingredient, or a pharmaceutically acceptable salt, solvate or hydrate thereof; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Deliver Technology,* Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, e.g., a compound of Formula I, or a pharmaceutically acceptable salt, solvate or hydrate thereof; and one or more pharmaceutically acceptable excipients or carriers.

In another embodiment, the pharmaceutical compositions are provided in a dosage form for parenteral administration, which comprise a compound provided herein, e.g., a compound of Formula I, or a pharmaceutically acceptable salt, solvate or hydrate thereof; and one or more pharmaceutically acceptable excipients or carriers.

In yet another embodiment, the pharmaceutical compositions are provided in a dosage form for topical administration, which comprise a compound provided herein, e.g., a compound of Formula I, or a pharmaceutically acceptable salt, solvateor hydrate thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Oral Administration

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained, pulsed-, controlled, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

D. EVALUATION OF THE ACTIVITY OF THE COMPOUNDS

Standard physiological, pharmacological and biochemical procedures are available for testing the compounds to identify those that possess biological activities that modulate the activity of JAK kinases, including wild type and mutant JAK kinases. Such assays include, for example, biochemical assays such as binding assays, see Fabian et al., *Nature Biotechnology* 2005, 23, 329-336, radioactivity incorporation assays, as well as a variety of cell based assays.

Exemplary cell based assay methodologies include measurement of STAT5A phosphorylation, for example, by ELISA or the measurement of proliferation in leukemic cell lines such as TF-1 or HEL-2, for example, by BrdU incorporation, by fluorescent staining or by a reporter assay activated by the transcription factor STATS. Cells useful in the assays include cells with wildtype JAK such as TF-1 or mutated JAK such as the cell line HEL-2 which express a constitutively active JAK2 carrying the V617F mutation. Suitable cells include those derived through cell culture from patient samples as well as cells derived using routine molecular biology techniques, e.g., retroviral transduction, transfection, mutagenesis, etc.

E. METHODS OF USE OF THE COMPOUNDS AND COMPOSITIONS

Also provided herein are methods of using the disclosed compounds and compositions, or pharmaceutically acceptable salts, solvates or hydrates thereof, for the treatment, prevention, or amelioration of a disease or disorder that is mediated or otherwise affected via JAK kinase, including JAK2 kinase activity or one or more symptoms of diseases or disorders that are mediated or otherwise affected via JAK kinase, including JAK2 kinase, activity. JAK kinase can be wild type and/or mutant form of JAK2 kinase. Consistent with the description above, such diseases or disorders include without limitation: myeloproliferative disorders such as polycythemia vera (PCV), essential thrombocythemia and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain tumor, pancreatic cancer and renal carcinoma; and inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD) and dry eye syndrome (or keratoconjunctivitis sicca (KCS)).

In certain embodiments, provided herein are methods of using the disclosed compounds and compositions, or pharmaceutically acceptable salts, solvates or hydrates thereof, for the treatment, prevention, or amelioration of a disease or disorder selected from myeloproliferative disorders such as polycythemia vera (PCV), essential thrombocythemia and idiopathic myelofibrosis (IMF) and hypereosinophilic syndrome (HES); leukemia such as myeloid leukemia including chronic myeloid leukemia (CML), imatinib-resistant forms of CML, acute myeloid leukemia (AML), acute lymphoblastic leukemia (ALL) and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, melanoma; and inflammatory diseases or disorders related to immune dysfunction, immunodeficiency or immunomodulation, such as tissue transplant rejection, graft-versus-host disease, wound healing, kidney disease including diabetic neuropathy; autoimmune diseases such as multiple sclerosis, thyroiditis, type 1 diabetes, sarcoidosis, psoriasis, allergic rhinitis, atopic dermatitis, myasthenia gravis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), inflammatory diseases of the eye including conjunctivitis, uveitis, iritis, scleritis, inflammatory diseases of the respiratory tract including the upper respiratory tract such as rhinitis and sinusitis and inflammatory diseases of the lower respiratory tract including bronchitis; inflammatory myopathy such as myocarditis, other inflammatory diseases such as ischemia reperfusion injuries related to an inflammatory ischemic event such as a stroke or cardiac arrest, and other inflammatory conditions such as systemic inflammatory response syndrome (SIRS) and sepsis.

In certain embodiments, JAK-mediated diseases and disorders include restenosis, fibrosis and scleroderma. In certain embodiments, JAK-mediated diseases include viral diseases such as Epstein Barr virus (EBV), hepatitis (hepatitis B or hepatitis C), human immunodeficiency virus (HIV), Human T-lymphotropic virus type 1 (HTLV-1), varicella-zoster virus and the human papilloma virus (HPV).

In certain embodiments, the compounds provided herein are modulators of the activity of an adenosine $A_3$ receptor. In certain embodiments, the compounds provided herein are useful in preventing, treating, or ameliorating one or more symptoms of an adenosine $A_3$-mediated condition, disorder, or disease. Further provided herein is a method of modulating the activity of an adenosine $A_3$ receptor, comprising contacting the adenosine $A_3$ receptor with an effective amount of a compound of Formula (I), or a pharmaceutically acceptable salt, solvate, or prodrug thereof.

In certain embodiments, adenosine $A_3$-mediated diseases and disorders include restenosis, fibrosis and scleroderma. In certain embodiments, adenosine $A_3$-mediated diseases include viral diseases such as Epstein Barr virus (EBV), hepatitis (hepatitis B or hepatitis C), human immunodeficiency virus (HIV), Human T-lymphotropic virus type 1 (HTLV-1), varicella-zoster virus and the human papilloma virus (HPV).

In certain embodiments, the adenosine $A_3$-mediated condition, disorder, or disease is a cardiovascular disease, including, but not limited to, ischaemic heart disease. In certain embodiments, the adenosine $A_3$-mediated condition, disorder, or disease is atherosclerosis. In certain embodiments, the adenosine $A_3$-mediated condition, disorder, or disease is lung injury. In certain embodiments, the adenosine $A_3$-mediated condition, disorder, or disease is renal failure. In certain embodiments, the adenosine $A_3$-mediated condition, disorder, or disease is an eye disease, including, but not limited to, glaucoma and ocular hypertension. In certain embodiments, the adenosine $A_3$-mediated condition, disorder, or disease is glaucoma or ocular hypertension.

In certain embodiments, provided herein is a method of down regulating the activity of an adenosine $A_3$ receptor, comprising contacting the adenosine $A_3$ receptor with an effective amount of a compound of formula I, or a pharmaceutically acceptable salt, solvate, or prodrug thereof.

F. COMBINATION THERAPY

Furthermore, it will be understood by those skilled in the art that the compounds, isomers, and pharmaceutically acceptable salts, solvates or hydrates provided herein, including pharmaceutical compositions and formulations containing these compounds, can be used in a wide variety of combination therapies to treat the conditions and diseases described above. Thus, also contemplated herein is the use of compounds, isomers and pharmaceutically acceptable salts, solvates or hydrates provided herein in combination with other active pharmaceutical agents for the treatment of the disease/conditions described herein.

In one embodiment, such additional pharmaceutical agents include without limitation anti-cancer agents, including chemotherapeutic agents and anti-proliferative agents; anti-inflammatory agents and immunomodulatory agents or immunosuppressive agents.

In certain embodiments, the anti-cancer agents include anti-metabolites (e.g., 5-fluoro-uracil, cytarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment.

In certain embodiments, the anti-inflammatory agents include methotrexate, matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, or glucocorticoid receptor agonists such as corticosteroids, methylprednisone, prednisone, or cortisone.

The compound or composition provided herein, or pharmaceutically acceptable salts, solvates or hydrates thereof, may be administered simultaneously with, prior to, or after administration of one or more of the above agents.

Pharmaceutical compositions containing a compound provided herein or pharmaceutically acceptable salts, solvates or hydrates thereof, and one or more of the above agents are also provided.

Also provided is a combination therapy that treats or prevents the onset of the symptoms, or associated complications of cancer and related diseases and disorders comprising the administration to a subject in need thereof, of one of the compounds or compositions disclosed herein, or pharmaceutically acceptable salts, solvates or hydrates thereof, with one or more anti-cancer agents.

G. PREPARATION OF COMPOUNDS

Starting materials in the synthesis examples provided herein are either available from commercial sources or via literature procedures (e.g., *March Advanced Organic Chemistry Reactions, Mechanisms, and Structure*, (1992) 4th Ed.; Wiley Interscience, New York). All commercially available compounds were used without further purification unless otherwise indicated. Proton ($^1$H) nuclear magnetic resonance (NMR) spectra were typically recorded at 300 MHz on a Bruker Avance 300 NMR spectrometer unless otherwise noted. Significant peaks are tabulated and typically include: number of protons, and multiplicity (s, singlet; d, double; t, triplet; q, quartet; m, multiplet; br s, broad singlet). Chemical shifts are reported as parts per million ($\delta$) relative to tetramethylsilane. Unless otherwise noted, low resolution mass spectra (MS) were obtained as electrospray ionization (ESI) mass spectra, which were typically recorded on a Shimadzu HPLC/MS instrument using reverse-phase conditions using a mobile phase gradients of either acetonitrile/water containing 0.05% acetic acid or MeOH/water containing 0.2% formic acid. Preparative reverse phase HPLC was typically performed using a Varian HPLC system equipped with a Phenomenex phenylhexyl, a Phenomenex Luna C18, or a Varian Pursuit diphenyl reverse phase column; typical elution conditions utilized a gradient of acetonitrile/water containing 0.05% acetic acid. Silica gel chromatography was either performed manually, typically following the published procedure for flash chromatography (Still et al. (1978) *J. Org. Chem.* 43:2923), or on an automated system (for example, on a Biotage SP instrument) using pre-packed silica gel columns.

It is understood that in the following description, combinations of substituents and/or variables of the depicted formulae are permissible only if such contributions result in stable compounds under standard conditions.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

One of ordinary skill in the art could readily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is E/Z isomers, enantiomers and/or diastereomers.

Compounds of formula (I) may be generally prepared as depicted in the following schemes, and unless otherwise noted, the various substituents are as defined elsewhere herein.

Standard abbreviations and acronyms as defined in *J. Org. Chem.* 2007 72(1): 23A-24A are used herein. Other abbreviations and acronyms used herein are as follows:

| | |
|---|---|
| DCM | Dichloromethane |
| DIEA | Diisopropylethylamine |
| EDCI | N-(3-dimethylaminopropyl)-N'-ethylcarbodiimide hydrochloride |
| EtOAc | ethyl acetate |
| EtOH | Ethanol |
| FBS | fetal bovine serum |
| HATU | O-(7-Azabenzotriazol-1-yl)-N,N,N',N'-tetramethyluronium hexafluorophosphate |
| HOAc | acetic acid |
| HOBt | N-hydroxybenzotriazole |
| MeOH | Methanol |
| TEA | triethylamine |
| Trityl | triphenylmethyl |

Compounds provided herein are synthesized according to the following schemes and descriptions.

As illustrated in Scheme 1, an appropriate anthranilamide derivative 1 can be transformed to a 2-carboxylate substituted quinazoline 2 by treatment with an activated oxalic acid derivative such as a dialkyl oxalate either neat or in a suitable solvent such as EtOH or HOAc with heating as required. Alternatively, 1 is treated with an oxalic acid monoalkyl ester chloride in a suitable solvent such as DCM in the presence of a base such as TEA and optionally in the presence of a catalyst such as DMAP; or 1 is treated with a cyano oxoacetate monoalkyl ester with heating in a suitable solvent such as acetonitrile or DMF in the presence of a base such as TEA. Subsequent treatment under dehydrating conditions, for example, heating with or without TMSCl in the presence of a suitable base such as DIEA in a suitable solvent such as DCE affords the quinazoline 2. Treatment of 2 with an appropriate phosphorous or phosphoryl halide reagent, for example phosphoryl chloride, forms the 4-halo derivative 3. Alternatively, 2 may be treated with a sulfonyl halide to form 3 (X=O-sulfonyl). As a further alternative, 2 may also be transformed into 3 (X=S(O)-alkyl or S(O)$_2$-alkyl) by treatment with Lawesson's reagent or P$_2$S$_5$, followed by alkylation and subsequent oxidation. Treatment of 3 with a metalloarene or metalloheteroarene, for example an aryl or heteroaryl lithium or an aryl or heteroaryl Grignard reagent in a suitable solvent such diethyl ether, THF, or other ether solvent, produces ketone 4. Subsequent conversion of 4 to 5 is accomplished by treatment of 4 with an aminoazole with heating as required in the presence of acid or base or in the presence of a suitable Pd catalyst with added Pd ligands as required.

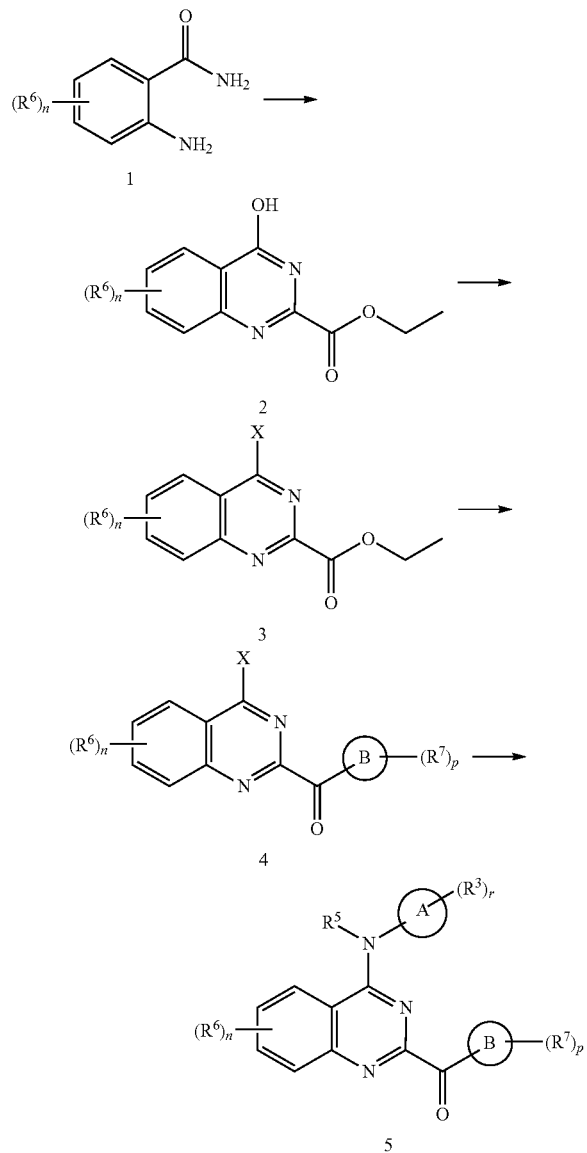

Scheme 1

As illustrated in Scheme 2, anthranilamides 1 may be condensed with a suitably activated carboxylic acid derivative 6 followed by dehydrative cyclization, promoted for example, with heat or with TMSCl in the presence of a tertiary amine base such as TEA, DIEA, or pyridine to form 4-hydroxyquinazoline derivatives 7. Alternatively, heating of 1 with a carboxylic acid (6, Y=OH), or its salt, in the presence of trimethylsilyl polyphosphate affords 7. Treatment of 7 with an appropriate phosphorous or phosphoryl halide reagent, for example phosphoryl chloride, forms the 4-halo derivative 8. Alternatively, 7 may be treated with a sulfonyl halide in the presence of base to form 8 (X=O-sulfonyl). As a further alternative, 7 may also be transformed into 8 (X=S(O)-alkyl or S(O)$_2$-alkyl) by treatment with Lawesson's reagent or P$_2$S$_5$ followed by alkylation and subsequent oxidation. Subsequent conversion of 8 to 9 is accomplished under conditions analogous to those described in Scheme 1 for conversion of 4 to 5.

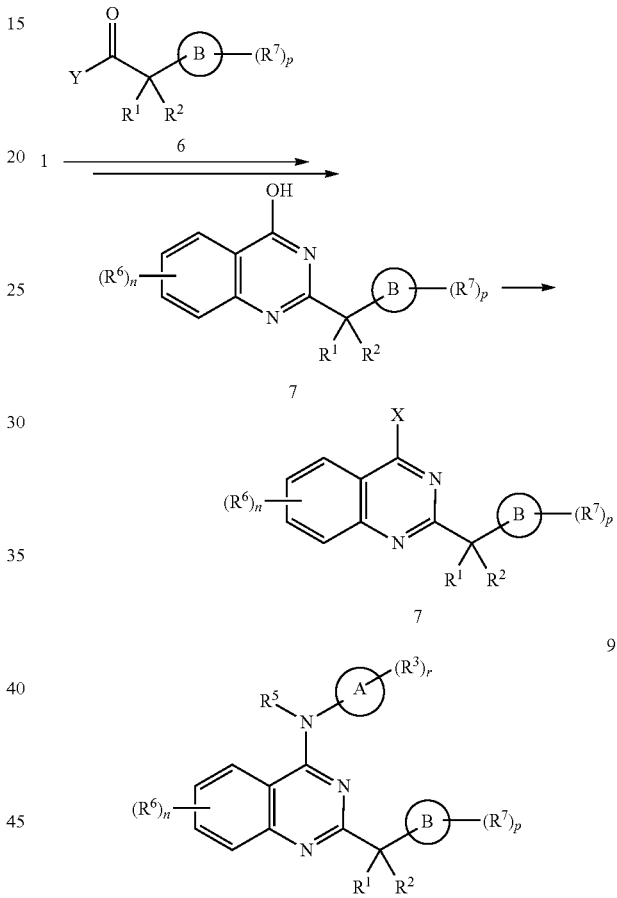

Scheme 2

In Scheme 3 are illustrated representative examples by which the keto group in 5 can be further modified to afford additional compounds of the invention. Treatment of 5 with Lawesson's reagent affords thioketones 10. Treatment of 5 with an amine, hydroxylamine, or alkoxylamine under dehydrating conditions optionally in the presence of acid with heating affords, respectively, imines, oximes, or O-alkyl oximes 11. Treatment of 5 with a Wittig reagent or Horner-Emmons reagent affords olefins 12. Treatment of 5 with a reducing agent such as sodium borohydride or lithium borohydride affords secondary alcohols 13. Treatment of 5 with an organometallic reagent such as a Grignard reagent or an organolithium compound affords tertiary alcohols 14. Heating 5 with an alcohol in the presence of acid with removal of water affords ketals 15. Heating 5 with a 1,2- 1,3- or 1,4-diol in the presence of acid with removal of water affords cyclic ketals 16.

Scheme 3

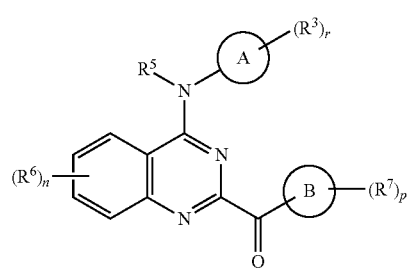
5

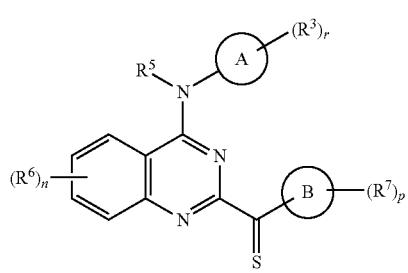
10

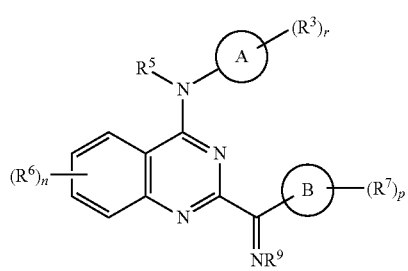
11

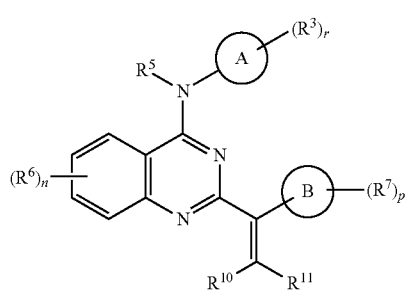
12

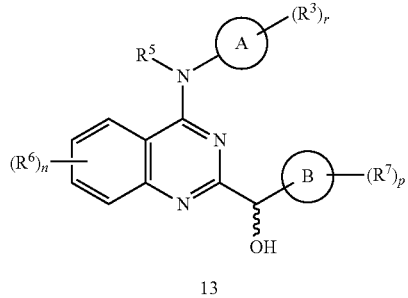
13

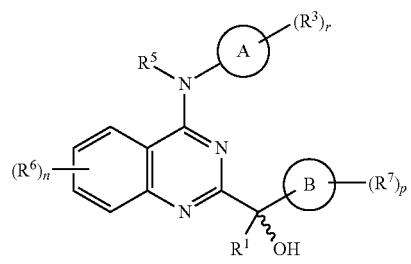
14

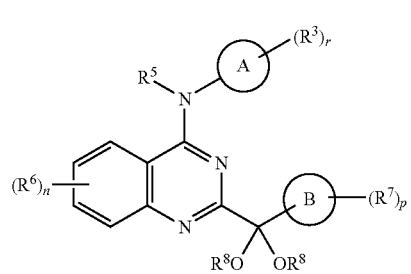
15

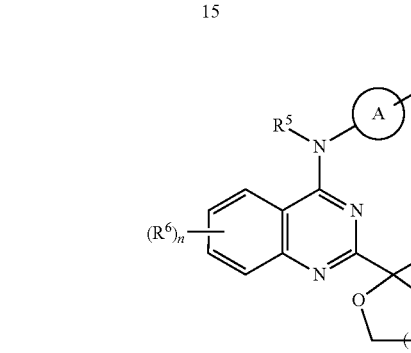
16

In Scheme 4 is illustrated a useful method for preparing acids 6 used in Scheme 2. A carboxylic acid derivative 17, where Y' is for example alkoxy or a subsequently removable chiral auxiliary, is deprotonated at the alpha position with a strong base and treated with an alkylating agent to afford 18. The sequence is repeated with the same or a different alkylating agent to form 19. The Y' group of 19 is then converted by procedures well known in the art to the Y group of 6 that is suitable for use in Scheme 2.

Scheme 4

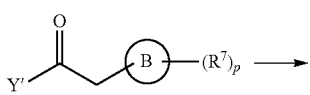
17

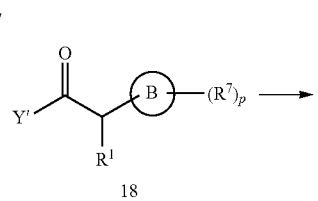
18

-continued

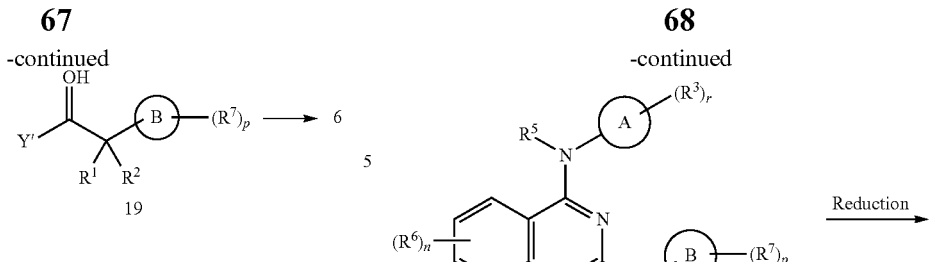

In Scheme 5 is illustrated an alternative method for preparing acids 6 used in Scheme 2. A suitable carboxylic acid derivative, following conversion with base to an enolate 20 or its equivalent is treated with an aryl halide, or more suitably with a heteroaryl halide to form 22. The Y' group of 22 is then converted by procedures well known in the art to the Y group of 6 that is suitable for use in Scheme 2.

Scheme 5

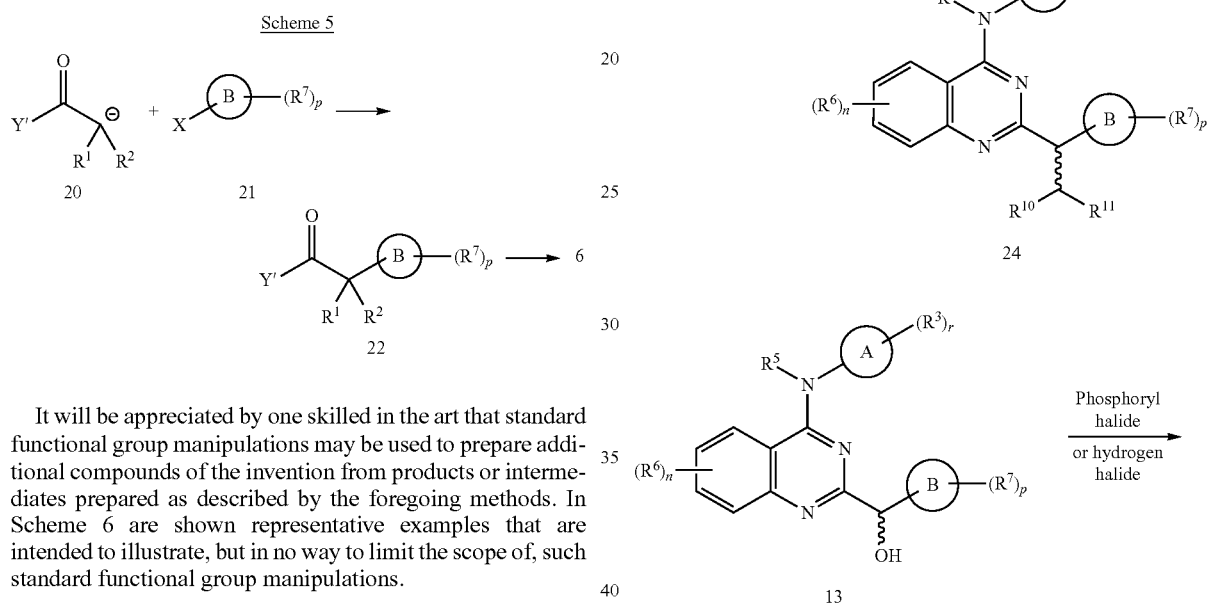

It will be appreciated by one skilled in the art that standard functional group manipulations may be used to prepare additional compounds of the invention from products or intermediates prepared as described by the foregoing methods. In Scheme 6 are shown representative examples that are intended to illustrate, but in no way to limit the scope of, such standard functional group manipulations.

Scheme 6

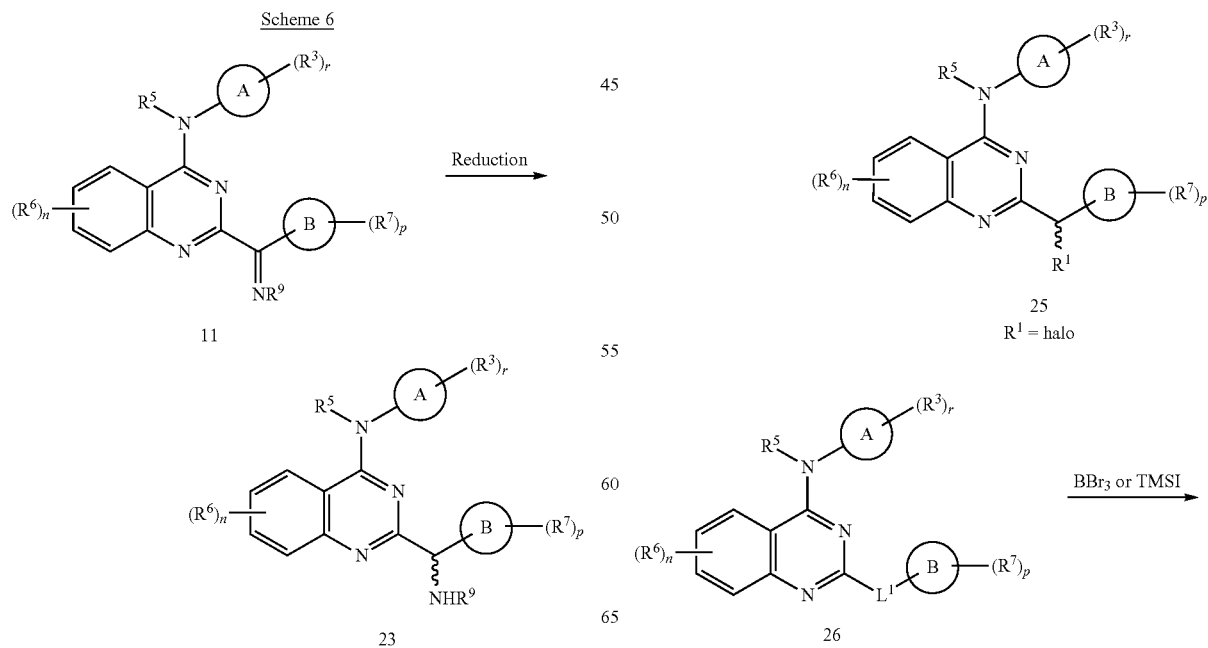

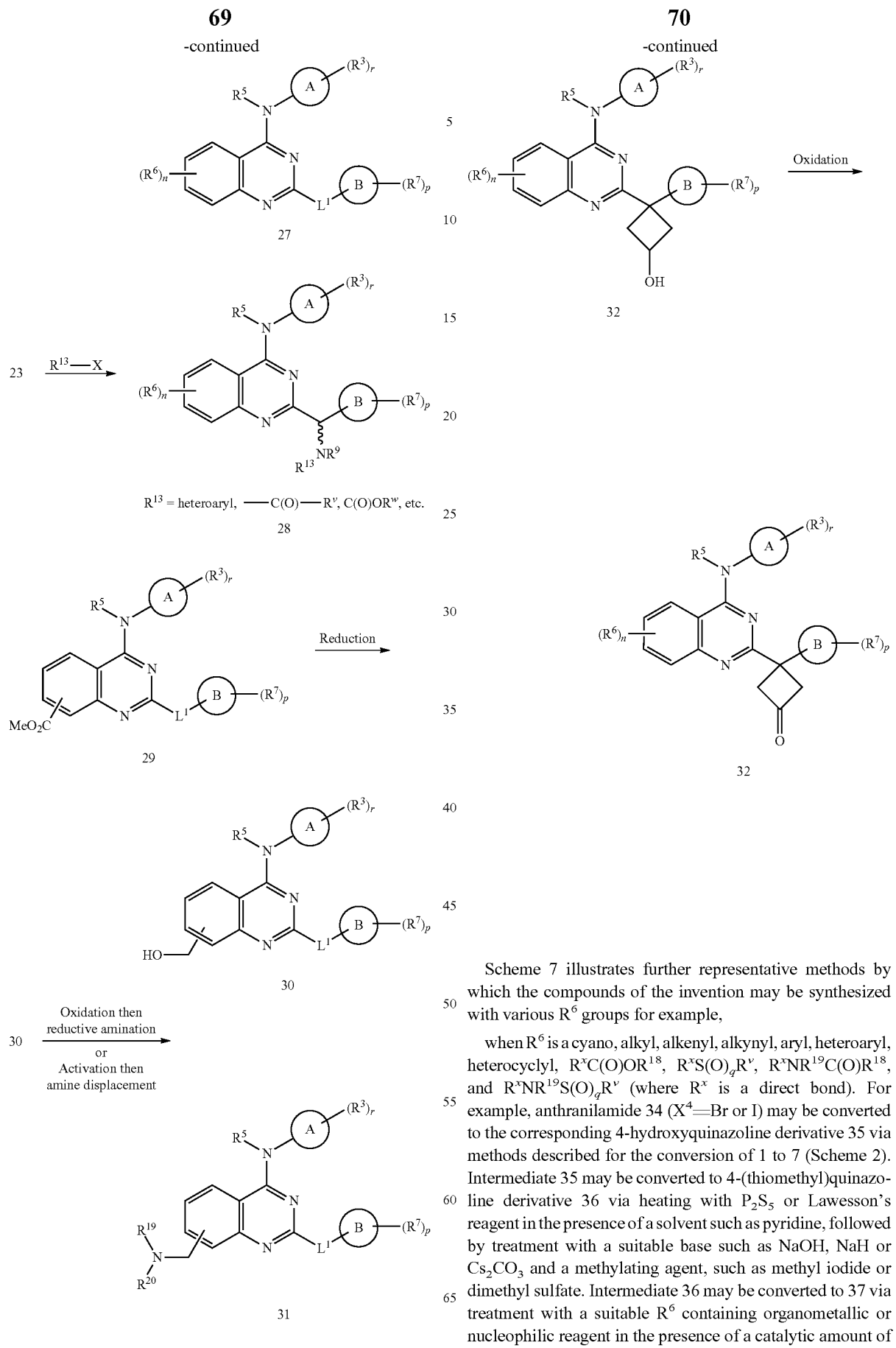

Scheme 7 illustrates further representative methods by which the compounds of the invention may be synthesized with various $R^6$ groups for example, when $R^6$ is a cyano, alkyl, alkenyl, alkynyl, aryl, heteroaryl, heterocyclyl, $R^xC(O)OR^{18}$, $R^xS(O)_qR^v$, $R^xNR^{19}C(O)R^{18}$, and $R^xNR^{19}S(O)_qR^v$ (where $R^x$ is a direct bond). For example, anthranilamide 34 ($X^4$=Br or I) may be converted to the corresponding 4-hydroxyquinazoline derivative 35 via methods described for the conversion of 1 to 7 (Scheme 2). Intermediate 35 may be converted to 4-(thiomethyl)quinazoline derivative 36 via heating with $P_2S_5$ or Lawesson's reagent in the presence of a solvent such as pyridine, followed by treatment with a suitable base such as NaOH, NaH or $Cs_2CO_3$ and a methylating agent, such as methyl iodide or dimethyl sulfate. Intermediate 36 may be converted to 37 via treatment with a suitable $R^6$ containing organometallic or nucleophilic reagent in the presence of a catalytic amount of a suitable organopalladium-complex or a suitable organocopper- or inorganic copper-complex, and optionally in the presence of a suitable phosphine-ligand, and optionally in the presence of a suitable base, and in a suitable solvent at elevated temperature or under microwave conditions. Examples of $R^6$ containing organometallic reagents could include $ZnCN_2$ (where $R^6$=CN), alkyltin reagents or alkylboronic acids and esters (where $R^6$=alkyl), alkenyltin Example bases could include $Cs_2CO_3$, DIEA, and TEA. Intermediates 37 may be converted to the corresponding final derivatives 9 via initial oxidation of the methylsulfide with a suitable oxidizing agent such as meta-chloroperbenzoic acid, followed by treatment with an aminoazole with heating or under microwave conditions as required, and in the presence of an acid or base or in the presence of a suitable palladium catalyst with added palladium ligands, as required.

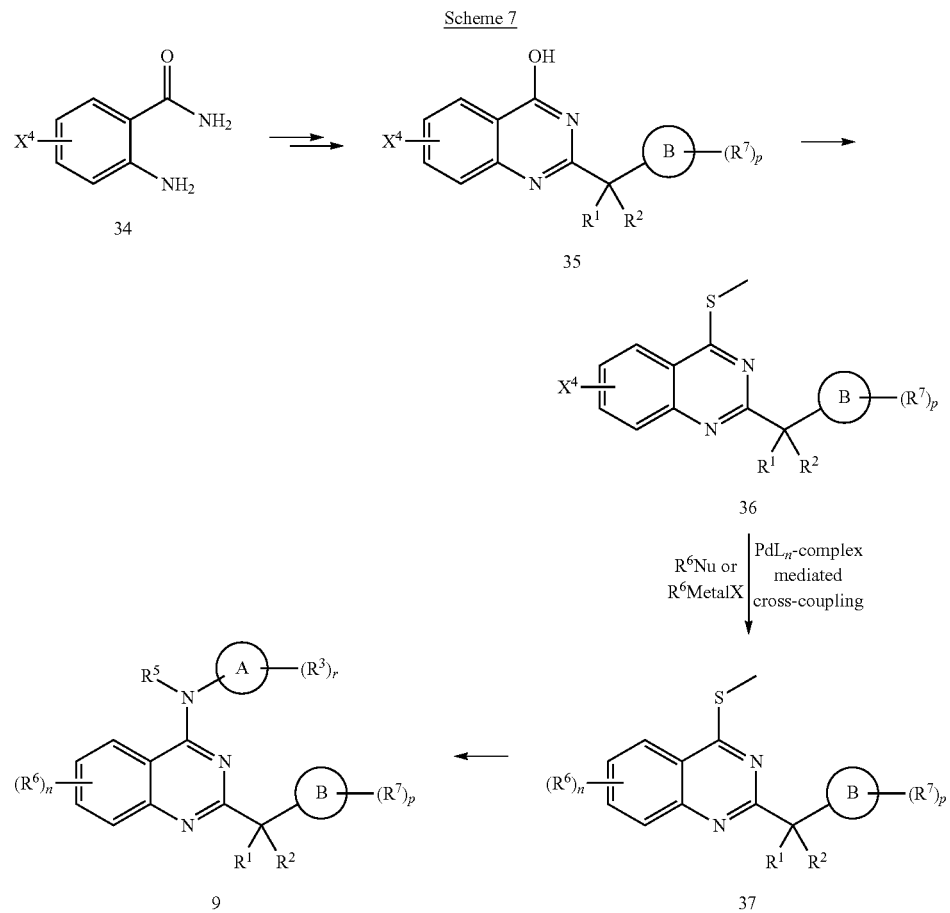

Scheme 7 reagents (where $R^6$=alkenyl), alkynyltin or alkynylsilane reagents (where $R^6$=alkynyl), arylboronic acids or esters or aryltin or arylzinc reagents (where $R^6$=aryl), heteroarylboronic acids or esters or heteroaryltin or heteroarylzinc reagents (where $R^6$=heteroaryl). Examples of $R^6$ containing nucleophilic reagents could include carbon monoxide/ $R^{18}OH$ (where $R^6$=$R^xC(O)OR^{18}$), $R^vSO_2H$ sodium salt (where $R^6$=$R^xS(O)_2R^v$), $N(H)R^{19}C(O)R^{18}$, $N(H)R^{19}C(O)R^{20}$, and $N(H)R^{19}S(O)_qR^v$. Examples of organopalladium-complex reagents could include tetrakis(triphenylphospine)palladium (0), tris(dibenzylideneacetone)dipalladium (0), bis(triphenylphosphino)palladium dichloride, bis(tri-tert-butylphosphine)palladium, and palladium (II) acetate. Examples of organocopper- and inorganic copper-complex reagents could include copper(I) trifluoromethanesulfonate benzene complex, and copper(I) iodide. Example phosphine-ligands could include bis(diphenylphosphino)-9,9'-dimethylxanthene and 1,1'-bis(diphenylphosphino)ferrocene.

Scheme 8 illustrates further representative methods by which the incorporation $R^6$=$R^xNR^{19}C(O)R^{18}$, and $R^xNR^{19}S(O)_qR^v$ (where $R^x$ is a direct bond) may be achieved. Intermediate 36 may be converted to intermediate 38 via treatment with a suitable amino containing reagent (where P=protecting group), such as benzophenone imine, 2,4-dimethoxybenzylamine, or tert-butyl carbamate, and in the presence of a catalytic amount of a suitable organopalladium-complex, and optionally in the presence of a suitable phosphine-ligand, and optionally in the presence of a suitable base, and in a suitable solvent at elevated temperature or under microwave conditions. Conversion of 38 to 39 may be achieved via treatment with a suitable acid such as TFA or aq. HCl. Subsequent conversion of 39 to 37 [where $R^6$=$R^xNR^{19}C(O)R^{18}$, and $R^xNR^{19}S(O)_qR^v$ (where $R^x$ is a direct bond)] may be achieved via treatment with the appropriate acyl halide, sulfinyl halide, or sulfonyl halide, in the presence of a suitable base such as TEA or pyridine. Intermediate 37 may be converted to 9 via methods described in Scheme 7.

Scheme 8

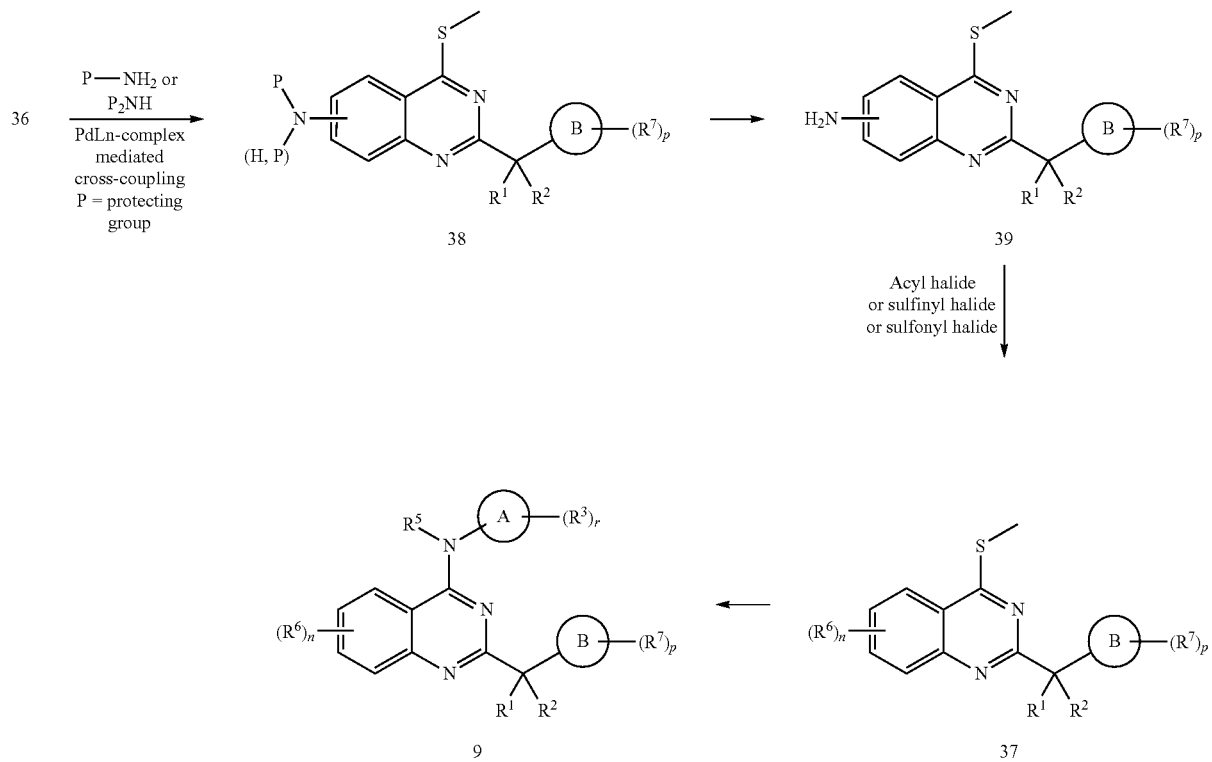

Scheme 9 illustrates a representative method by which preparation of aminoquinazoline derivatives 42 may be achieved. Conversion of 40 to 41 may be achieved employing methods described in Scheme 2. Intermediate 41 may be converted to 42 via treatment with a suitable reducing agent, such as $SnCl_2$, $FeCl_2$, sodium dithionite, or zinc and acetic acid, in a suitable solvent at rt or with heating as required.

Scheme 9

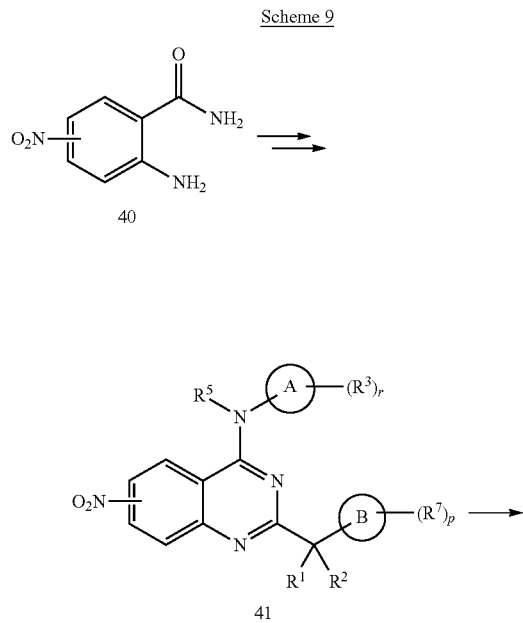

-continued

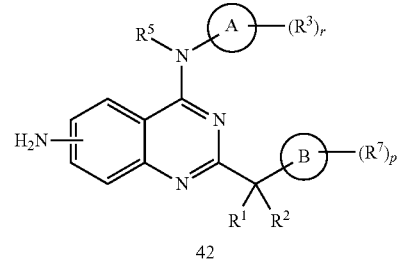

Scheme 10 illustrates representative methods by which preparation of carboxylic acid derivatives 47, and carboxamide derivatives 52 may be achieved. Reaction of (trifluoromethyl)anthranilamides 43 with 6 (Scheme 2) in the presence of trimethylsilyl polyphosphate or polyphosphoric acid, with heating, affords 44. Subsequent treatment of 44 with MeOH and HCl affords 45. Intermediate 45 may be converted to 46 employing methods analogous to those described for the conversion of 7 to 9 (Scheme 2). Treatment of 46 with aq. NaOH or LiOH in a suitable organic solvent at rt or with heating as required, affords carboxylic acid derivatives 47. Alternatively, 47 may be prepared directly from cyano derivative 48 (prepared as described in Scheme 7) via treatment with conc $H_2SO_4$, or aq NaOH at rt or with heating as required. Preparation of carboxamide derivatives 52 may be achieved as follows. Conversion of 45 to 49 may be carried out using methods analogous to those described for the conversion of 35 to 36 (Scheme 7). Subsequent treatment of 49 with aq. NaOH or LiOH in a suitable organic solvent at rt or with heating as required, affords carboxylic acid derivatives 50. Conversion of 50 to carboxamide derivatives 51 may be achieved via treatment with an amine ($R^{19}R^{20}NH$) in the presence of a suitable peptide coupling agent such as O-benzotriazole-N,N,N',N'-tetramethyl-uronium-hexafluoro-phosphate (HBTU) or benzotriazole-1-yl-oxy-tris-(dimethylamino)-phosphonium hexafluorophosphate (BOP), and a suitable base such as TEA or DIEA, and in a suitable organic solvent such as THF or DMF, at rt or heating as required. Conversion of 51 to final derivatives 52 may be carried out using methods analogous to those described for the conversion of 37 to 9 (Scheme 7).

prepared using methods known to those skilled in the art. Scheme 11 illustrates representative methods that may be employed for the preparation of additional aminoazoles or azolyl amines. For example, nitroazoles 53 may be converted to aminoazoles 54 via treatment with a suitable reducing agent such as $SnCl_2$ in a suitable solvent such as DCE or EtOH optionally in the presence of HCl, with heating. Alternatively, treatment of 53 with activated iron or zinc metal in HOAc with heating, will afford 54. Alternatively, treatment of

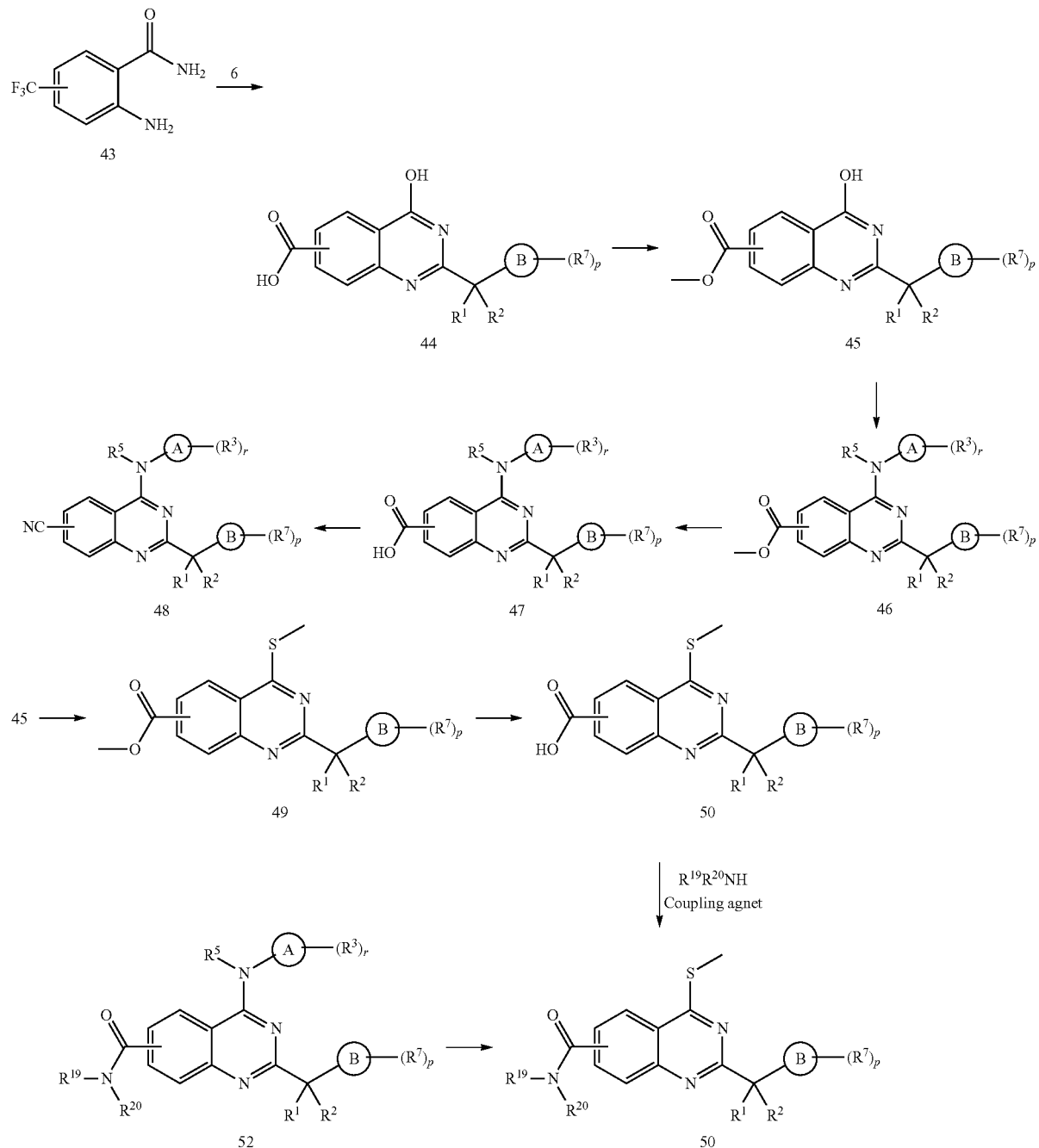

Aminoazole or azolyl amine intermediates employed herein may be obtained either via commercial sources or 53 with palladium metal on activated carbon in the presence of ≥1 atmosphere pressure of hydrogen gas, in a suitable solvent such as MeOH, EtOH, or EtOAc or mixtures of these, at rt or with heating as required, will afford 54. Alternatively treatment of 53 with sodium hydrosulfite in a suitable solvent mixture such as THF and water at rt or with heating as required, will afford 54. Alternatively, aminoazoles 54 may also be obtained from azole carboxylic acids 55 via initial treatment with diphenylphosphoryl azide in the presence of an organic base such as TEA, and in a suitable solvent such as toluene or THF, and with heating from 50° C. to 150° C. as required, followed by hydrolysis. Alternatively, treatment of 55 with diphenylphosphoryl azide in the presence of an organic base such as TEA, and in the presence of excess tert-butanol, and in a suitable solvent such as toluene or THF, and with heating from 50° C. to 150° C. as required, will afford a tert-butylcarbamoyl azole intermediate, which upon treatment with an acid such as TFA or HCl in a suitable solvent, will afford 54. Aminoazoles 54 may also be obtained from azolyl bromides or iodides 56, bearing (as required) suitable protecting groups on any azole ring N—H position, via initial treatment with a suitable amino containing reagent (where P=protecting group), such as benzophenone imine, 2,4-dimethoxybenzylamine, or tert-butyl carbamate, and in the presence of a catalytic amount of a suitable organopalladium-complex, and optionally in the presence of a suitable phosphine-ligand, and optionally in the presence of a suitable base, and in a suitable solvent at elevated temperature or under microwave conditions, to afford intermediate 57. Subsequent N-deprotection of intermediate 57 (including azole ring N-deprotection, where required), employing appropriate methods known to those skilled in the art will afford 54. Conversion of aminoazoles 54 to alkylated aminoazoles 58 may be achieved via treatment of 54 with an appropriate aldehyde or ketone substrate, in the presence of a suitable Lewis acid such as TMSCl or TiCl$_4$ and a suitable reducing agent such as sodium (triacetoxy)borohydride or sodium cyanoborohydride, in a suitable organic solvent such as DCM, DCE, THF, or MeOH, optionally in the presence of HOAc, at rt or with heating as required. Alternatively, 58 may be obtained via treatment of 54 with an alkyl halide in the presence of a suitable organic base such as pyridine or DIEA, and optionally sodium or potassium iodide, and in a suitable solvent such as DMF or THF, at rt or with heating as required. Nitroazoles 53, azole carboxylic acids 55, and azole bromides or iodides 56 may be obtained from commercial sources or prepared using methods known to those skilled in the art.

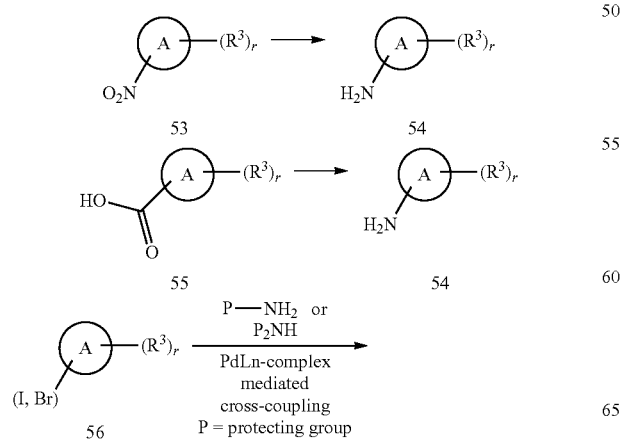

Scheme 11

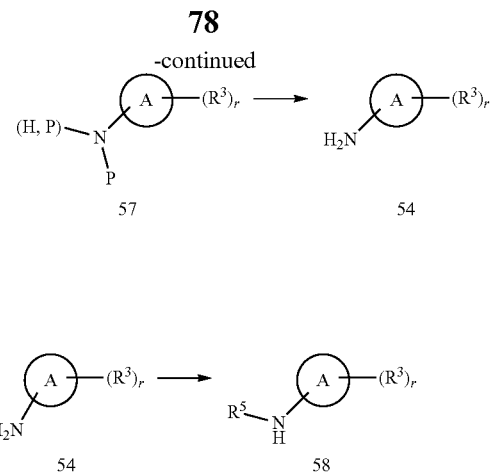

In certain embodiments of the schemes above,

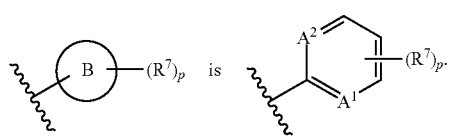

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, 5$^{th}$ ed. (2001). Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Example 1

Preparation of (5-fluoropyridin-2-yl)(4-(5-methyl-1H-pyrazol-3-ylamino)quinazolin-2-yl)methanone

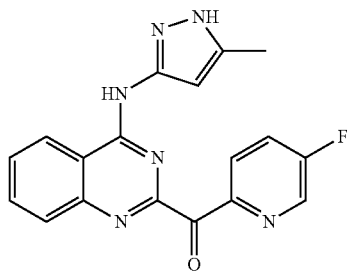 [SMILES: Cc1cc(Nc2nc(C(=O)c3ccc(F)cn3)nc3ccccc23)n[nH]1]

Step A:

To a stirred solution of 2-bromo-5-fluoropyridine (237 mg, 2.11 mmol) in anhydrous diethyl ether (7 mL) at −78° C. was added dropwise 1.7 M tert-butyl lithium/pentane (4 mL, 6.8 mmol). The brown mixture was stirred at −78° C. for 20 min, then ethyl 4-chloroquinazoline-2-carboxylate (500 mg, 2.11 mmol) in 3:1 diethyl ether/DCM (4 mL) was added to the mixture over 40 min. The resulting mixture was stirred at −78° C. for 1 h and then at −40° C. for 4 h. Then 10% aq ammonium chloride was added and the mixture was extracted three times with EtOAc. The combined organic layers were dried over MgSO$_4$, filtered, and concentrated under reduced pressure. The residue was purified by silica gel chromatography eluting with 0-50% EtOAc/hexane to afford (4-chloroquinazolin-2-yl)(5-fluoropyridin-2-yl)methanone (150 mg, 25%). $^1$H NMR (300 MHz, CDCl$_3$) δ 8.50 (d, J=3 Hz, 1H), 8.37-8.28 (m, 2H), 8.17 (d, J=8.4 Hz, 1H), 8.04 (t, J=8.4 Hz, 1H), 7.83 (t, J=8.4 Hz, 1H), 7.63 (td, J=3 Hz, J=8.4 Hz, 1H); LC-MS (ESI) m/z 288 (M+H)$^+$.

Step B:

To a stirred mixture of (4-chloroquinazolin-2-yl)(5-fluoropyridin-2-yl)methanone (244 mg, 0.85 mmol) and 5-methyl-3-aminopyrazole (99 mg, 1.02 mmol) in N,N-dimethylformamide (3 mL) were added DIEA (0.3 mL, 4.22 mmol) and potassium iodide (141 mg, 0.85 mmol) and the mixture was stirred at rt for 15 h and then at 60° C. for 2.5 h. The mixture was allowed to cool to rt, and then water was added. The precipitated solid was collected by filtration. A portion of the solid (180 mg) was purified by preparative reverse-phase HPLC eluting with 30% to 70% acetonitrile/0.05% aq HOAc to afford (5-fluoropyridin-2-yl)(4-(5-methyl-1H-pyrazol-3-ylamino)quinazolin-2-yl)methanone (19.6 mg). $^1$H NMR (300 MHz, CDCl$_3$) δ 12.19 (s, 1H), 10.65 (s, 1H), 8.72-8.69 (m, 2H), 8.26 (s, 1H), 8.00 (td, J=3 Hz, J=8.7 Hz, 1H), 7.92-7.80 (m, 2H), 7.66 (t, J=7.5 Hz, 1H), 6.34 (s, 1H), 2.16 (s, 3H); LC-MS (ESI) m/z 349 (M+H)$^+$.

Example 2

Preparation 2-(difluoro(5-fluoropyridin-2-yl)methyl)-N-(5-methyl-1H-pyrazol-3-yl)quinazolin-4-amine

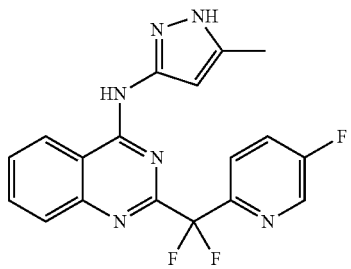 [SMILES: Cc1cc(Nc2nc(C(F)(F)c3ccc(F)cn3)nc3ccccc23)n[nH]1]

Step A:

To a mixture of 2-bromo-5-fluoropyridine (2 g, 11.36 mmol) and ethyl 2-bromo-2,2-difluoroacetate (1.6 mL, 12.5 mmol) in DMSO (4 mL) was added copper powder (1.6 g, 24.98 mmol) and the mixture was stirred at 50° C. overnight in a sealed flask. The mixture was diluted with DMSO (10 mL) and filtered through Celite. Then water and EtOAc were added and the mixture was shaken and again filtered through Celite. The organic layer was washed with water (1×) and brine (1×) and dried over sodium sulfate, and concentrated to afford ethyl 2,2-difluoro-2-(5-fluoropyridin-2-yl)acetate as a yellow oil (1.5 g, 60%). $^1$H NMR (300 MHz, CDCl$_3$) δ 1.34 (t, 3H), 4.38 (q, 2H), 7.56 (dt, 1H), 7.77 (dd, 1H), 8.50 (d, 1H).

Step B:

To ethyl 2,2-difluoro-2-(5-fluoropyridin-2-yl)acetate (560 mg, 2.55 mmol) in 1:1 MeOH/THF (10 mL) at rt was added 1 M NaOH (2.8 mL, 2.8 mmol). The solution was stirred for 10 min and then concentrated to dryness to afford sodium 2,2-difluoro-2-(5-fluoropyridin-2-yl)acetate (548 mg, quantitative). $^1$H NMR (300 MHz, DMSO-d$_6$) δ 7.66 (dd, 1H), 7.79 (dt, 2H), 8.54 (d, 1H).

Step C:

To a mixture of sodium 2,2-difluoro-2-(5-fluoropyridin-2-yl)acetate (100 mg, 0.47 mmol), HATU (213 mg, 0.56 mmol) and 2-aminobenzamide (77 mg, 0.56 mmol) was added DMF (2 mL) and the mixture was stirred overnight at rt. The mixture was partitioned between saturated aq ammonium chloride and EtOAc, and the organic layer was concentrated. The residue was purified by silica gel chromatography eluting with 2-10% MeOH/DCM to afford 2-(2,2-difluoro-2-(5-fluoropyridin-2-yl)acetamido)benzamide as an oil (110 mg, 74%). LC-MS (ESI) m/z 332 (M+Na)$^+$.

Step D:

To 2-(2,2-difluoro-2-(5-fluoropyridin-2-yl)acetamido)benzamide (580 mg, 1.87 mmol) were added dichloroethane (15 mL) and TEA (11 mL, 75 mmol) followed by chlorotrimethylsilane (3.56 mL, 28 mmol) and the mixture was heated at 85° C. for 2-3 h. The mixture was concentrated to dryness and the residue was partitioned between saturated aq ammonium chloride and EtOAc. The organic layer was concentrated and the residue was purified by silica gel chromatography eluting with 0-10% MeOH/DCM to afford 2-(difluoro(5-fluoropyridin-2-yl)methyl)quinazolin-4-ol as a solid (500 mg, 91%). LC-MS (ESI) m/z 292 (M+H)$^+$.

Step E:

To 2-(difluoro(5-fluoropyridin-2-yl)methyl)quinazolin-4-ol (200 mg, 0.68 mmol) was added phosphorous oxychloride (4 mL) and the mixture was heated at 90° C. for 1 h. The mixture was concentrated and toluene (4 mL) was added and evaporated. This crude material was partitioned between EtOAc and a saturated sodium bicarbonate solution and the organic layer was dried over sodium sulfate and concentrated to afford a yellow solid. To this solid was added a solution of 5-methyl-1H-pyrazol-3-amine (100 mg, 1.03 mmol), DIEA (0.18 mL, 1.54 mmol), and potassium iodide (113 mg, 1.03 mmol) in DMF (4 mL) and the mixture was stirred at rt overnight. Acetic acid (0.2 mL) was added and the mixture was purified by preparative HPLC (Varian diphenyl reverse phase column, eluting with a gradient of solvent B=0.05% HOAc/ACN and solvent A=0.05% HOAc/H$_2$O) to afford 2-(difluoro(5-fluoropyridin-2-yl)methyl)-N-(5-methyl-1H-pyrazol-3-yl)quinazolin-4-amine (88 mg, 35%). $^1$H NMR (300 MHz, DMSO-d$_6$) δ 2.18 (s, 3H), 5.99 (s, 1H), 7.65 (t, 1H), 7.83-7.94 (m, 2H), 7.97-8.07 (m, 2H), 8.58-8.78 (m, 2H), 10.70 (s, 1H), 12.18 (bs, 1H); LC-MS (ESI) m/z 371 (M+H)$^+$.

Example 3

Preparation 2-(difluoro(5-fluoropyrimidin-2-yl)methyl)-N-(5-methyl-1H-pyrazol-3-yl)quinazolin-4-amine

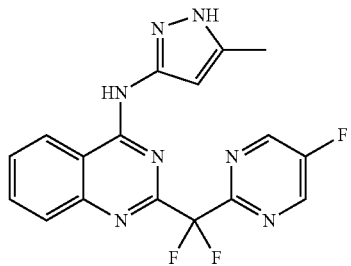 [SMILES: Cc1cc(Nc2nc(C(F)(F)c3ncc(F)cn3)nc3ccccc23)n[nH]1]

Step A:
To 2-chloro-5-fluoropyrimidine (2 mL, 22.18 mmol) were added propionitrile (20 mL) and bromotrimethylsilane (6 mL), and the mixture was heated in a sealed vial at 150° C. for 1 h. The mixture was allowed to cool, and then was concentrated under reduced pressure. The residue was partitioned between EtOAc and saturated aq NaHCO$_3$ and the organic phase was dried over sodium sulfate and concentrated under reduced pressure. The residue was dissolved in hexanes and cooled to −30° C. overnight to give a solid, which was collected by filtration to afford 2-bromo-5-fluoropyrimidine (2.03 g, 51%). $^1$H NMR (300 MHz, CDCl$_3$) δ 8.49 (s, 2H).

Step B:
To 2-bromo-5-fluoropyrimidine (500 mg, 2.8 mmol) were added DMSO (1.5 mL), ethyl 2-bromo-2,2-difluoroacetate (0.4 mL, 3.1 mmol), and copper powder (390 mg, 6.16 mmol). The reaction vessel was sealed, and then evacuated and flushed with argon (2×). The mixture was heated at 50° C. overnight, then diluted with EtOH and filtered through Celite washing with EtOAc. To the filtrate was added water and the mixture was filtered through Celite again. The separated organic layer was washed with brine (2×), dried over sodium sulfate, and concentrated to afford ethyl 2,2-difluoro-2-(5-fluoropyrimidin-2-yl)acetate as an oil (470 mg, 76%). $^1$H NMR (300 MHz, CDCl$_3$) δ 8.74 (s, 2H), 4.41 (q, J=7.2 Hz, 2H), 1.35 (t, J=7.2 Hz, 3H).

Step C:
To ethyl 2,2-difluoro-2-(5-fluoropyrimidin-2-yl)acetate (470 mg, 2.13 mmol) were added MeOH (4 mL), THF (4 mL) and 1.2; N NaOH (2 mL, 2.4 mmol). The solution was stirred at rt for 30 min and then concentrated to dryness to afford sodium 2,2-difluoro-2-(5-fluoropyrimidin-2-yl)acetate (430 mg, 94%). $^1$H NMR (300 MHz, DMSO-d$_6$) δ 8.94 (s, 2H).

Step D:
To sodium 2,2-difluoro-2-(5-fluoropyrimidin-2-yl)acetate (400 mg, 1.87 mmol), HATU (850 mg, 2.24 mmol), and 2-aminobenzamide (305 mg, 2.24 mmol) was added DMF (7 mL) and the mixture was stirred at rt overnight. The mixture was diluted with EtOAc and washed with saturated aq NH$_4$Cl, saturated aq NaHCO$_3$, and brine. The organic layer was dried over sodium sulfate and concentrated under reduced pressure. The residue was purified by silica gel chromatography eluting with 0-12% MeOH/DCM to afford 2-(2,2-difluoro-2-(5-fluoropyrimidin-2-yl)acetamido)benzamide (374 mg, 44%); LC-MS (ESI) m/z 333 (M+Na)$^+$.

Step E:
To 2-(2,2-difluoro-2-(5-fluoropyrimidin-2-yl)acetamido)benzamide (230 mg, 1.03 mmol) were added 1,2-dichloroethane (8 mL), TEA (5.75 mL, 41.2 mmol) and chlorotrimethylsilane (2 mL, 15.45 mmol) and the mixture was heated at 85° C. in a sealed vessel overnight. The mixture was allowed to cool and then was concentrated under reduced pressure. The residue was diluted with EtOAc and washed with saturated aq NaHCO$_3$ and brine. The organic layer was dried over sodium sulfate and concentrated under reduced pressure. The residue was purified by silica gel chromatography eluting with 0-12% MeOH/DCM to afford 2-(difluoro(5-fluoropyrimidin-2-yl)methyl)quinazolin-4-ol (210 mg, 69%). LC-MS (ESI) m/z 293 (M+H)$^+$.

Step F:
To 2-(difluoro(5-fluoropyrimidin-2-yl)methyl)quinazolin-4-ol (190 mg, 0.65 mmol) was added phosphorous oxychloride (4 mL) and the mixture was heated at 95° C. for 2 h. The mixture was concentrated under reduced pressure, toluene was added, and the solution was again concentrated under reduced pressure. The residue was diluted with EtOAc and washed with saturated aq NaHCO$_3$. The organic layer was dried over sodium sulfate and concentrated under reduced pressure. To the residue was added a solution of 5-methyl-1H-pyrazol-3-amine (72 mg, 0.74 mmol), DIEA (0.14 mL, 0.78 mmol), and KI (40 mg, 0.24 mmol) in DMF (4 mL) and the mixture was stirred at rt overnight. AcOH (0.2 mL) was added and the mixture was purified by preparative HPLC (Varian diphenyl reverse phase column, eluted with gradient of solvent B=0.05% AcOH/ACN and solvent A=0.05% AcOH/H$_2$O) to afford 2-(difluoro(5-fluoropyrimidin-2-yl)methyl)-N-(5-methyl-1H-pyrazol-3-yl)quinazolin-4-amine (80 mg, 32%). $^1$H NMR (300 MHz, DMSO-d$_6$) δ 12.19 (br s, 1H), 10.72 (s, 1H), 9.13 (s, 2H), 8.70 (d, J=8.1 Hz, 1H), 7.78-8.01 (m, 2H), 7.66 (t, J=7.3 Hz, 1H), 5.94 (s, 1H), 2.18 (s, 3H); LC-MS (ESI) m/z 372 (M+H)$^+$.

Example 4

Preparation 2-(difluoro(5-fluoropyridin-2-yl)methyl)-N-(1H-pyrazol-3-yl)quinazolin-4-amine

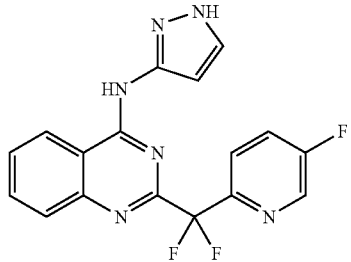 [SMILES: Fc1ccc(C(F)(F)c2nc(Nc3cc[nH]n3)c3ccccc3n2)nc1]

Step A:
To 2-(difluoro(5-fluoropyridin-2-yl)methyl)quinazolin-4-ol from Example 2 Step D (1.82 g, 6.25 mmol) was added phosphorousoxychloride (20 mL) and the mixture was heated at 95° C. for 3 h. The mixture was concentrated under reduced pressure and then toluene (20 mL) was added and evaporated. The residue was dissolved in EtOAc and washed with saturated NaHCO$_3$ (1×) and brine (1×), dried over Na$_2$SO$_4$, and concentrated. The residue was purified by silica gel chromatography eluting with 10-80% EtOAc/hexanes to afford 4-chloro-2-(difluoro(5-fluoropyridin-2-yl)methyl)quinazoline (1.59 g, 82%). $^1$H NMR (300 MHz, DMSO-d$_6$) δ 8.61 (d, J=2.6 Hz, 1H), 8.38 (d, J=8.3 Hz, 1H), 8.17-8.29 (m, 2H), 8.06-8.15 (m, 1H), 7.96-8.06 (m, 2H); LC-MS (ESI) m/z 310 (M+H)$^+$.

Step B:
To 4-chloro-2-(difluoro(5-fluoropyridin-2-yl)methyl)quinazoline (100 mg, 0.32 mmol) was added a solution of KI (20 mg, 0.12 mmol), DIEA (0.068 mL, 0.39 mmol), and 1H-pyrazol-3-amine (40 mg, 0.48 mmol) in DMF (2 mL). The mixture was stirred overnight at rt. AcOH (0.14 mL) was added and the mixture was purified by preparative HPLC (Varian diphenyl reverse phase column, eluted with gradient of solvent B=0.05% AcOH/ACN and solvent A=0.05% AcOH/H$_2$O) to afford 2-(difluoro(5-fluoropyridin-2-yl)methyl)-N-(1H-pyrazol-3-yl)quinazolin-4-amine (15 mg, 13%). $^1$H NMR (300 MHz, DMSO-d$_6$) δ 12.52 (br s, 1H), 10.82 (br s, 1H), 8.53-8.86 (m, 2H), 7.77-8.13 (m, 4H), 7.57-7.74 (m, 2H), 6.50 (br s, 1H); LC-MS (ESI) m/z 357 (M+H)$^+$.

Example 5

Preparation 2-(difluoro(5-fluoropyridin-2-yl)methyl)-N-(5-methoxy-1H-pyrazol-3-yl)quinazolin-4-amine

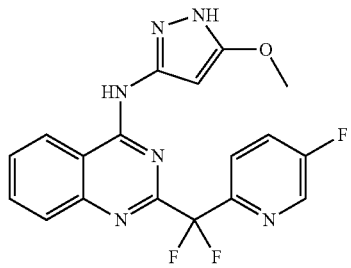 [SMILES: COc1cc(Nc2nc(C(F)(F)c3ccc(F)cn3)nc3ccccc23)n[nH]1]

Step A:
A stirred mixture of 1-nitropyrazole (3.45 g, 30.5 mmol) in benzonitrile (33 mL) was heated at 180° C. for 3 h. The mixture was cooled to rt, diluted with hexane and stirred at rt for 20 min. The precipitated solid was collected by filtration to afford 3-nitro-1H-pyrazole as a tan solid (3.16 g, 91%). $^1$H NMR (300 MHz, DMSO-d$_6$) δ 13.94 (br s, 1H), 8.03 (d, J=2.4 Hz, 1H), 7.03 (t, J=2.4 Hz, 1H).

Step B:
To a stirred mixture of 3-nitro-1H-pyrazole (3.16 g, 27.9 mmol) in glacial acetic acid (20 mL) at 0° C. was added fuming nitric acid (2.6 mL, 58.69 mmol) dropwise, followed by acetic anhydride (6.6 mL, 69.87 mmol). The mixture was stirred and allowed to warm to rt over 3 h, then poured into ice water (50 mL) and stirred for 20 h. The mixture was extracted with EtOAc combined organic layers were dried over MgSO$_4$, filtered and concentrated to dryness to afford 1,3-dinitro-1H-pyrazole (4.3 g, 97%). $^1$H NMR (300 MHz, DMSO-d$_6$) δ 8.00 (br s, 1H), 6.44 (br s, 1H).

Step C:
A stirred mixture of 1,3-dinitro-1H-pyrazole (4.3 g, 27.20 mmol) in benzonitrile (60 mL) was heated at 180° C. for 3 h. The mixture was cooled to rt and partitioned between 1N sodium hydroxide and hexane. The organic layer was separated and the solid precipitate in the aqueous layer was filtered and triturated with toluene to afford 1.2 g of a pale yellow solid. The filtrate was neutralized with 1N HCl and extracted with EtOAc. The combined organic layers were dried over MgSO$_4$, filtered and concentrated to dryness. The residue was purified by silica gel flash chromatography eluting with 0-30% EtOAc/hexane and then with 0-10% DCM/MeOH. The obtained solid was triturated with diethyl ether to afford 1.36 g of solid, which was combined with the previously obtained solid to afford 3,5-dinitro-1H-pyrazole (2.56 g, 59%). $^1$H NMR (300 MHz, DMSO-d$_6$) δ 7.28 (s, 1H).

Step D:
To a stirred mixture of 3,5-dinitro-1H-pyrazole (2.5 g, 15.81 mmol) and potassium carbonate (4.36 g, 31.62 mmol) in DMF (50 mL) at 0° C. was added (2-(chloromethoxy)ethyl)trimethylsilane (3.07 mL, 17.39 mmol) and the mixture was stirred at rt for 6 h. The mixture was concentrated under reduced pressure and the residue was purified by silica gel flash chromatography eluting with 0-20% EtOAc/hexane to afford 3,5-dinitro-1-((2-(trimethylsilyl)ethoxy)methyl)-1H-pyrazole as a colorless oil (2.7 g, 59%). $^1$H NMR (300 MHz, CDCl$_3$) δ 7.68 (s, 1H), 6.00 (s, 2H), 3.72-3.67 (m, 2H), 0.97-0.91 (m, 2H), 0.00 (s, 9H).

Step E:
To a stirred solution of anhydrous MeOH (25 mL) was added sodium (300 mg, 13.04 mmol) portionwise. To the clear solution was added SEM-protected 3,5-dinitropyrazole from Step D (1 g, 3.47 mmol) and the mixture was stirred at 60° C. for 2 h. The mixture was allowed to cool to rt and was concentrated under reduced pressure. The residue was purified by silica gel flash chromatography eluting with 0-30% EtOAc/hexane to afford a single regioisomer of SEM-protected 3-methoxy-5-nitropyrazole (SEM=((2-(trimethylsilyl)ethoxy)methyl)) as a clear oil (723 mg, 76%). $^1$H NMR (300 MHz, CDCl$_3$) δ 6.23 (s, 1H), 5.41 (s, 2H), 4.02 (s, 3H), 3.70-3.65 (m, 2H), 0.96-0.91 (m, 2H), 0.00 (s, 9H).

Step F:
To a stirred solution of SEM-protected 3-methoxy-5-nitropyrazole from Step E (723 mg, 2.65 mmol) in ethanol (20 mL) was added palladium on activated carbon (100 mg) and the resulting suspension was degassed and filled with hydrogen. After stirring at rt for 1 h, additional palladium on activated carbon (200 mg) was added and the mixture was degassed and filled with hydrogen. The reaction mixture was stirred at rt for 75 h, filtered through Celite, and the filtrate was concentrated under reduced pressure. The residue was purified by silica gel flash chromatography eluting with 0-50% EtOAc/hexane and then with 0-20% DCM/MeOH to afford SEM-protected 3-amino-5-methoxypyrazole (478 mg, 74%).

$^1$H NMR (300 MHz, DMSO-$d_6$) δ 4.93-4.92 (m, 3H), 4.62 (s, 2H), 3.78 (s, 3H), 3.47 (t, J=8.1 Hz, 2H), 0.88 (t, J=8.1 Hz, 2H), −0.04 (s, 9H).

Step G:

To a mixture of 4-chloro-2-(difluoro(5-fluoropyridin-2-yl)methyl)quinazoline from Example 4 Step A (203 mg, 0.65 mmol), Pd$_2$(dibenzylideneacetone)$_3$ (24 mg, 0.026 mmol), 4,5-bis(diphenylphosphino)-9,9-dimethylxanthene (45 mg, 0.078 mmol), SEM-protected 3-amino-5-methoxypyrazole from Step F (188 mg, 0.77 mmol), and Na$_2$CO$_3$ (96 mg, 0.91 mmol) was added toluene (4 mL). The reaction vessel was evacuated and flushed with argon three times, then the vessel was sealed and the mixture was heated at 100° C. overnight. The mixture was allowed to cool to rt, then was filtered, washing with EtOAc. The filtrate was concentrated under reduced pressure and the residue was purified by silica gel chromatography eluting with 0-50% EtOAc/DCM to afford the SEM protected product. LC-MS (ESI) m/z 517 (M+H)$^+$.

Step H:

To the SEM-protected product (127 mg, 0.24 mmol) was added TFA (2 mL) and the mixture was stirred for 30 min at rt. The mixture was concentrated under reduced pressure and the residue was purified by preparative HPLC (Varian diphenyl reverse phase column, eluted with gradient of solvent B=0.05% AcOH/ACN and solvent A=0.05% AcOH/H$_2$O) to afford 2-(difluoro(5-fluoropyridin-2-yl)methyl)-N-(5-methoxy-1H-pyrazol-3-yl)quinazolin-4-amine (31 mg, 33%). $^1$H NMR (300 MHz, DMSO-$d_6$) δ 10.87 (br s, 1H), 8.66 (d, J=2.3 Hz, 1H), 8.57 (d, J=8.3 Hz, 1H), 7.88-8.08 (m, 4H), 7.74 (t, J=7.2 Hz, 1H), 5.69 (s, 1H), 3.76 (s, 3H); LC-MS (ESI) m/z 387 (M+H)$^+$.

Example 6

Preparation of 2-(difluoro(5-fluoropyridin-2-yl)methyl)-7-methoxy-N-(5-methyl-1H-pyrazol-3-yl)quinazolin-4-amine

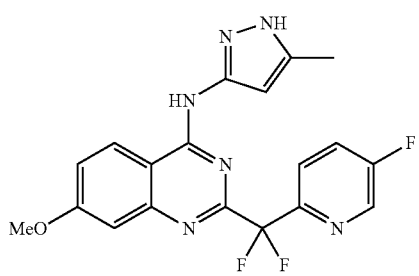 [SMILES: COc1ccc2c(Nc3cc(C)[nH]n3)nc(C(F)(F)c3ccc(F)cn3)nc2c1]

Step A:

Sodium 2,2-difluoro-2-(5-fluoropyridin-2-yl)acetate from Example 2 Step B (2.3 g, 10.8 mmol) and 2-amino-4-methoxybenzamide (1.5 g, 9.0 mmol) were combined with trimethylsilyl polyphosphate (15 mL) and the mixture was heated at 115° C. for 18 h with vigorous stirring. To mixture was allowed to cool to rt, and then was partitioned between were water (15 mL) and EtOAc (15 mL). The organic layer was separated and the aqueous layer (pH~1) was extracted with EtOAc (3×30 mL). The combined organic layers were dried over MgSO$_4$, filtered, and concentrated under reduced pressure. The residue was purified by silica gel chromatography eluting with 1:10 to 1:1 EtOAc/hexanes to afford 2-(difluoro(5-fluoropyridin-2-yl)methyl)-7-methoxyquinazolin-4(3H)-one (487 mg) as an off-white solid.

Step B:

To 2-(difluoro(5-fluoropyridin-2-yl)methyl)-7-methoxyquinazolin-4(3H)-one (480 mg, 1.5 mmol) were added DIEA (0.55 mL, 3.0 mmol) and phosphorous oxychloride (10 mL, 108 mmol), and the mixture was heated at 115° C. for 6 h. The mixture was allowed to cool to rt and was concentrated under reduced pressure. Toluene was added and evaporated twice to remove residual phosphorous oxychloride. The residue was partitioned between EtOAc (20 mL) and cold saturated aq NaHCO$_3$ (10 mL), and the separated EtOAc layer was diluted with EtOAc (60 mL) and washed with saturated aq NaHCO$_3$ (10 mL) and brine (2×10 mL), dried over MgSO$_4$, filtered, and concentrated under reduced pressure to afford 4-chloro-2-(difluoro(5-fluoropyridin-2-yl)methyl)-7-methoxyquinazoline as a brown viscous oil (500 mg).

Step C:

To 4-chloro-2-(difluoro(5-fluoropyridin-2-yl)methyl)-7-methoxyquinazoline (355 mg, 0.91 mmol) in DMF (5.0 mL) at rt were added tert-butyl 3-amino-5-methyl-1H-pyrazole-1-carboxylate (0.448 g, 2.27 mmol) and DIEA (0.40 mL, 2.3 mmol), and the mixture was stirred at rt for 3 h. The mixture was purified by preparative reverse-phase HPLC using TFA as a modifier, and the fractions containing the desired product were neutralized with saturated aq NaHCO$_3$ and extracted with EtOAc (100 mL). The organic layer was separated, washed with brine (2×10 mL), dried over MgSO$_4$, filtered, and concentrated under reduced pressure to afford tert-butyl 3-(2-(difluoro(5-fluoropyridin-2-yl)methyl)-7-methoxyquinazolin-4-ylamino)-5-methyl-1H-pyrazole-1-carboxylate as a clear oil (104 mg).

Step D:

To tert-Butyl 3-(2-(difluoro(5-fluoropyridin-2-yl)methyl)-7-methoxyquinazolin-4-ylamino)-5-methyl-1H-pyrazole-1-carboxylate (100 mg, 0.20 mmol) was added 20% TFA/DCM, and the mixture was stirred at rt for 2.5 h. The mixture was concentrated and the residue was purified by preparative reverse-phase HPLC (TFA as a modifier). The fractions containing the desired product were neutralized with saturated aq NaHCO$_3$ and extracted with EtOAc (100 mL). The organic layer was separated, washed with brine (2×10 mL), dried over MgSO$_4$, filtered, and concentrated under reduced pressure to afford 2-(difluoro(5-fluoropyridin-2-yl)methyl)-7-methoxy-N-(5-methyl-1H-pyrazol-3-yl)quinazolin-4-amine as an off-white solid (33 mg, 41%). $^1$H NMR (250 MHz, DMSO-$d_6$) δ 12.10 (s, 1H), 10.54 (s, 1H), 8.67 (d, J=2.0 Hz, 1H), 8.59 (d, J=8.16 Hz, 1H), 7.97-8.06 (m, 2H), 7.22-7.28 (m, 2H), 5.97 (s, 1H), 3.93 (s, 3H), 2.17 (s, 3H). LCMS (ESI) m/z 401 (M+H)$^+$.

Example 7

Preparation of 7-bromo-2-(difluoro(5-fluoropyridin-2-yl)methyl)-N-(5-methyl-1H-pyrazol-3-yl)quinazolin-4-amine

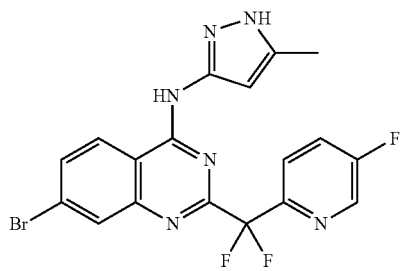

Step A:

To a mixture of sodium 2,2-difluoro-2-(5-fluoropyridin-2-yl)acetate from Example 2 Step B (2.05 g, 9.62 mmol) and 2-amino-4-bromobenzamide (1.89 g, 8.75 mmol) was added trimethylsilyl polyphosphate (~15 mL) and the mixture was stirred overnight at 120° C. Equal volumes of EtOAc and water were added and the resulting solution was stirred for 1 h. The EtOAc layer was washed with brine, dried over $Na_2SO_4$ and then concentrated under reduced pressure. $Et_2O$ was added and evaporated. Trituration of the residue with hexanes, followed by collection of the solid by filtration afforded 7-bromo-2-(difluoro(5-fluoropyridin-2-yl)methyl)quinazolin-4-ol (2.49 g, 77%). $^1$H NMR (300 MHz, DMSO-$d_6$) δ 11.37 (s, 1H), 8.76 (s, 1H), 7.97-8.07 (m, 2H), 7.88 (d, J=8.3 Hz, 1H), 7.69-7.81 (m, 2H); LC-MS (ESI) m/z 370/372 $(M+H)^+$.

Step B:

To a mixture of 7-bromo-2-(difluoro(5-fluoropyridin-2-yl)methyl)quinazolin-4-ol (1.0 g, 2.70 mmol) and Lawesson's Reagent (1.2 g, 2.97 mmol) was added pyridine (15 mL). The mixture was heated in a microwave reactor at 150° C. for 30 min. After cooling to rt, the mixture was partitioned between EtOAc (50 mL) and saturated aq $NaHCO_3$ (50 mL), then the organic layer was washed with 4N HCl (2×30 mL). The organic layer was dried over $Na_2SO_4$ and concentrated under reduced pressure to afford a residue (1.06 g). The residue was triturated with diethyl ether and hexanes and the solid was collected by filtration to afford 7-bromo-2-(difluoro(5-fluoropyridin-2-yl)methyl)quinazoline-4-thiol as a brown solid (0.715 g, 68%). $^1$H NMR (300 MHz, DMSO-$d_6$) δ 8.64-8.71 (m, 1H), 8.46-8.55 (m, 1H), 7.99-8.16 (m, 3H), 7.83-7.92 (m, 1H); LC-MS (ESI) m/z 386/388 $(M+H)^+$.

Step C:

To 7-bromo-2-(difluoro(5-fluoropyridin-2-yl)methyl)quinazoline-4-thiol (500 mg, 1.29 mmol) in isopropanol (10 mL) were added 1N NaOH (1.94 mL, 1.94 mmol) and iodomethane (0.097 mL, 1.55 mmol) and the mixture was stirred at rt for 30 min. A brown solid formed, which was collected by filtration and washed with MeOH to afford 7-bromo-2-(difluoro(5-fluoropyridin-2-yl)methyl)-4-(methylthio)quinazoline (0.373 g, 72%). $^1$H NMR (300 MHz, $CDCl_3$) δ 8.45-8.51 (m, 1H), 8.26-8.32 (m, 1H), 7.93-8.03 (m, 2H), 7.74 (dd, J=1.9, 8.9 Hz, 1H), 7.54-7.65 (m, 1H), 2.61 (s, 3H); LC-MS (ESI) m/z 400/402 $(M+H)^+$.

Step D:

To 7-bromo-2-(difluoro(5-fluoropyridin-2-yl)methyl)-4-(methylthio)quinazoline (100 mg, 0.25 mmol) in DCM (3 mL) at 0° C. was added 70% meta-chloroperoxybenzoic acid (74 mg, 0.30 mmol) and the mixture was stirred at 0° C. for 80 min. Then additional 70% meta-chloroperoxybenzoic acid (70%, 15 mg, 0.086 mmol) was added and the mixture was stirred at 0° C. for 10 min. The mixture was diluted with DCM (10 mL), washed with saturated aq $NaHCO_3$ (20 mL) and saturated aq sodium thiosulfate (20 mL), dried over $Na_2SO_4$ and concentrated under reduced pressure. To the residue (133 mg) at rt was added 5-methyl-1H-pyrazol-3-amine (92 mg, 0.96 mmol) in THF (3 mL). The mixture was stirred for 40 min and then concentrated under reduced pressure. The residue was purified by preparative HPLC (Phenomenex C-18 reverse phase column, eluted with gradient of solvent B=0.05% AcOH/ACN and solvent A=5% ACN/0.05% AcOH/$H_2O$) to afford 7-bromo-2-(difluoro(5-fluoropyridin-2-yl)methyl)-N-(5-methyl-1H-pyrazol-3-yl)quinazolin-4-amine (4.42 mg, 3.1%). $^1$H NMR (300 MHz, DMSO-$d_6$) δ 12.09-12.33 (m, 1H), 10.73-10.99 (m, 1H), 8.66 (s, 2H), 8.00 (d, J=5.5 Hz, 3H), 7.74-7.87 (m, 1H), 5.95 (br s, 1H), 2.16 (s, 3H); LC-MS (ESI) m/z 449/451 $(M+H)^+$.

Example 8

Preparation of 2-(difluoro(5-fluoropyridin-2-yl)methyl)-4-(5-methyl-1H-pyrazol-3-ylamino)quinazoline-7-carbonitrile

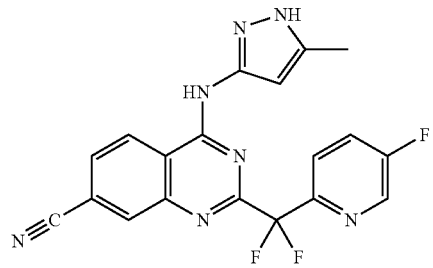 [SMILES: Cc1cc(Nc2nc(C(F)(F)c3ccc(F)cn3)nc3cc(C#N)ccc23)n[nH]1]

Step A:

To a mixture of 1,1'-bis(diphenylphosphino)ferrocene (25 mg, 0.045 mmol), zinc cyanide (55 mg, 0.47 mmol), and 7-bromo-2-(difluoro(5-fluoropyridin-2-yl)methyl)-4-(methylthio)quinazoline from Example 7 Step E (150 mg, 0.376) was added tris(dibenzylideneacetone)dipalladium (34 mg, 0.031 mmol) in DMF (3 mL). The reaction vessel was evacuated, and flushed with argon (2×), then the mixture was heated at 90° C. overnight during which time most of the solvent evaporated. The mixture was diluted with EtOAc (20 mL) and washed with water (20 mL), 2N $NH_4OH$ (20 mL), and brine, dried over $Na_2SO_4$, and concentrated under reduced pressure onto Celite. The mixture was purified by silica gel chromatography eluting with a 10-60% EtOAc/hexanes to afford 2-(difluoro(5-fluoropyridin-2-yl)methyl)-4-(methylthio)quinazoline-7-carbonitrile as a solid (0.103 g, 79%). LC-MS (ESI) m/z 347 $(M+H)^+$ Step B:

2-(Difluoro(5-fluoropyridin-2-yl)methyl)-4-(5-methyl-1H-pyrazol-3-ylamino)quinazoline-7-carbonitrile was prepared as a white solid (12 mg, 10%) by following a procedure analogous to that described in Example 7 Step D, substituting 2-(difluoro(5-fluoropyridin-2-yl)methyl)-4-(methylsulfinyl)quinazoline-7-carbonitrile for the 7-bromo-2-(difluoro(5-fluoropyridin-2-yl)methyl)-4-(methylthio)quinazoline used in Example 7. $^1$H NMR (300 MHz, DMSO-$d_6$) δ 12.23-12.30

(m, 1H), 11.06 (s, 1H), 8.86 (d, J=8.7 Hz, 1H), 8.67 (s, 1H), 8.42 (d, J=1.1 Hz, 1H), 7.97-8.05 (m, 3H), 5.99 (s, 1H), 2.18 (s, 3H); LC-MS (ESI) m/z 396 (M+H)+.

Example 9

Preparation of 7-cyclopropyl-2-(difluoro(5-fluoropyridin-2-yl)methyl)-N-(5-methyl-1H-pyrazol-3-yl)quinazolin-4-amine

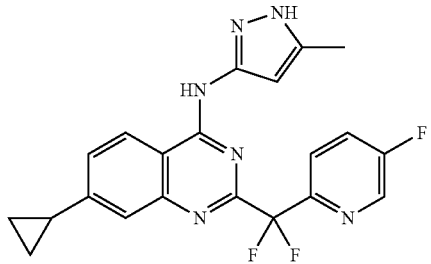 [SMILES: Cc1cc(Nc2nc(C(F)(F)c3ccc(F)cn3)nc3cc(C4CC4)ccc23)n[nH]1]

Step A:

To a mixture of water (0.5 mL) and toluene (6 mL), was added 7-bromo-2-(difluoro(5-fluoropyridin-2-yl)methyl)-4-(methylthio)quinazoline from Example 7 Step E (167 mg, 0.42 mmol) and the reaction vessel was evacuated and flushed with argon. Cyclopropylboronic acid (55 mg, 0.63 mmol) and tripotassium phosphate (311 mg, 1.47 mmol) were added and the reaction flask was vessel was again evacuated and flushed with argon.
Bis(triphenylphosphine)palladium(II)dichloride (31 mg, 0.04 mmol) was added and the reaction vessel was again evacuated and flushed with argon. The mixture was heated to 100° C. for 7 h, allowed to cool, diluted with DCM (15 mL), and concentrated under reduced pressure onto celite. The mixture was purified by silica gel chromatography eluting with 0-30% EtOAc/hexanes to afford impure 7-cyclopropyl-2-(difluoro(5-fluoropyridin-2-yl)methyl)-4-(methylthio)quinazoline (137 mg). LC-MS (ESI) m/z 362 (M+H)+

Step B:

To 7-cyclopropyl-2-(difluoro(5-fluoropyridin-2-yl)methyl)-4-(methylthio)quinazoline from Step A (137 mg, 0.378 mmol) in DCM (5 mL) at 0° C. was added 70% meta-chloroperoxybenzoic acid (139 mg, 0.567 mmol). The mixture was stirred for at 0° C. for 20 min, then DCM (15 mL) was added and the mixture was washed with saturated aq NaHCO$_3$ (20 mL) and saturated aq sodium thiosulfate (20 mL). The organic layer was dried over Na$_2$SO$_4$ and concentrated under reduced pressure. To the residue was added 5-methyl-1H-pyrazol-3-amine (0.107 g, 1.01 mmol) in THF (5 mL) and the mixture was stirred at room temperature for 40 min and then concentrated under reduced pressure. The residue was purified by reverse phase HPLC (Phenomenex C-18 reverse phase column, eluted with gradient of solvent B=0.05% AcOH/CH$_3$CN and solvent A=0.05% aq AcOH) to afford 7-cyclopropyl-2-(difluoro(5-fluoropyridin-2-yl)methyl)-N-(5-methyl-1H-pyrazol-3-yl)quinazolin-4-amine (12 mg, 8%) $^1$H NMR (300 MHz, DMSO-d$_6$) δ 12.07-12.19 (m, 1H), 10.51-10.63 (m, 1H), 8.66 (s, 1H), 8.54 (d, J=8.7 Hz, 1H), 7.94-8.04 (m, 2H), 7.51 (s, 1H), 7.36 (d, J=8.7 Hz, 1H), 5.97 (s, 1H), 2.10-2.21 (m, 4H), 1.09 (dd, J=2.3, 8.1 Hz, 2H), 0.87-0.94 (m, 2H); LC-MS (ESI) m/z 411 (M+H)+

Example 10

2-(Difluoro(5-fluoropyridin-2-yl)methyl)-8-methyl-N-(5-methyl-1H-pyrazol-3-yl)quinazolin-4-amine

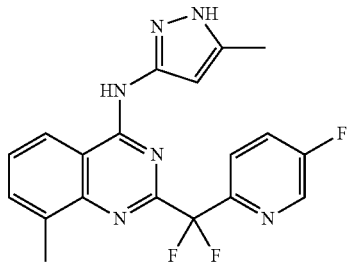 [SMILES: Cc1cc(Nc2nc(C(F)(F)c3ccc(F)cn3)nc3c(C)cccc23)n[nH]1]

Step A:

To 2-amino-3-methylbenzoic acid (1.5 g, 10 mmol) in DMF (5 mL) at rt were added hydroxybenzatriazole (2.0 g, 13 mmol), 1-ethyl-3-(3-dimethylaminopropyl)carbodiimide (2.3 g, 12 mmol), ammonium chloride (2.3 g, 42 mmol), and diisopropylethylamine (7.5 ml, 42 mmol). The mixture was purged with N$_2$ and stirred for 60 h. The mixture was poured into water and extracte with EtOAc (50 mL×3), and the combined extracts were washed with brine (20 mL×2), dried over MgSO$_4$, filtered, and concentrated under reduced pressure. The residue was dissolved in DCM and purified by silica gel chromatography eluting with 1:1 EtOAc/hexanes to afford 2-amino-3-methyl-benzamide as a white solid (1.3 g, 87%).

Step B:

Sodium 2,2-difluoro-2-(5-fluoropyridin-2-yl)acetate from Example 2 Step B (1.02 g, 4.8 mmol) and 2-amino-3-methylbenzamide (0.6 g, 4.0 mmol) were combined with trimethylsilyl polyphosphate (8.0 mL) and the mixture was heated at 115° C. for 18 h with vigorous stirring. The mixture was allowed to cool to rt, then the mixture was partitioned between water (15 mL) and ethyl acetate (15 mL). The organic layer was separated and the aqueous layer (pH~1) was extracted with ethyl acetate (30 mL×3). The combined organic layers were separated, dried over magnesium sulfate, filtered, and concentrated under reduced pressure. The residue was purified by silica gel chromatography eluting with 1:10 to 1:1 EtOAc/hexanes to afford 2-[difluoro-(5-fluoropyridin-2-yl)-methyl]-8-methyl-3H-quinazolin-4-one as an off-white solid (0.6 g, 29%).

Step C:

To 2-[difluoro-(5-fluoro-pyridin-2-yl)-methyl]-8-methyl-3H-quinazolin-4-one (0.23 g, 0.76 mmol) were added DIEA (0.27 mL, 1.5 mmol) and POCl$_3$ (5 mL, 55 mmol) and the mixture was heated at 115° C. for 6 h. The mixture was allowed to cool to rt and the mixture was concentrated under reduced pressure. The residue was treated with toluene and concentrated to dryness twice. The residue was partitioned between EtOAc (20 mL) and cold saturated aq NaHCO$_3$ (10 mL). The separated EtOAc layer was diluted with of EtOAc (60 mL) and washed with saturated aq NaHCO$_3$ (10 mL) and brine (10 mL×2), dried over MgSO$_4$, filtered and concentrated under reduced pressure to afford 4-chloro-2-[difluoro-(5-fluoro-pyridin-2-yl)-methyl]-8-methyl-quinazoline as a brown viscous oil (242 mg, 99%).

Step D:

To 4-chloro-2-[difluoro-(5-fluoro-pyridin-2-yl)-methyl]-8-methylquinazoline (0.255 g, 0.79 mmol) in DMA (2 mL) were added 3-amino-5-methyl-pyrazole-1-carboxylic acid tert-butyl ester prepared according to US2007/219195 (0.31 g, 1.58 mmol) and acetic acid (0.15 mL) and the mixture was heated at 100° C. for 6.5 h. The mixture was allowed to cool to rt and then was purified by reverse phase HPLC using an ammonium acetate modifier. Fraction 1 containing pure product were combined, treated with saturated aq $NaHCO_3$ and concentrated under reduced pressure. The aqueous residue was extracted with DCM and the combined extracts were washed with saturated aq $NaHCO_3$ and brine, dried over $MgSO_4$, filtered, and concentrated under reduced pressure to afford 2-(difluoro(5-fluoropyridin-2-yl)methyl)-8-methyl-N-(5-methyl-1H-pyrazol-3-yl)quinazolin-4-amine (28 mg, 13%). $^1$H NMR (300 MHz, DMSO-$d_6$) δ 12.15 (br s, 1H), 10.57 (s, 1H), 8.67 (s, 1H), 8.50 (d, J=8.3 Hz, 1H), 7.92-8.11 (m, 2H), 7.75 (d, J=7.0 Hz, 1H), 7.52 (t, J=7.6 Hz, 1H), 5.96 (s, 1H), 2.59 (s, 3H), 2.17 (s, 3H); LC-MS (ESI) m/z 385 (M+H)$^+$.

Example 11

8-bromo-2-(difluoro(5-fluoropyridin-2-yl)methyl)-N-(5-methyl-1H-pyrazol-3-yl)quinazolin-4-amine

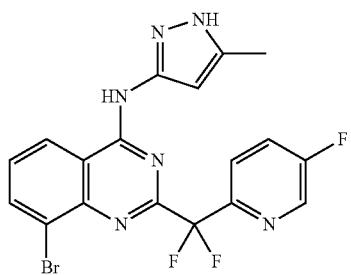 [SMILES: Cc1cc(Nc2nc(C(F)(F)c3ccc(F)cn3)nc3c(Br)cccc23)n[nH]1]

Step A:
To 2-amino-3-bromobenzoic acid (0.5 g, 2.3 mmol) in DMF (5 mL) at rt were added hydroxybenzatriazole (0.46 g, 3.0 mmol), 1-ethyl-3-(3-dimethylaminopropyl)carbodiimide (0.53 g, 2.8 mmol), ammonium chloride (0.5 g, 9.7 mmol), and diisopropylethylamine (1.7 ml, 9.7 mmol). The mixture was purged with $N_2$ and stirred for 6 h. The mixture was poured into water and extracted with EtOAc (3×50 mL). The combined extracts were washed with brine (2×20 mL), dried over MgSO4, filtered, and concentrated under reduced pressure. The residue was treated with DCM (10 mL) resulting in a precipitate which was collected by filtration and dried to afford 2-amino-3-bromobenzamide as a pale pink solid (0.42 g, 84%). LCMS (ESI) m/z 215/217 (M+H)$^+$ Step B:
Sodium 2,2-difluoro-2-(5-fluoropyridin-2-yl)acetate from Example 2 Step B (0.49 g, 2.3 mmol) and 2-amino-3-bromobenzamide (0.42 g, 1.9 mmol) were combined in trimethylsilylpolyphosphate (4.3 mL) at rt and the mixture was heated at 115° C. for 20 h with vigorous stirring. The mixture was allowed to cool to rt and then was partitioned between water (15 mL) and ethyl acetate (15 mL). The organic layer was separated and the aqueous layer (pH~1) was extracted with ethyl acetate (3×30 mL). The combined organic layers were dried over magnesium sulfate, filtered, and concentrated under reduced pressure. The residue was purified by silica gel chromatography eluting with a 1:10 to 1:1 EtOAc/hexanes to afford 2-[difluoro-(5-fluoro-pyridin-2-yl)-methyl]-8-bromo-3H-quinazolin-4-one as an off-white solid (0.19 g, 22%).

Step C:
To 2-[difluoro-(5-fluoro-pyridin-2-yl)-methyl]-8-bromo-3H-quinazolin-4-one (0.19 g, 0.52 mmol) at rt were added DIEA (0.18 mL, 1.04 mmol) and $POCl_3$ (3.5 mL, 76 mmol) and the mixture was heated at 115° C. for 6 h. The mixture was allowed to cool to rt and then was concentrated under reduced pressure. The residue was treated with toluene and concentrated to dryness twice. The residue was partitioned between EtOAc (20 mL) and cold saturated aq $NaHCO_3$ (10 mL), and the separated EtOAc layer was diluted with EtOAc (60 mL) and washed with saturated aq $NaHCO_3$ (10 mL), brine (2×10 mL), dried over $MgSO_4$, filtered, and concentrated under reduced pressure to afford 4-chloro-2-[difluoro-(5-fluoro-pyridin-2-yl)-methyl]-8-bromo-quinazoline as a brown viscous oil (207 mg, quantitative).

Step D:
To 4-chloro-2-[difluoro-(5-fluoro-pyridin-2-yl)-methyl]-8-bromo-quinazoline (0.19 g, 0.49 mmol) in DMA (1.0 mL) were added 3-amino-5-methyl-pyrazole-1-carboxylic acid tert-butyl ester (0.30 g, 1.53 mmol) and HOAc (0.065 mL, 1.1 mmol) and the mixture was heated to 100° C. for 5 h. The mixture was allowed to cool to rt and purified by reverse phase HPLC (ammonium acetate modifier). Fraction 1 containing pure product was treated with saturated aq $NaHCO_3$ (2-4 mL) and concentrated under reduced pressure. The aqueous residue was extracted with DCM (3×30 mL) and the combined extracts were washed with sat aqueous $NaHCO_3$ (10 mL) and brine (10 mL), dried over $MgSO_4$, filtered, and concentrated to dryness under reduced pressure to afford 8-bromo-2-(difluoro(5-fluoropyridin-2-yl)methyl)-N-(5-methyl-1H-pyrazol-3-yl)quinazolin-4-amine (48 mg, 20%) as a white solid. $^1$H NMR (300 MHz, DMSO-$d_6$) δ 12.22 (br s, 1H), 10.87 (br s, 1H), 8.57-8.81 (m, 2H), 8.24 (d, J=7.5 Hz, 1H), 8.02 (d, J=5.3 Hz, 2H), 7.54 (t, J=7.9 Hz, 1H), 5.95 (s, 1H), 2.17 (s, 3H); LC-MS (ESI) m/z 449/451 (M+H$^+$).

Example 12

Preparation of 2-(difluoro(5-fluoropyridin-2-yl)methyl)-8-fluoro-N-(3-methyl-1H-pyrazol-5-yl)quinazolin-4-amine

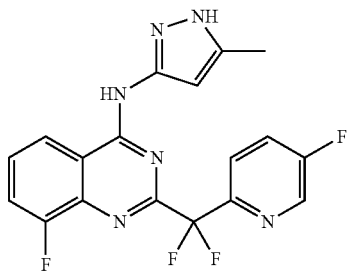 [SMILES: Cc1cc(Nc2nc(C(F)(F)c3ccc(F)cn3)nc3c(F)cccc23)n[nH]1]

Step A:
To 2-amino-3-fluorobenzoic acid (1.55 g, 10 mmol) in DMF (5 mL) at rt were added hydroxybenzatriazole (2.0 g, 13 mmol), 1-ethyl-3-(3-dimethylaminopropyl)carbodiimide (2.3 g, 12 mmol), ammonium chloride (2.3 g, 42 mmol), and DIEA (7.5 ml, 42 mmol). The mixture was purged with nitrogen and stirred for 6 h. The mixture was then poured into water and extracted with EtOAc (3×50 mL). The combined extracts were washed with brine (2×20 mL), dried over MgSO₄, filtered, and concentrated under reduced pressure. The residue was treated with DCM (10 mL) resulting in a precipitate that was collected by filtration to afford 2-amino-3-fluorobenzamide (670 mg). LC-MS (ESI) m/z 155 (M+H⁺)

Step B:
Sodium 2,2-difluoro-2-(5-fluoropyridin-2-yl)acetate from Example 2 Step B (51 mg, 0.24 mmol) and 2-amino-3-fluorobenzamide (31 mg, 0.2 mmol) were combined with polyphosphoric acid (1.0 g) and the mixture was heated at 115° C. for 20 h with vigorous stirring. The mixture was allowed to cool to rt, then water (3 mL) was added, resulting in a precipitate that was separated washing with DCE (2×8 mL). The combined DCE extracts were washed with brine (3 mL) and separated using Biotage Phase Separators. The organic fraction was concentrated using a Savant Speed Vac to afford 2-(difluoro(5-fluoropyridin-2-yl)methyl)-8-fluoroquinazolin-4(3H)-one as an off-white solid (60 mg). LCMS (ESI) m/z 310 (M+H)⁺.

Step C:
To 2-(difluoro(5-fluoropyridin-2-yl)methyl)-8-fluoroquinazolin-4(3H)-one (309 mg, 1.0 mmol) were added DIEA (0.36 mL, 2.0 mmol) and phosphorous oxychloride (7.0 mL, 76 mmol, and the mixture was heated at 115° C. for 6 h. The mixture was allowed to cool to rt and then was concentrated under reduced pressure. Toluene was added and evaporated twice to remove residual phosphorous oxychloride. The residue was partitioned between EtOAc (20 mL) and cold saturated aq NaHCO₃ (10 mL). The separated EtOAc layer was diluted with EtOAc (60 mL) and washed with saturated aq NaHCO₃ (10 mL) and brine (2×10 mL), dried over MgSO₄, filtered, and concentrated under reduced pressure to afford 4-chloro-2-(difluoro(5-fluoropyridin-2-yl)methyl)-8-fluoroquinazoline as a brown viscous oil (222 mg).

Step D:
To 4-chloro-2-(difluoro(5-fluoropyridin-2-yl)methyl)-8-fluoroquinazoline (295 mg, 0.90 mmol) in DMA (2.2 mL) were added tert-butyl 3-amino-5-methyl-1H-pyrazole-1-carboxylate and acetic acid (0.12 mL), and the mixture was heated at 100° C. for 6.5 h. The mixture was allowed to cool to rt and was purified by preparative reverse-phase HPLC using an ammonium acetate modifier. A later eluting fraction was treated with saturated aq NaHCO₃ and concentrated under reduced pressure. The aqueous residue was extracted with DCM (3×30 mL) and the combined extracts were washed with saturated aq NaHCO₃ (10 mL) and brine (10 mL), dried over MgSO₄, filtered, and concentrated under reduced pressure. The residue was treated with DCM, whereupon a precipitate formed, which was collected by filtration to afford 2-(difluoro(5-fluoropyridin-2-yl)methyl)-8-fluoro-N-(5-methyl-1H-pyrazol-3-yl)quinazolin-4-amine as a colorless solid (13 mg, 4%). ¹H NMR (300 MHz, DMSO-d₆) δ 12.23 (br s, 1H), 10.86 (br s, 1H), 8.67 (s, 1H), 8.52 (d, J=9 Hz, 1H), 8.00-8.02 (m, 2H), 7.77 (m, 1H), 7.63 (m, 1H), 5.97 (s, 1H), 2.17 (s, 3H). LCMS (ESI) m/z 389 (M+H)⁺.

Example 13

Preparation of 8-chloro-2-(difluoro(5-fluoropyridin-2-yl)methyl)-N-(5-methyl-1H-pyrazol-3-yl)quinazolin-4-amine

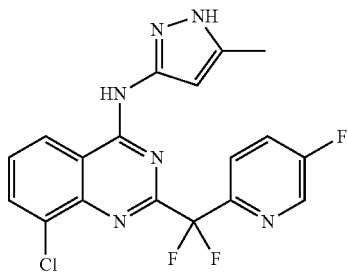 [SMILES: Cc1cc(Nc2nc(C(F)(F)c3ccc(F)cn3)nc3c(Cl)cccc23)n[nH]1]

Step A:
To 2-amino-3-chlorobenzoic acid (1.72 g, 10 mmol) in DMF (5 mL) were added hydroxybenzatriazole (2.0 g, 13 mmol), 1-ethyl-3-(3-dimethylaminopropyl)carbodiimide (2.3 g, 12 mmol), ammonium chloride (2.3 g, 42 mmol), and DIEA (7.5 ml, 42 mmol). The mixture was purged with nitrogen and was stirred for 6 h. The mixture was then poured into water and extracted with EtOAc (3×50 mL). The combined extracts were washed with brine (2×20 mL), dried over MgSO₄, filtered, and concentrated under reduced pressure. The residue was treated with DCM (10 mL) resulting in a precipitate that was collected by filtration to afford 2-amino-3-chlorobenzamide (860 mg). LCMS (ESI) m/z 171 (M+H)⁺.

Step B:
Sodium 2,2-difluoro-2-(5-fluoropyridin-2-yl)acetate from Example 2 Step B (51 mg, 0.24 mmol) and 2-amino-3-chlorobenzamide (34 mg, 0.20 mmol) were combined with polyphosphoric acid (1.0 g) and the mixture was heated at 115° C. for 20 h with vigorous stirring. The mixture was allowed to cool to rt and then water (3 mL) was added, resulting in a precipitate that was separated washing with DCE (2×8 mL). The combined DCE extracts were washed with brine (3 mL) and separated using Biotage Phase Separators. The organic fraction was concentrated using a Savant Speed Vac to afford 8-chloro-2-(difluoro(5-fluoropyridin-2-yl)methyl)quinazolin-4(3H)-one as an off-white solid (60 mg). LCMS (ESI) m/z 326 (M+H)+

Step C:
To 8-chloro-2-(difluoro(5-fluoropyridin-2-yl)methyl) quinazolin-4(3H)-one (250 mg, 0.77 mmol) were added DIEA (0.28 mL, 1.53 mmol) and phosphorous oxychloride (5.3 mL, 57 mmol), and the mixture was heated at 115° C. for 6 h. The mixture was allowed to cool to rt and was concentrated under reduced pressure. Toluene was added and evaporated twice, and the residue was partitioned between EtOAc (20 mL) and cold saturated aq NaHCO₃ (10 mL). The separated EtOAc layer was diluted with EtOAc (60 mL) and washed with saturated aq NaHCO₃ (10 mL) and brine (2×10 mL), dried over MgSO₄, filtered and concentrated under reduced pressure to afford 4,8-dichloro-2-(difluoro(5-fluoropyridin-2-yl)methyl)quinazoline as a brown viscous oil (294 mg).

Step D:
To 4,8-dichloro-2-(difluoro(5-fluoropyridin-2-yl)methyl) quinazoline (263 mg, 0.77 mmol) in DMA (2.0 mL) were added tert-butyl 3-amino-5-methyl-1H-pyrazole-1-carboxylate (300 mg, 1.53 mmol) and HOAc (0.102 mL), and the mixture was heated at 100° C. for 5 h. The mixture was allowed to cool to rt and was purified by preparative reverse-phase HPLC (diphenyl column eluting over 40 mins with a gradient of 25 to 80% acetonitrile (containing 0.05% HOAc) and water (containing 0.05% HOAc) to afford 8-chloro-2-(difluoro(5-fluoropyridin-2-yl)methyl)-N-(5-methyl-1H-pyrazol-3-yl)quinazolin-4-amine as a colorless solid (51 mg, 16%). $^1$H NMR (300 MHz, DMSO-$d_6$) δ 12.23 (br s, 1H), 10.87 (br s, 1H), 8.65-8.67 (m, 2H), 8.01-8.08 (m, 3H), 7.61 (dd, J=9, 6 Hz, 1H), 5.94 (s, 1H), 2.17 (s, 3H). LCMS (ESI) m/z 405 (M+H)$^+$.

Example 14

Preparation of 2-(difluoro(5-fluoropyridin-2-yl)methyl)-7-methyl-N-(5-methyl-1H-pyrazol-3-yl)quinazolin-4-amine

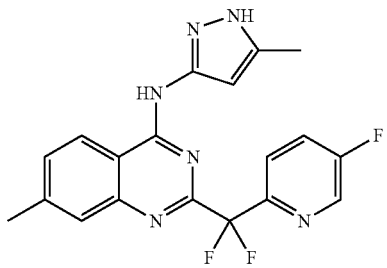 [SMILES: Cc1ccc2c(Nc3cc(C)[nH]n3)nc(C(F)(F)c3ccc(F)cn3)nc2c1]

Step A:
To a mixture of 2-amino-4-methylbenzamide (804 mg, 5.36 mmol) and sodium 2,2-difluoro-2-(5-fluoropyridin-2-yl)acetate from Example 2 Step B (1.25 g, 5.89 mmol) was added trimethylsilyl polyphosphate (ca. 10 mL) and the mixture was heated at 130° C. in a sand bath overnight. The mixture was allowed to cool to rt, and then water (75 mL) and EtOAc (75 mL) were added and the mixture was stirred at rt for 1 h. The organic layer was separated, washed with brine, dried over Na$_2$SO$_4$, filtered and concentrated under reduced pressure. The residue was purified by silica gel chromatography eluting with 0-60% EtOAc/hexanes to afford 2-(difluoro(5-fluoropyridin-2-yl)methyl)-7-methylquinazolin-4-ol (1.09 g, 66%). LCMS (ESI) m/z 306 (M+H)$^+$.

Step B:
To 2-(difluoro(5-fluoropyridin-2-yl)methyl)-7-methylquinazolin-4-ol (413 mg, 1.35 mmol) were added Lawesson's reagent (820 mg, 2.03 mmol) and pyridine (3.5 mL), and the mixture was heated at 170° C. in a microwave reactor for 20 min. The mixture was partitioned between EtOAc (30 mL) and saturated aq NaHCO$_3$ (50 mL), and the separated aqueous phase was extracted with EtOAc (2×30 mL). The combined organic layers were washed with 2N HCl and brine, dried over Na$_2$SO$_4$, and concentrated under reduced pressure onto Celite. The mixture was purified by silica gel chromatography eluting with 0-30% EtOAc/hexanes to afford 2-(difluoro(5-fluoropyridin-2-yl)methyl)-7-methylquinazoline-4-thiol as an impure mixture (0.249 g). LCMS (ESI) m/z 322 (M+H)$^+$.

Step C:
To a solution of 2-(difluoro(5-fluoropyridin-2-yl)methyl)-7-methylquinazoline-4-thiol (243 mg, ~0.75 mmol) in isopropanol (5 mL) was added 1N NaOH (1.13 mL, 1.13 mmol), and the mixture was stirred at rt for 5 min. Iodomethane (0.06 mL, 0.90 mmol) was then added and the mixture was stirred at room temperature for 5 min. The mixture was concentrated under reduced pressure to afford a yellow solid that was collected and washed with water and methanol to afford 2-(difluoro(5-fluoropyridin-2-yl)methyl)-7-methyl-4-(methylthio)quinazoline as a light yellow solid (152 mg, 60%). (M+H)$^+$. $^1$H NMR (300 MHz, DMSO-$d_6$) δ 8.57-8.66 (m, 1H), 7.93-8.12 (m, 3H), 7.85 (s, 1H), 7.62-7.71 (m, 1H), 2.56 (s, 3H), 2.53 (s, 3H). LCMS (ESI) m/z 336 (M+H)$^+$.

Step D:
To a solution of 2-(difluoro(5-fluoropyridin-2-yl)methyl)-7-methyl-4-(methylthio)quinazoline (152 mg, 0.454 mmol) in DCM (3 mL) at 0° C. was added 70% meta-chloroperoxybenzoic acid (168 mg, 0.681 mmol), and the mixture was stirred for 40 min at 0° C. DCM (15 mL) was added and the mixture was washed with saturated aq NaHCO$_3$ (20 mL) and saturated aq sodium thiosulfate (20 mL), dried over Na$_2$SO$_4$, and concentrated under reduced pressure. To the residue (154 mg) was added 5-methyl-1H-pyrazol-3-amine (132 mg, 1.36 mmol) in THF (4 mL), and the mixture was stirred at rt overnight and then concentrated under reduced pressure. The residue was purified by reverse phase HPLC (Varian Diphenyl reverse phase column, eluting with a gradient of solvent B=0.05% HOAc/ACN and solvent A=0.05% HOAc/5% ACN/H$_2$O) to afford 2-(difluoro(5-fluoropyridin-2-yl)methyl)-7-methyl-N-(5-methyl-1H-pyrazol-3-yl)quinazolin-4-amine (62.3 mg, 36%). $^1$H NMR (300 MHz, DMSO-$d_6$) δ 12.08-12.20 (m, 1H), 10.53-10.66 (m, 1H), 8.66 (s, 1H), 8.57 (d, J=8.7 Hz, 1H), 7.93-8.03 (m, 2H), 7.66 (s, 1H), 7.48 (d, J=7.5 Hz, 1H), 5.99 (s, 1H), 2.51 (s, 4H), 2.18 (s, 3H). LCMS (ESI) m/z 386 (M+H)$^+$.

Example 15

Preparation of 2-(difluoro(5-fluoropyridin-2-yl)methyl)-7-fluoro-N-(5-methyl-1H-pyrazol-3-yl)quinazolin-4-amine

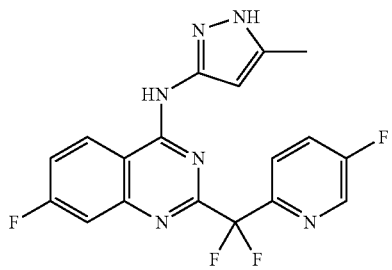 [SMILES: Cc1cc(Nc2nc(C(F)(F)c3ccc(F)cn3)nc3cc(F)ccc23)n[nH]1]

Step A:
2-(Difluoro(5-fluoropyridin-2-yl)methyl)-7-fluoroquinazolin-4-ol (1.05 g, 58%) was obtained as an orange solid using a procedure analogous to that described in Example 14 Step A, substituting 2-amino-4-fluorobenzamide for the 2-amino-4-methylbenzamide used in Example 14. LCMS (ESI) m/z 310 (M+H)$^+$.

Step B:
2-(Difluoro(5-fluoropyridin-2-yl)methyl)-7-fluoroquinazoline-4-thiol (203 mg, 39%) was obtained as a yellow solid using a procedure analogous to that described in Example 14 Step B, substituting 2-(difluoro(5-fluoropyridin-2-yl)methyl)-7-fluoroquinazolin-4-ol for the 2-(difluoro(5-fluoropyridin-2-yl)methyl)-7-methylquinazolin-4-ol used in Example 14. LCMS (ESI) m/z 326 (M+H)$^+$.

Step C:

2-(Difluoro(5-fluoropyridin-2-yl)methyl)-7-fluoro-4-(methylthio)quinazoline (148 mg, 72%) was obtained as an orange solid using a procedure analogous to that described in Example 14 Step C, substituting 2-(difluoro(5-fluoropyridin-2-yl)methyl)-7-fluoroquinazoline-4-thiol for the 2-(difluoro(5-fluoropyridin-2-yl)methyl)-7-methylquinazoline-4-thiol used in Example 14. $^1$H NMR (300 MHz, DMSO-$d_6$) δ 8.62 (d, J=2.6 Hz, 1H), 8.27 (d, J=5.8 Hz, 1H), 7.94-8.12 (m, 2H), 7.85-7.93 (m, 1H), 7.69-7.80 (m, 1H), 2.55 (s, 3H). LCMS (ESI) m/z 340 (M+H)$^+$.

Step D:

2-(Difluoro(5-fluoropyridin-2-yl)methyl)-7-fluoro-N-(5-methyl-1H-pyrazol-3-yl)quinazolin-4-amine (40.7 mg, 24%) was obtained as a white solid using a procedure analogous to that described in Example 14 Step D, substituting 2-(difluoro(5-fluoropyridin-2-yl)methyl)-7-fluoro-4-(methylthio)quinazoline for the 2-(difluoro(5-fluoropyridin-2-yl)methyl)-7-methyl-4-(methylthio)quinazoline used in Example 14. $^1$H NMR (300 MHz, DMSO-$d_6$) δ 12.16-12.25 (m, 1H), 10.81 (s, 1H), 8.79 (dd, J=6.0, 9.0 Hz, 1H), 8.67 (s, 1H), 7.97-8.04 (m, 2H), 7.53-7.69 (m, 2H), 5.97 (s, 1H), 2.17 (s, 3H). LCMS (ESI) m/z 389 (M+H)$^+$.

Example 16

Preparation of 7-chloro-2-(difluoro(5-fluoropyridin-2-yl)methyl)-N-(5-methyl-1H-pyrazol-3-yl)quinazolin-4-amine

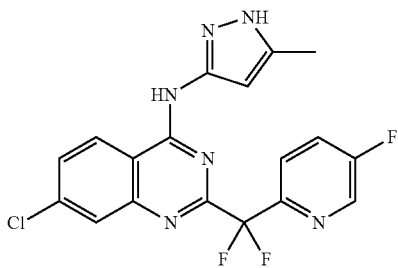 [SMILES: Cc1cc(Nc2nc(C(F)(F)c3ccc(F)cn3)nc3cc(Cl)ccc23)n[nH]1]

Step A:

2-(Difluoro(5-fluoropyridin-2-yl)methyl)-7-chloroquinazolin-4-ol (0.657 g, 46%) was obtained as an yellow solid using a procedure analogous to that described in Example 14 Step A, substituting 2-amino-4-chlorobenzamide for the 2-amino-4-methylbenzamide used in Example 14. LCMS (ESI) m/z 326 (M+H)$^+$.

Step B:

7-Chloro-2-(difluoro(5-fluoropyridin-2-yl)methyl)quinazoline-4-thiol (452 mg, 81%) was obtained as a yellow solid using a procedure analogous to that described in Example 14 Step B, substituting 7-chloro-2-(difluoro(5-fluoropyridin-2-yl)methyl)quinazolin-4-ol for the 2-(difluoro(5-fluoropyridin-2-yl)methyl)-7-methylquinazolin-4-ol used in Example 14. LCMS (ESI) m/z 342 (M+H)$^+$.

Step C:

7-Chloro-2-(difluoro(5-fluoropyridin-2-yl)methyl)-4-(methylthio)quinazoline (196 mg, 46%) was obtained as an orange solid using a procedure analogous to that described in Example 14 Step C, substituting 7-chloro-2-(difluoro(5-fluoropyridin-2-yl)methyl)quinazoline-4-thiol for the 2-(difluoro(5-fluoropyridin-2-yl)methyl)-7-methylquinazoline-4-thiol used in Example 14. $^1$H NMR (300 MHz, DMSO-$d_6$) δ 8.58-8.65 (m, 1H), 8.15-8.24 (m, 2H), 7.92-8.11 (m, 2H), 7.83-7.88 (m, 1H), 2.55 (s, 3H). LCMS (ESI) m/z 356 (M+H)$^+$.

Step D:

7-Chloro-2-(difluoro(5-fluoropyridin-2-yl)methyl)-N-(5-methyl-1H-pyrazol-3-yl)quinazolin-4-amine (40.7 mg, 18%) was obtained as a white solid using a procedure analogous to that described in Example 14 Step D, substituting 7-chloro-2-(difluoro(5-fluoropyridin-2-yl)methyl)-4-(methylthio)quinazoline for 2-(difluoro(5-fluoropyridin-2-yl)methyl)-7-methyl-4-(methylthio)quinazoline used in Example 14. $^1$H NMR (300 MHz, DMSO-$d_6$) δ 12.17-12.26 (m, 1H), 10.80-10.91 (m, 1H), 8.62-8.78 (m, 2H), 7.90-8.06 (m, 3H), 7.70 (dd, J=1.9, 8.9 Hz, 1H), 5.97 (s, 1H), 2.17 (s, 3H). LCMS (ESI) m/z 405 (M+H)$^+$.

Example 17

Preparation of (R,S)-2-((5-fluoropyridin-2-yl)(methoxy)methyl)-N-(5-methyl-1H-pyrazol-3-yl)quinazolin-4-amine

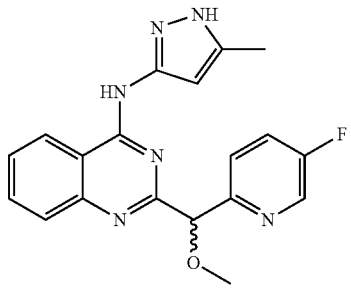 [SMILES: COC(c1ccc(F)cn1)c1nc(Nc2cc(C)[nH]n2)c2ccccc2n1]

Step A:

Sodium 2-(5-fluoropyridin-2-yl)acetate is prepared following a procedure analogous to that described in Example 2 Steps A and B, substituting ethyl bromoacetate for the ethyl 2-bromo-2,2-difluoroacetate used in Example 2.

Step B:

Sodium 2-(5-fluoropyridin-2-yl)acetate is treated with 1-1.5 equiv of $Br_2$ in the presence of phosphorus tribromide under standard Hell-Volhard-Zelinskii reaction conditions (J. March "Advanced Organic Chemistry" 3$^{rd}$ Edition, 1985, p. 531 and references therein) to afford 2-bromo-2-(5-fluoropyridin-2-yl)acetic acid.

Step C:

To a 0.5 M solution of 2-bromo-2-(5-fluoropyridin-2-yl)acetic acid in 99:1 DCM/DMF is added oxalyl chloride (1.2 equiv) and the mixture is allowed to stir at rt for 30 min or until the reaction is substantially complete. The mixture is then cooled to 0° C. and 2-aminobenzamide (1 equiv) in pyridine (2 mL) is added slowly, and the mixture is allowed to warm to rt over ca. 1 h. The mixture is concentrated under reduced pressure and the residue is purified by chromatography to afford 2-(2-bromo-2-(5-fluoropyridin-2-yl)acetamido)benzamide.

Step D:

To a 0.3 M solution of 2-(2-bromo-2-(5-fluoropyridin-2-yl)acetamido)benzamide in MeOH is added 25% sodium methoxide/MeOH (2 equiv) and the mixture is heated at 65° C. overnight or until the reaction is substantially complete. The mixture is concentrated under reduced pressure and the residue is purified by chromatography to afford 2-((5-fluoropyridin-2-yl)(methoxy)methyl)quinazolin-4-ol.

Step E:

(R,S)-2-((5-fluoropyridin-2-yl)(methoxy)methyl)-N-(5-methyl-1H-pyrazol-3-yl)quinazolin-4-amine is prepared following a procedure analogous to that described in Example 14 Steps B-D, substituting 2-((5-fluoropyridin-2-yl)(methoxy)methyl)quinazolin-4-ol for the 2-(difluoro(5-fluoropyridin-2-yl)methyl)-7-methylquinazolin-4-ol used in Example 14.

Example 18

Preparation of (R,S)-2-(amino(5-fluoropyridin-2-yl)methyl)-N-(5-methyl-1H-pyrazol-3-yl)quinazolin-4-amine

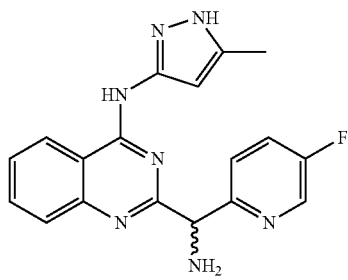 [SMILES: Cc1cc(Nc2nc(C(N)c3ccc(F)cn3)nc3ccccc23)n[nH]1]

Step A:
To a 0.3 M solution of (5-fluoropyridin-2-yl)(4-(5-methyl-1H-pyrazol-3-ylamino)quinazolin-2-yl)methanone from Example 1 in EtOH is added methoxylamine hydrochloride (2 equiv) and the mixture is heated to 60° C. for 30 min or until the reaction is substantially complete. The mixture is concentrated under reduced pressure and the residue is purified by chromatography to afford (5-fluoropyridin-2-yl)(4-(5-methyl-1H-pyrazol-3-ylamino)quinazolin-2-yl)methanone O-methyl oxime. LC-MS (ESI) m/z 377 (M+H)$^+$.

Step B:
To a 0.3 M solution of (5-fluoropyridin-2-yl)(4-(5-methyl-1H-pyrazol-3-ylamino)quinazolin-2-yl)methanone O-methyl oxime in acetic acid (25 mL) is added zinc dust (20 equiv) and the mixture is stirred at rt overnight then filtered through Celite. The filtrate is concentrated and the residue is purified by reverse-phase HPLC to afford (R,S)-2-(amino(5-fluoropyridin-2-yl)methyl)-N-(5-methyl-1H-pyrazol-3-yl)quinazolin-4-amine.

Example 19

Preparation of (R,S)-methyl (5-fluoropyridin-2-yl)(4-(5-methyl-1H-pyrazol-3-ylamino)quinazolin-2-yl)methylcarbamate

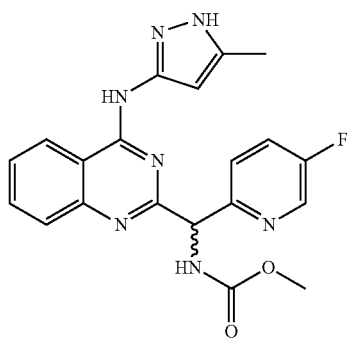 [SMILES: COC(=O)NC(c1ccc(F)cn1)c1nc(Nc2cc(C)[nH]n2)c2ccccc2n1]

To a 0.3 M solution of (R,S)-2-(amino(5-fluoropyridin-2-yl)methyl)-N-(5-methyl-1H-pyrazol-3-yl)quinazolin-4-amine (0.105 g, 0.3 mmol) in dry THF at 0° C. are added methyl chloroformate (1 equiv) dropwise and DIEA (1.2 equiv) and the mixture is stirred at 0° C. for 10 min and at rt for 5 min or until the reaction is substantially complete. The mixture is concentrated under reduced pressure and the residue is purified by reverse-phase HPLC to afford (R,S)-methyl (5-fluoropyridin-2-yl)(4-(5-methyl-1H-pyrazol-3-ylamino)quinazolin-2-yl)methylcarbamate

Example 20

Preparation of methyl 2-(difluoro(5-fluoropyridin-2-yl)methyl)-4-(5-methyl-1H-pyrazol-3-ylamino)quinazoline-7-carboxylate

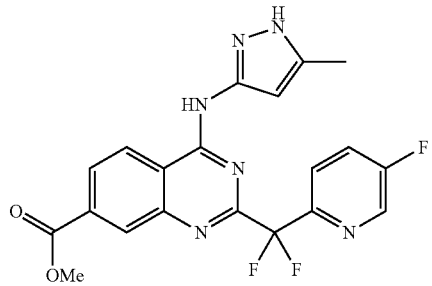 [SMILES: COC(=O)c1ccc2c(Nc3cc(C)[nH]n3)nc(C(F)(F)c3ccc(F)cn3)nc2c1]

Step A:
A mixture of 4-(methoxycarbonyl)-3-nitrobenzoic acid (200 mg) and concentrated NH$_4$OH (30 mL) in sealed tube was heated at 105° C. overnight. After cooling to rt the mixture was concentrated under reduced pressure and then 2N HCl (5 mL) was added. The mixture was extracted with EtOAc (3×50 mL) and the combined organic extracts were washed with brine (50 mL), dried over Na$_2$SO$_4$, filtered and concentrated under reduced pressure. To the residue in MeOH (20 mL) was added dropwise thionyl chloride (0.2 mL), and the mixture was heated at reflux for 6 h. The mixture was concentrated under reduced pressure, and the residue was partitioned between saturated aq NaHCO3 (50 mL) and EtOAc (50 mL), the separated aqueous phase was extracted with EtOAc (2×50 mL). The combined organic layers were washed with brine (50 mL), dried over Na$_2$SO$_4$, filtered, and concentrated under reduced pressure. To the residue in EtOH (30 mL) was add 10% Pd/C (10 mg), and the mixture was stirred at rt under H$_2$ (1 atm) for 4 h. The mixture was filtered through Celite washing with MeOH. The filtrate was concentrated under reduced pressure and the residue was purified by silica gel chromatography eluting with 5% MeOH/DCM to afford methyl 3-amino-4-carbamoylbenzoate as a white solid (142 mg, 82.5%). $^1$H NMR (300 MHz, DMSO-d$_6$) δ 3.82 (s, 3H), 6.75 (s, 2H), 7.01 (d, 1H), 7.28 (s, 1H), 7.34 (s, 1H), 7.62 (d, 1H) 7.89 (s, 1H); LC-MS (ESI) m/z 211 (M+H)$^+$.

Step B:
Methyl 2-(difluoro(5-fluoropyridin-2-yl)methyl)-4-(5-methyl-1H-pyrazol-3-ylamino)quinazoline-7-carboxylate is prepared using a procedure analogous to that described in Example 14, substituting methyl 3-amino-4-carbamoylbenzoate for the 2-amino-4-methylbenzamide used in Example 14.

Example 21

Preparation of (2-(difluoro(5-fluoropyridin-2-yl)methyl)-4-(5-methyl-1H-pyrazol-3-ylamino)quinazolin-7-yl)methanol

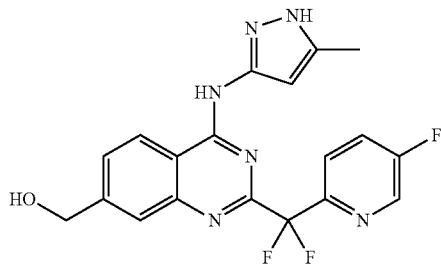 [SMILES: Cc1cc(Nc2nc(C(F)(F)c3ccc(F)cn3)nc3cc(CO)ccc23)n[nH]1]

To a suspension of lithium aluminum hydride (LAH, 3 equiv) in THF at 0° C. is slowly added a suspension of methyl 2-(difluoro(5-fluoropyridin-2-yl)methyl)-4-(5-methyl-1H-pyrazol-3-ylamino)quinazoline-7-carboxylate (1 equiv) in THF. The mixture is stirred at 0° C. for 0.5 h and then at rt for 4 h. To the stirring mixture at 0° C. are added successively in dropwise fashion water (1 mL per g of LAH), 15% NaOH (1 mL per g of LAH), and water (3 mL per gram of LAH) and the mixture is stirred at rt overnight. The mixture is filtered through Celite washing with 20% MeOH/DCM (500 mL), and the filtrate is concentrated under reduced pressure. The residue is purified by reverse phase HPLC to afford (2-(difluoro(5-fluoropyridin-2-yl)methyl)-4-(5-methyl-1H-pyrazol-3-ylamino)quinazolin-7-yl)methanol.

Example 22

Preparation of 2-(difluoro(5-fluoropyridin-2-yl)methyl)-N-(5-methyl-1H-pyrazol-3-yl)-7-(methylsulfonylmethyl)quinazolin-4-amine

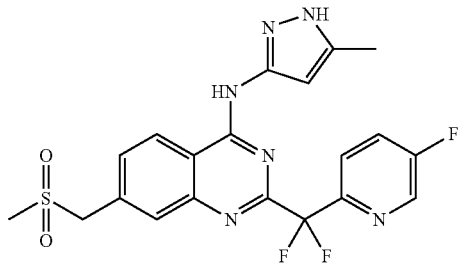 [SMILES: Cc1cc(Nc2nc(C(F)(F)c3ccc(F)cn3)nc3cc(CS(C)(=O)=O)ccc23)n[nH]1]

To a suspension of (2-(difluoro(5-fluoropyridin-2-yl)methyl)-4-(5-methyl-1H-pyrazol-3-ylamino)quinazolin-7-yl)methanol from Example 21 in DCM at reflux temperature is added PBr$_3$ (2 equiv). Heating is continued for 30-60 min, then after cooling to rt the mixture is concentrated under reduced pressure. Then DMF and sodium thiomethoxide (5 equiv) are added, and the mixture is stirred at rt for 2 d. Saturated aq NaHCO$_3$ is added, and the mixture is extracted with EtOAc. The combined organic layers are washed with brine, dried over Na$_2$SO$_4$, filtered, and concentrated under reduced pressure. To the residue in DCM is added 4-chloroperbenzoic acid (10 equiv) and the mixture is stirred at rt for 4 h. Saturated aq NaHCO$_3$ is added and the mixture is extracted with DCM. The combined organic layers are washed with brine, dried over Na$_2$SO$_4$, filtered, and concentrated. The residue is purified by reverse phase HPLC to afford 2-(difluoro(5-fluoropyridin-2-yl)methyl)-N-(5-methyl-1H-pyrazol-3-yl)-7-(methylsulfonylmethyl)quinazolin-4-amine.

Example 23

Preparation of 2-(2-(5-fluoropyridin-2-yl)-1,3-dioxolan-2-yl)-N-(5-methyl-1H-pyrazol-3-yl)quinazolin-4-amine

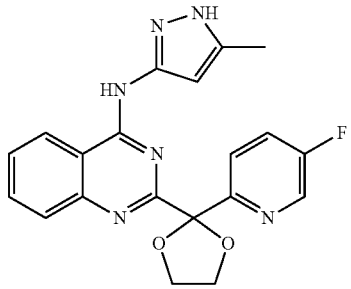 [SMILES: Cc1cc(Nc2nc(C3(c4ccc(F)cn4)OCCO3)nc3ccccc23)n[nH]1]

To a mixture of (5-fluoropyridin-2-yl)(4-(5-methyl-1H-pyrazol-3-ylamino)quinazolin-2-yl)methanone from Example 1 and toluene are added ethylene glycol 5 equiv) and p-toluenesulfonic acid monohydrate (0.2 equiv), and the mixture is heated at reflux while collecting water in a Dean-Stark trap. As needed, additional ethylene glycol and p-toluenesulfonic acid monohydrate are added and heating and water collection are continued to achieve substantially complete reaction After cooling to rt, the mixture is concentrated, and the residue is dissolved in DMSO and purified by reverse phase HPLC.

Example 24

Preparation of (R,S)—N-((5-fluoropyridin-2-yl)(4-(5-methyl-1H-pyrazol-3-ylamino)quinazolin-2-yl)methyl)formamide

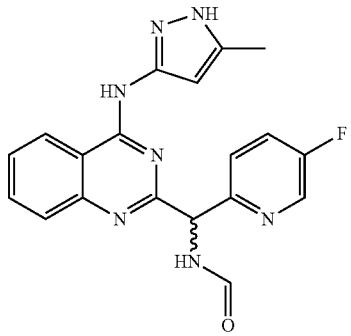 [SMILES: Cc1cc(Nc2nc(C(NC=O)c3ccc(F)cn3)nc3ccccc23)n[nH]1]

To (R,S)-2-(amino(5-fluoropyridin-2-yl)methyl)-N-(5-methyl-1H-pyrazol-3-yl)quinazolin-4-amine from Example 18 in ethyl formate are added TEA (10 equiv) and EtOH (20 equiv), and the mixture is heated in a microwave reactor at 120° C. for 30 min or until the reaction is substantially complete. The mixture is concentrated under reduced pressure and the residue is diluted with DMSO and purified by reverse phase HPLC to afford N-((4-fluorophenyl)(4-(5-methyl-1H-pyrazol-3-ylamino)quinazolin-2-yl)methyl)formamide.

Example 25

Preparation of (R,S)-3-(5-fluoropyridin-2-yl)-3-(4-(5-methyl-1H-pyrazol-3-ylamino)quinazolin-2-yl)propanenitrile

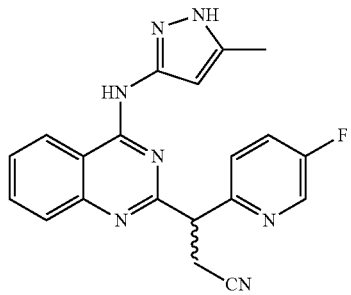 [SMILES: Cc1cc(Nc2nc(C(CC#N)c3ccc(F)cn3)nc3ccccc23)n[nH]1]

To a suspension of 60% sodium hydride/mineral oil (3 equiv) in THF at 0° C. under Ar was added diethyl cyanomethylphosphonate (3 equiv) and the mixture was stirred for 10 min. Then (5-fluoropyridin-2-yl)(4-(5-methyl-1H-pyrazol-3-ylamino)quinazolin-2-yl)methanone from Example 1 (1 equiv) is added and the mixture is stirred at rt for 0.5-3 h, or until the reaction is substantially complete. Then AcOH (5 equiv) and Celite are added and the mixture is concentrated under reduced pressure. The mixture is eluted onto a silica gel column and further eluted with EtOAc/hexanes. To the isolated material is added EtOH (100 mL) and 10% Pd—C (180 mg) and the mixture is heated at 70° C. under a hydrogen atmosphere, with addition of more catalyst and additional heating as required to effect substantially complete reaction. The mixture is concentrated and purified by chromatography to afford (R,S)-3-(5-fluoropyridin-2-yl)-3-(4-(5-methyl-1H-pyrazol-3-ylamino)quinazolin-2-yl)propanenitrile.

Example 26

Preparation of (R,S)-2-((cyclopropylamino)(5-fluoropyridin-2-yl)methyl)-N-(5-methyl-1H-pyrazol-3-yl)quinazolin-4-amine

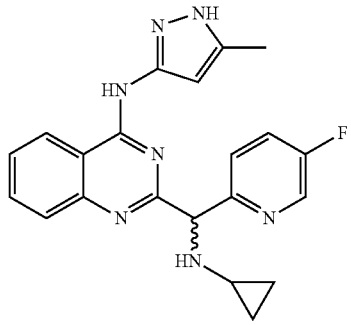 [SMILES: Cc1cc(Nc2nc(C(NC3CC3)c3ccc(F)cn3)nc3ccccc23)n[nH]1]

To (5-fluoropyridin-2-yl)(4-(5-methyl-1H-pyrazol-3-ylamino)quinazolin-2-yl)methanone from Example 1 (1 equiv) in 2-propanol are added cyclopropylamine (5 equiv) and 3 Å(8-12 mesh) molecular sieves, and the mixture is heated at 140° C. in a microwave reactor. Additional cyclopropylamine is added and microwave or conventional heating is continued until the reaction is substantially complete according to NMR. Then a suspension of sodium borohydride (10 equiv) in 2-propanol is added and the mixture is stirred at rt. Methanol, additional sodium borohydride, and traces of HOAc are added as necessary until the reaction is substantially complete, then the mixture is filtered and the filtrate is concentrated. DMSO is added and the mixture is purified by preparative HPLC to afford 2-((cyclopropylamino)(5-fluoropyridin-2-yl)methyl)-N-(5-methyl-1H-pyrazol-3-yl)quinazolin-4-amine.

Example 27

Preparation of (R,S)-2-(1-(5-fluoropyridin-2-yl)-2-(methylsulfonyl)ethyl)-N-(5-methyl-1H-pyrazol-3-yl)quinazolin-4-amine

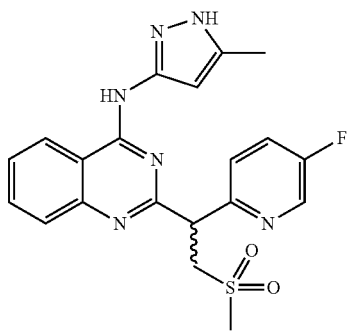 [SMILES: Cc1cc(Nc2nc(C(CS(C)(=O)=O)c3ccc(F)cn3)nc3ccccc23)n[nH]1]

Step A:

To 3-chlorobenzoperoxoic acid (77%, 11.21 g, 50 mmol) in DCM (150 mL) was added diethyl methylthiomethylphosphonate (4.4 mL, 25 mmol) and the mixture was allowed to stir at rt overnight. Additional 3-chlorobenzoperoxoic acid (5.6 g) was then added and stirring was continued for 4 h at rt. The solution was washed with saturated aq potassium carbonate and concentrated. The residue was dissolved in DCM and washed again with a saturated potassium carbonate solution. The organic layer was concentrated to afford diethyl methylsulfonylmethylphosphonate (4.51 g, 39%). $^1$H NMR (300 MHz, DMSO-$d_6$) δ 1.25 (t, 6H) 3.13 (s, 3H) 4.09 (m, 4H) 4.20 (d, 2H); LC-MS (ESI) m/z 231 (M+H)$^+$.

Step B:

To diethyl methylsulfonylmethylphosphonate (746 mg, 3.24 mmol) in THF (20 mL) at 0° C. was added potassium t-butoxide (1.0 M in THF, 3.25 mL, 3.25 mmol) and the mixture was stirred for 5 min. Then (5-fluoropyridin-2-yl)(4-(5-methyl-1H-pyrazol-3-ylamino)quinazolin-2-yl)methanone from Example 1 (1 mmol) is added and the mixture is stirred at rt for 4 to 8 h or until the reaction is substantially complete. After acidic aqueous workup, the crude product is purified by silica gel chromatography. The isolated product in an EtOAc/EtOH mixture is then hydrogenated in the presence of 10% Pd—C. Additional catalyst is added and the reaction is allowed to continue as needed until the reaction is substantially complete. The mixture is filtered and the filtrate is concentrated under reduced pressure. The residue is purified by chromatography to afford (R,S)-2-(1-(5-fluoropyridin-2-yl)-2-(methylsulfonyl)ethyl)-N-(5-methyl-1H-pyrazol-3-yl)quinazolin-4-amine.

Example 28

Preparation of (R,S)-2-(3-amino-1-(5-fluoropyridin-2-yl)propyl)-N-(5-methyl-1H-pyrazol-3-yl)quinazolin-4-amine

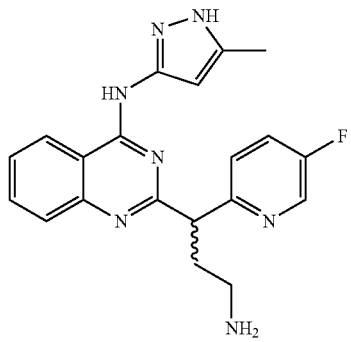 [SMILES: Cc1cc(Nc2nc(C(CCN)c3ccc(F)cn3)nc3ccccc23)n[nH]1]

To (R,S)-3-(5-fluoropyridin-2-yl)-3-(4-(5-methyl-1H-pyrazol-3-ylamino)quinazolin-2-yl)propanenitrile from Example 25 (1 equiv) in THF at 0° C. is added lithium aluminum hydride (2 equiv) and the mixture is stirred for 5 min at 0° C. and then allowed to warm to rt and stir for 2-3 h. Additional lithium aluminum hydride is added and stirring is continued as needed until the reaction is substantially complete. To the solution are slowly and successively added 1 N NaOH (1 part), H$_2$O (1 part), and 1 N NaOH (3 parts), and the mixture is stirred for several hours and then filtered. The filtrate is concentrated under reduced pressure and purified by reverse phase HPLC to afford (R,S)-2-(3-amino-1-(5-fluoropyridin-2-yl)propyl)-N-(5-methyl-1H-pyrazol-3-yl)quinazolin-4-amine.

Example 29

Preparation of (3-methoxypyridin-2-yl)(4-(5-methyl-1H-pyrazol-3-ylamino)quinazolin-2-yl)methanone

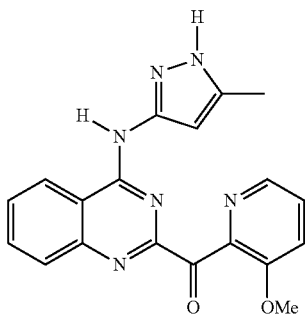 [SMILES: COc1cccnc1C(=O)c1nc(Nc2cc(C)[nH]n2)c2ccccc2n1]

(3-Methoxypyridin-2-yl)(4-(5-methyl-1H-pyrazol-3-ylamino)quinazolin-2-yl)methanone is prepared using a procedure analogous to that reported in Example 1, substituting 2-bromo-3-methoxypyridine (Watterson, et al., J. Med. Chem. 2007, 50, 3730-3742) for the 2-bromo-5-fluoropyridine used in Example 1.

Example 30

Preparation of N-(2-(difluoro(5-fluoropyridin-2-yl)methyl)quinazolin-4-yl)-5-methylthiazol-2-amine

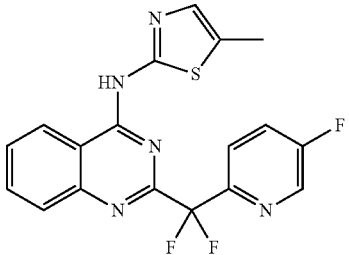 [SMILES: Cc1cnc(Nc2nc(C(F)(F)c3ccc(F)cn3)nc3ccccc23)s1]

Step A:

To a mixture of 4-chloro-2-(difluoro(5-fluoropyridin-2-yl)methyl)quinazoline from Example 4 Step A (100 mg, 0.32 mmol), Pd$_2$(dibenzylideneacetone)$_3$ (12 mg, 0.013 mmol), 4,5-Bis(diphenylphosphino)-9,9-dimethylxanthene (23 mg, 0.04 mmol), 5-methylthiazol-2-amine (51 mg, 0.45 mmol), and Na$_2$CO$_3$ (48 mg, 0.45 mmol) was added toluene (3 mL). The mixture was evacuated and flushed with argon three times and then heated at 110° C. for 2 h. The mixture was diluted with MeOH, filtered, and the filtrate was concentrated under reduced pressure. The residue was purified by preparative HPLC (Varian diphenyl reverse phase column, eluted with gradient of solvent B=0.05% HOAC/ACN and solvent A=0.05% HOAc/H$_2$O) to afford N-(2-(difluoro(5-fluoropyridin-2-yl)methyl)quinazolin-4-yl)-5-methylthiazol-2-amine (6 mg, 5%). $^1$H NMR (300 MHz, DMSO-d$_6$) δ 12.45 (br s, 1H), 8.64 (d, J=2.4 Hz, 2H), 7.88-8.15 (m, 4H), 7.66-7.76 (m, 1H), 7.19 (s, 1H), 2.28 (s, 3H). LCMS (ESI) m/z 388 (M+H)$^+$.

Example 31

Preparation of 2-(difluoro(5-fluoropyridin-2-yl)methyl)-N-(1H-1,2,4-triazol-3-yl)quinazolin-4-amine

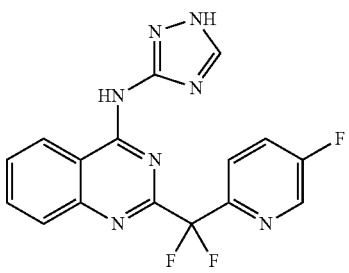 [SMILES: Fc1ccc(C(F)(F)c2nc(Nc3nc[nH]n3)c3ccccc3n2)nc1]

Step A:

To a solution of 3-nitro-1H-1,2,4-triazole (0.5 g, 4.38 mmol) in anhydrous DMF (20 mL) was added potassium carbonate (0.67 g, 4.82 mmol), and the mixture was stirred at rt for 10 min and then (2-(chloromethoxy)ethyl)trimethylsilane (0.73 g, 4.38 mmol) was added. The mixture was stirred at rt for 1 h and then partitioned between EtOAc (100 mL) and water (100 mL). The aqueous layer was separated and extracted with ethyl acetate (2×50 mL). The combined organic layers were washed with brine (2×100 mL), dried over anhydrous magnesium sulfate, filtered, and concentrated under reduced pressure. The crude product was purified by silica gel chromatography eluting with 0-50% EtOAc/hexanes to afford colorless crystals, which were triturated with diethyl ether to afford a single isomer of SEM-protected 3-nitro-1,2,4-triazole (SEM=(2-(trimethylsilyl)ethoxy)methyl)) as a white solid (0.58 g, 54%). $^1$H NMR (300 MHz, DMSO-d$_6$) δ 9.09 (s, 1H), 5.69 (s, 2H), 3.58-3.75 (m, 2H), 0.84-0.99 (m, 2H), 0.00 (s, 9H).

Step B:
A vessel containing SEM-protected 3-nitro-1,2,4-triazole (0.58 g, 2.37 mmol) in anhydrous ethanol (15 mL) was evacuated and flushed with argon several times, and then a catalytic amount of 10% palladium on activated carbon was added. The mixture was stirred under a hydrogen atmosphere at rt for 1 h, and then filtered through Ccelite. The filtrate was concentrated under reduced pressure to afford a single isomer of SEM protected 1,2,4-triazol-3-amine as an off-white solid (0.45 g, 89%). $^1$H NMR (300 MHz, DMSO-d$_6$) δ 8.16 (s, 1H), 5.29-5.42 (m, 2H), 5.24 (s, 2H), 3.56 (t, J=8.1 Hz, 2H), 0.87 (t, J=8.0 Hz, 2H), 0.00 (s, 9H). LC-MS (ESI) m/z 215 (M+H)$^+$.

Step C:
To a mixture of 4-chloro-2-(difluoro(5-fluoropyridin-2-yl)methyl)quinazoline from Example 4 Step A (100 mg, 0.32 mmol), Pd$_2$(dibenzylideneacetone)$_3$ (12 mg, 0.013 mmol), 4,5-Bis(diphenylphosphino)-9,9-dimethylxanthene (23 mg, 0.04 mmol), SEM protected 1,2,4-triazol-3-amine (97 mg, 0.45 mmol), and Na$_2$CO$_3$ (48 mg, 0.45 mmol) was added toluene (3 mL), and the mixture was evacuated and flushed with argon three times. The mixture was heated at 110° C. for 2 h, and then diluted with DCM and filtered. To the filtrate was added TFA (3 mL) and the mixture was stirred at rt for 2 h and then concentrated under reduced pressured. To the residue was added MeOH and the mixture was concentrated under reduced pressure. The residue was purified by preparative HPLC (Phenomenex C-18 reverse phase column eluting with gradient of solvent B=0.05% HOAC/ACN and solvent A=0.05% HOAc/H$_2$O). The obtained material was triturated with diethyl ether to afford 2-(difluoro(5-fluoropyridin-2-yl)methyl)-N-(1H-1,2,4-triazol-3-yl)quinazolin-4-amine (16 mg, 14%). $^1$H NMR (300 MHz, methanol-d$_4$) δ 8.68 (br s, 1H), 8.50 (d, J=8.3 Hz, 1H), 7.90-8.15 (m, 4H), 7.71-7.88 (m, 2H). LCMS (ESI) m/z 358 (M+H)$^+$.

Example 32

Preparation of 2-(difluoro(5-fluoropyridin-2-yl)methyl)-N-(1-methyl-1H-imidazol-4-yl)quinazolin-4-amine

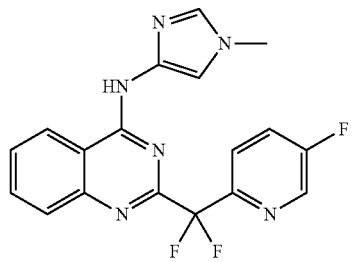 [SMILES: Cn1cnc(Nc2nc(C(F)(F)c3ccc(F)cn3)nc3ccccc23)c1]

Step A:
To a mixture of 4-nitro-1H-imidazole (2.0 g, 17.7 mmol) and K$_2$CO$_3$ (3.67 g, 26.6 mmol) in acetonitrile (18 mL) was added iodomethane (1.32 mL, 21.2 mmol) and the mixture was heated in a sealed vial at 60° C. overnight. The mixture was filtered washing with acetone. The filtrate was concentrated under reduced pressure, and the residue was diluted with hot isopropanol and cooled, and the precipitated solid was collected by filtration. The solid was dissolved in chloroform and filtered, and the filtrate was concentrated under reduced pressure. The residue was triturated with propan-2-ol and collected by filtration to afford 1-methyl-4-nitro-1H-imidazole (1.03 g, 46%) as a tan solid. $^1$H NMR (300 MHz, DMSO-d$_6$) δ 8.37 (d, J=1.1 Hz, 1H), 7.82 (s, 1H), 3.76 (s, 3H).

Step B:
To 1-methyl-4-nitro-1H-imidazole (354 mg, 2.8 mmol) in EtOH (20 mL) was added 10% Pd—C (90 mg) and the mixture was stirred under a hydrogen atmosphere for 1.5 h. The mixture was filtered and the filtrate was concentrated under reduced pressure to afford 1-methyl-1H-imidazol-4-amine (250 mg, 92%) as a yellow oil that darkened upon standing. $^1$H NMR (300 MHz, DMSO-d$_6$) δ 7.05 (s, 1H), 6.08 (d, J=1.3 Hz, 1H), 4.06 (br s, 2H), 3.47 (s, 3H).

Step C:
2-(Difluoro(5-fluoropyridin-2-yl)methyl)-N-(1-methyl-1H-imidazol-4-yl)quinazolin-4-amine is prepared using a procedure analogous to that described in Example 30, substituting 1-methyl-1H-imidazol-4-amine for the methylthiazol-2-amine used in Example 30.

Example 33

Preparation of 2-(difluoro(5-fluoropyridin-2-yl)methyl)-N-(5-methyl-1H-pyrazol-3-yl)-8-(trifluoromethyl)quinazolin-4-amine

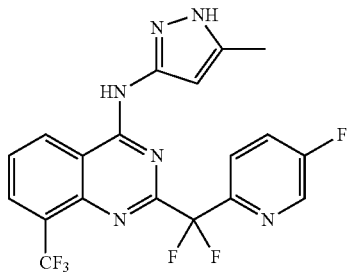

Step A:
To sodium 2,2-difluoro-2-(5-fluoropyridin-2-yl)acetate from Example 2 step B (1 g, 4.69 mmol) were added EtOAc (50 mL) and 4 N HCl (50 mL) and the mixture was shaken. The organic phase was separated, dried over sodium sulfate, and concentrated under reduced pressure to afford 2,2-difluoro-2-(5-fluoropyridin-2-yl)acetic acid (852 mg, 95%) as an oil that solidified upon standing. $^1$H NMR (300 MHz, DMSO-d$_6$) δ ppm 7.88-8.03 (m, 3H).

Step B:
To 2,2-difluoro-2-(5-fluoropyridin-2-yl)acetic acid (172 mg, 0.9 mmol) and 2-amino-3-(trifluoromethyl)benzoic acid (185 mg, 0.9 mmol) in pyridine (3 mL) was added triphenyl phosphite (0.26 mL, 1 mmol) and the mixture was heated in a microwave synthesizer at 150° C. for 10 min. The mixture was cooled to rt and then ethyl 3-aminopropanoate hydrochloride (156 mg, 1 mmol) was added and the mixture was heated in a microwave synthesizer at 180° C. for 3 min. The crude mixture was concentrated under reduced pressure. THF (6 mL) was added followed by sodium ethoxide (21% in EtOH, 1.2 mL) and the mixture was stirred at 50° C. for 1 h. An additional amount of sodium ethoxide (21% in EtOH, 1 mL) was added and the mixture was stirred at 70° C. for 45 min. The cooled mixture was then was partitioned between EtOAc and 4 N HCl and the organic phase was dried over sodium sulfate and concentrated under reduced pressure. The residue was dissolved in hexanes and Et$_2$O and concentrated under reduced pressure. The residue was then triturated with hexanes and collected by filtration to afford 2-(difluoro(5-fluoropyridin-2-yl)methyl)-8-(trifluoromethyl)quinazolin-4-ol (140 mg, 43%) as a brown solid. LC-MS (ESI) m/z 360 (M+H)$^+$.

Step C:

To 2-(difluoro(5-fluoropyridin-2-yl)methyl)-8-(trifluoromethyl)quinazolin-4-ol (121 mg, 0.34 mmol) were added phosphoryl tribromide (890 mg) and toluene (1 mL) followed by DIEA (0.117 mL, 0.67 mmol). The mixture was heated at 105° C. for 1 h. The mixture was cooled and partitioned between EtOAc and saturated aq sodium bicarbonate. The organic layer was dried over sodium sulfate and concentrated under reduced pressure. To the residue was added a solution of 5-methyl-1H-pyrazol-3-amine (150 mg, 1.5 mmol) in DMF (4 mL) and the mixture was stirred at rt for 1.5 h. The crude mixture was purified by preparative HPLC (Varian diphenyl reverse phase column, eluting with a gradient of solvent B=0.05% HOAc/ACN and solvent A=0.05% HOAc/H$_2$O) to afford 2-(difluoro(5-fluoropyridin-2-yl)methyl)-N-(5-methyl-1H-pyrazol-3-yl)-8-(trifluoromethyl)quinazolin-4-amine (30 mg, 20%). $^1$H NMR (300 MHz, DMSO-d$_6$) δ ppm 2.19 (s, 3H) 6.03 (s, 1H) 7.77 (t, J=7.91 Hz, 1H) 7.96-8.06 (m, 2H) 8.27 (d, J=7.53 Hz, 1H) 8.67 (s, 1H) 8.97 (d, J=8.29 Hz, 1H) 11.00 (br s, 1H) 12.18 (br s, 1 H); LC-MS (ESI) m/z 439 (M+H)$^+$.

Example 34

Preparation of 2-(difluoro(5-fluoropyridin-2-yl)methyl)-N-(5-methyl-1H-pyrazol-3-yl)-8-(trifluoromethoxy)quinazolin-4-amine

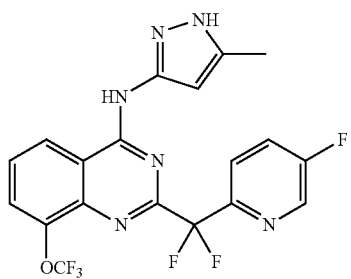 [SMILES: Cc1cc(Nc2nc(C(F)(F)c3ccc(F)cn3)nc3c(OC(F)(F)F)cccc23)n[nH]1]

Step A:

To 2,2-difluoro-2-(5-fluoropyridin-2-yl)acetic acid from Example 33 step A (863 mg, 4.52 mmol) and 2-amino-3-(trifluoromethoxy)benzoic acid (1 g, 4.52 mmol) in pyridine (15 mL) was added triphenyl phosphite (1.3 mL, 4.97 mmol) and the mixture was heated in a microwave synthesizer at 150° C. for 10 min. The mixture was cooled to rt and then ethyl 3-aminopropanoate hydrochloride (763 mg, 4.97 mmol) was added and the mixture heated in a microwave synthesizer at 190° C. for 4 min. The crude mixture was concentrated under reduced pressure. THF (30 mL) was added followed by sodium ethoxide (21% in EtOH, 5 mL) and the mixture stirred at 60° C. for 0.5 h. The cooled mixture was concentrated under reduced pressure, dissolved in water and the pH adjusted to <4 by addition of 4 N HCl. The precipitate was collected by filtration, washed with water, and allowed to dry to afford 2-(difluoro(5-fluoropyridin-2-yl)methyl)-8-(trifluoromethoxy)quinazolin-4-ol (1.31 g, 77%) as a crude tan solid which was used in the next step without further purification.

Step B:

To 2-(difluoro(5-fluoropyridin-2-yl)methyl)-8-(trifluoromethoxy)quinazolin-4-ol (250 mg, 0.66 mmol) was added phosphoryl tribromide (2.3 g) and toluene (2 mL) followed by DIEA (0.232 mL, 1.33 mmol). The mixture was heated at 105° C. for 0.5 h, then allowed to cool to rt. The mixture partitioned between EtOAc and saturated aq sodium bicarbonate and the organic layer was dried over sodium sulfate and concentrated under reduced pressure. To the residue was added a solution of 5-methyl-1H-pyrazol-3-amine (280 mg, 2.8 mmol) in DMF (5 mL) and the mixture was stirred at rt for 2 h. The crude mixture was purified by preparative HPLC (Varian diphenyl reverse phase column, eluting with a gradient of solvent B=0.05% HOAc/ACN and solvent A=0.05% HOAc/H$_2$O) to afford 2-(difluoro(5-fluoropyridin-2-yl)methyl)-N-(5-methyl-1H-pyrazol-3-yl)-8-(trifluoromethoxy)quinazolin-4-amine (100 mg, 33%). $^1$H NMR (300 MHz, DMSO-d$_6$) δ ppm 2.19 (s, 3H) 6.02 (s, 1H) 7.71 (t, J=8.10 Hz, 1H) 7.86-8.10 (m, 3H) 8.60-8.79 (m, 2H) 10.95 (s, 1H) 12.25 (br s, 1H); LC-MS (ESI) m/z 455 (M+H)$^+$.

Example 35

Preparation of 2-(difluoro(5-fluoropyridin-2-yl)methyl)-4-((5-methyl-1H-pyrazol-3-yl)amino)quinazoline-8-carbonitrile

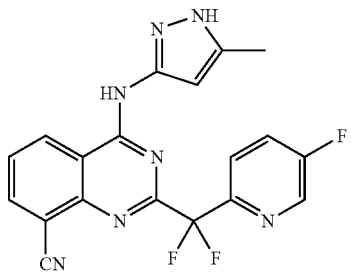

Step A:

To 2,2-difluoro-2-(5-fluoropyridin-2-yl)acetic acid from Example 33 step A (440 mg, 2.31 mmol) and 2-amino-3-bromobenzoic acid (0.5 g, 2.31 mmol) in pyridine (8 mL) was added triphenyl phosphite (0.667 mL, 2.54 mmol) and the mixture was heated in a microwave synthesizer at 150° C. for 10 min. The mixture was cooled to rt and then ethyl 3-aminopropanoate hydrochloride (396 mg, 2.54 mmol) was added and the mixture was heated in a microwave synthesizer at 180° C. for 3 min. The mixture was concentrated under reduced pressure. THF (10 mL) was added followed by sodium ethoxide (21% in EtOH, 3.2 mL) and the mixture was stirred at 50° C. for 2 h. An additional amount of sodium ethoxide (21% in EtOH, 1 mL) was added and the mixture stirred at 50° C. for 4 h. The mixture was allowed to cool and was partitioned between EtOAc and 1 N HCl. The organic layer was washed (3×) with 1 N HCl, dried over sodium sulfate, and concentrated under reduced pressure. The residue was triturated with DCM and collected by filtration to afford 8-bromo-2-(difluoro(5-fluoropyridin-2-yl)methyl)quinazolin-4-ol (444 mg, 52%). $^1$H NMR (300 MHz, DMSO-d$_6$) δ ppm 7.52 (t, J=7.91 Hz, 1H) 7.99-8.12 (m, 2H) 8.13-8.23 (m, 2H) 8.69 (d, J=2.45 Hz, 1H) 13.39 (br s, 1H).

Step B:

To 8-bromo-2-(difluoro(5-fluoropyridin-2-yl)methyl)quinazolin-4-ol (936 mg, 2.5 mmol) were added 2,4-bis(4-methoxyphenyl)-1,3,2,4-dithiadiphosphetane-2,4-dithione (1.53 g, 3.79 mmol) and pyridine (10 mL), and the mixture was heated in a microwave synthesizer at 170° C. for 20 min. The mixture was allowed to cool and concentrated under reduced pressure. The residue was partitioned between EtOAc and saturated aq sodium bicarbonate and the organic layer was separated and washed (3×) with saturated aq sodium bicarbonate (1×), 1 N HCl (1×), with brine. The organic layer was dried over sodium sulfate and concentrated under reduced pressure to afford 1.19 g of a solid To the solid were added 2-propanol (15 mL), NaOH (1 M, 4.62 mL, 4.62 mmol), and iodomethane (0.23 mL, 3.69 mmol). The mixture was stirred at rt for 10 min and then concentrated under reduced pressure. The residue was suspended in water, and the solid was collected by filtration washing with methanol to afford 8-bromo-2-(difluoro(5-fluoropyridin-2-yl)methyl)-4-(methylthio)quinazoline (901 mg, 89%). LC-MS (ESI) m/z 400/402 (M+H)$^+$.

Step C:

To a mixture of 8-bromo-2-(difluoro(5-fluoropyridin-2-yl)methyl)-4-(methylthio)quinazoline (300 mg, 0.75 mmol), tris(dibenzylideneacetone)dipalladium (69 mg, 0.075 mmol), 1,1'-bis(diphenylphosphino)ferrocene (49 mg, 0.088 mmol), and zinc cyanide (110 mg, 0.93 mmol) was added DMF (6 mL). The reaction flask was evacuated and flushed with argon (3×) and then the mixture was heated at 90° C. overnight. The resulting mixture was partitioned between EtOAc and water and the organic layer was washed with 2N NH$_4$OH (3×) and brine (1×), dried over sodium sulfate, and concentrated under reduced pressure onto Celite. The mixture was purified by silica gel flash chromatography eluting with 0-50% EtOAc/hexanes to afford 2-(difluoro(5-fluoropyridin-2-yl)methyl)-4-(methylthio)quinazoline-8-carbonitrile (168 mg, 64%). LC-MS (ESI) m/z 347 (M+H)$^+$.

Step D:

To 2-(difluoro(5-fluoropyridin-2-yl)methyl)-4-(methylthio)quinazoline-8-carbonitrile (168 mg, 0.48 mmol) in DCM (6 mL) at 0° C. was added 3-chloroperbenzoic acid (70%, 203 mg, 0.83 mmol) and the mixture stirred for 50 min. The mixture was diluted with DCM and then aq sodium thiosulfate solution was added followed by addition of saturated aq sodium bicarbonate. The organic layer was separate, dried over sodium sulfate and concentrated under reduced pressure. To the residue were added THF (3 mL) and 5-methyl-1H-pyrazol-3-amine (139 mg, 1.44 mmol) and the mixture was stirred at rt for 25 min. The mixture was concentrated under reduced pressure and purified by reverse phase HPLC (Varian C-18 reverse phase column, eluted with gradient of solvent B=0.05% formic acid/CH$_3$CN and solvent A=0.05% aq formic acid/5% CH$_3$CN) to afford 2-(difluoro(5-fluoropyridin-2-yl)methyl)-4-((5-methyl-1H-pyrazol-3-yl)amino)quinazoline-8-carbonitrile (78 mg, 41%). $^1$H NMR (300 MHz, DMSO-d$_6$) δ ppm 2.18 (s, 3H) 5.97 (s, 1H) 7.77 (t, J=7.91 Hz, 1H) 8.03 (dd, J=6.40, 1.32 Hz, 2 H) 8.45 (d, J=7.16 Hz, 1H) 8.68 (s, 1H) 8.99 (d, J=8.29 Hz, 1H) 11.04-11.20 (m, 1H) 12.18-12.37 (m, 1H); LC-MS (ESI) m/z 396 (M+H)$^+$.

Example 36

Preparation of 2-(difluoro(5-fluoropyridin-2-yl)methyl)-8-ethyl-N-(5-methyl-1H-pyrazol-3-yl)quinazolin-4-amine

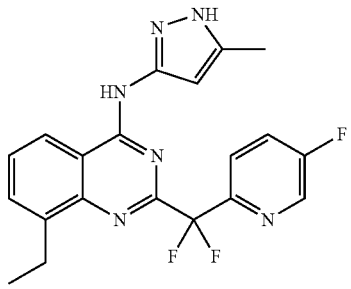 [SMILES: CCc1cccc2c(Nc3cc(C)[nH]n3)nc(C(F)(F)c3ccc(F)cn3)nc12]

Step A:

To a mixture of 8-bromo-2-(difluoro(5-fluoropyridin-2-yl)methyl)-4-(methylthio)quinazoline from Example 35 step B (300 mg, 0.75 mmol), bis(tri-tert-butylphosphine)palladium (38 mg, 0.075 mmol), tetraethyltin (0.295 mL, 1.5 mmol), and LiCl (95 mg, 2.25 mmol) was added DMF (15 mL). The reaction vessel was evacuated and flushed with argon (2×). The mixture was then heated in a microwave synthesizer at 135° C. for 30 min. The mixture was partitioned between EtOAc and saturated aq sodium bicarbonate and the organic layer was separated, washed with brine, dried over sodium sulfate, and concentrated under reduced pressure onto Celite. The mixture was purified by silica gel chromatography eluting with 0-10% EtOAc/hexanes to afford 2-(difluoro(5-fluoropyridin-2-yl)methyl)-8-ethyl-4-(methylthio)quinazoline (193 mg, 73%) as a white solid. LC-MS (ESI) m/z 350 (M+H)$^+$.

Step B:

To 2-(difluoro(5-fluoropyridin-2-yl)methyl)-8-ethyl-4-(methylthio)quinazoline (193 mg, 0.55 mmol) in DCM (5 mL) at 0° C. was added 3-chloroperbenzoic acid (70%, 218 mg, 0.89 mmol) and the mixture stirred for 40 min. The mixture was diluted with DCM and then aq sodium thiosulfate was added, followed by addition of saturated aq sodium bicarbonate solution. The organic layer was separated, dried over sodium sulfate, and concentrated under reduced pressure. To the residue were added THF (3 mL) and 5-methyl-1H-pyrazol-3-amine (163 mg, 1.67 mmol) and the mixture was stirred at rt for 4 days. The mixture was concentrated under reduced pressure and purified by preparative HPLC (Varian diphenyl reverse phase column, eluted with gradient of solvent B=0.05% AcOH/ACN and solvent A=5% ACN/0.05% AcOH/H$_2$O) to afford 2-(difluoro(5-fluoropyridin-2-yl)methyl)-8-ethyl-N-(5-methyl-1H-pyrazol-3-yl)quinazolin-4-amine (79 mg, 36%). $^1$H NMR (300 MHz, DMSO-d$_6$) δ ppm 1.21 (t, J=7.44 Hz, 3H) 2.19 (s, 3H) 3.05 (q, J=7.35 Hz, 2H) 6.03 (s, 1H) 7.55 (t, J=7.82 Hz, 1H) 7.74 (d, J=6.97 Hz, 1H) 7.95-8.06 (m, 2H) 8.51 (d, J=8.10 Hz, 1H) 8.67 (s, 1H) 10.58 (br s, 1H) 12.16 (br s, 1H); LC-MS (ESI) m/z 399 (M+H)$^+$.

Example 37

Preparation of 2-(difluoro(5-fluoropyridin-2-yl)methyl)-N-(5-methyl-1H-pyrazol-3-yl)-8-(methylsulfonyl)quinazolin-4-amine

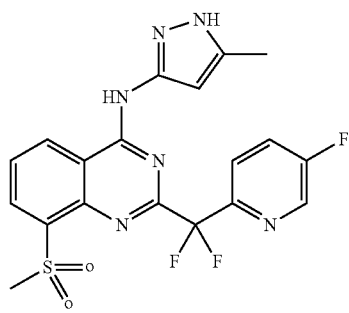

Step A:

To a mixture of 8-bromo-2-(difluoro(5-fluoropyridin-2-yl)methyl)-4-(methylthio)quinazoline from Example 35 step B (400 mg, 1 mmol), copper(I) trifluoromethanesulfonate benzene complex (503 mg, 1 mmol), sodium methanesulfinate (752 mg, 6.26 mmol) and N,N-dimethylethylenediamine (0.039 mL, 0.36 mmol) was added DMSO (15 mL). The reaction vessel was evacuated and flushed with argon (2×), and the mixture was heated in a microwave synthesizer at 120° C. for 10 min. The mixture was filtered and the filtrate was purified by preparative HPLC (Varian diphenyl reverse phase column, eluted with gradient of solvent B=0.05% AcOH/ACN and solvent A=5% ACN/0.05% AcOH/$H_2O$) to afford 2-(difluoro(5-fluoropyridin-2-yl)methyl)-8-(methylsulfonyl)quinazolin-4-ol (100 mg, 27%). $^1$H NMR (300 MHz, DMSO-$d_6$) δ ppm 3.22 (s, 3H) 7.81 (t, J=7.82 Hz, 1H) 8.00-8.11 (m, 2H) 8.38 (dd, J=7.54, 1.32 Hz, 1H) 8.45-8.51 (m, 1H) 8.71 (d, J=2.07 Hz, 1H) 13.64-13.78 (m, 1H).

Step B:

To 2-(difluoro(5-fluoropyridin-2-yl)methyl)-8-(methylsulfonyl)quinazolin-4-ol (100 mg, 0.27 mmol) were added phosphoryl tribromide (1.25 g) and toluene (0.5 mL) and DIEA (0.094 mL, 0.54 mmol), and the mixture was heated at 100° C. for 20 min. The mixture was cooled and partitioned between EtOAc and saturated aq sodium bicarbonate. The organic layer was dried over sodium sulfate and concentrated under reduced pressure. To the residue was added a solution of 5-methyl-1H-pyrazol-3-amine (67 mg, 0.69 mmol) in DMF (3 mL) and the mixture was stirred at rt for 0.5 h. The crude mixture was purified by preparative HPLC (Phenomenex C-18 reverse phase column, eluting with a gradient of solvent B=0.05% HOAc/ACN and solvent A=0.05% HOAc/$H_2O$) to afford 2-(difluoro(5-fluoropyridin-2-yl)methyl)-N-(5-methyl-1H-pyrazol-3-yl)-8-(methylsulfonyl)quinazolin-4-amine (72 mg, 69%). $^1$H NMR (300 MHz, DMSO-$d_6$) δ ppm 2.21 (s, 3H) 3.47 (s, 3H) 6.14 (s, 1H) 7.83 (t, J=7.91 Hz, 1H) 7.97-8.09 (m, 2H) 8.44 (d, J=7.35 Hz, 1H) 8.68 (s, 1H) 9.03 (d, J=8.10 Hz, 1H) 11.11 (s, 1H) 12.24-12.36 (m, 1H); LC-MS (ESI) m/z 449 (M+H)$^+$.

Example 38

Preparation of 2-(difluoro(5-fluoropyridin-2-yl)methyl)-N-(5-methyl-1H-pyrazol-3-yl)-7-(methylsulfonyl)quinazolin-4-amine

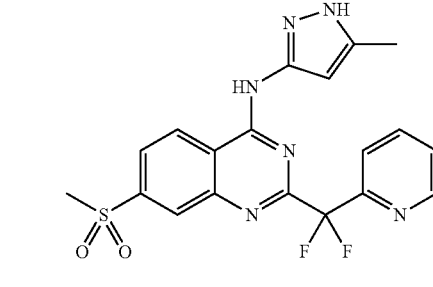

Step A:

To a mixture of 7-bromo-2-(difluoro(5-fluoropyridin-2-yl)methyl)-4-(methylthio)quinazoline from Example 7 step C (400 mg, 1 mmol), copper(I) trifluoromethanesulfonate benzene complex (503 mg, 1 mmol), sodium methanesulfinate (752 mg, 6.26 mmol) and N,N-dimethylethylenediamine (0.039 mL, 0.36 mmol) was added DMSO (15 mL). The reaction vessel was evacuated and flushed with argon (2×). The mixture was then heated in a microwave synthesizer at 130° C. for 10 min. The mixture was filtered and the filtrate was purified by preparative HPLC (Varian diphenyl reverse phase column, eluted with gradient of solvent B=0.05% AcOH/ACN and solvent A=5% ACN/0.05% AcOH/$H_2O$) to afford 2-(difluoro(5-fluoropyridin-2-yl)methyl)-7-(methylsulfonyl)quinazolin-4-ol (155 mg, 42%). $^1$H NMR (300 MHz, DMSO-$d_6$) δ ppm 7.98-8.13 (m, 3H) 8.19 (s, 1H) 8.40 (d, J=8.29 Hz, 1H) 8.68 (d, J=2.45 Hz, 1H) 13.50 (br s, 1H).

Step B:

To 2-(difluoro(5-fluoropyridin-2-yl)methyl)-7-(methylsulfonyl)quinazolin-4-ol (76 mg, 0.21 mmol) were added phosphoryl tribromide (1.21 g), toluene (0.5 mL), and DIEA (0.072 mL, 0.42 mmol), and the mixture was heated at 100° C. for 10 min. The mixture was cooled and partitioned between EtOAc and saturated aq sodium bicarbonate. The organic layer was dried over sodium sulfate and concentrated under reduced pressure. To the residue was added a solution of 5-methyl-1H-pyrazol-3-amine (59 mg, 0.6 mmol) in DMF (3 mL) and the mixture was stirred at rt for 20 min. The crude mixture was purified by preparative HPLC (Phenomenex C-18 reverse phase column, eluting with a gradient of solvent B=0.05% HOAc/ACN and solvent A=0.05% HOAc/$H_2O$) to afford 2-(difluoro(5-fluoropyridin-2-yl)methyl)-N-(5-methyl-1H-pyrazol-3-yl)-7-(methylsulfonyl)quinazolin-4-amine (40 mg, 45%). $^1$H NMR (300 MHz, DMSO-$d_6$) δ ppm 2.19 (s, 3H) 3.39 (s, 3H) 6.06 (s, 1H) 7.97-8.05 (m, 2H) 8.09 (d, J=7.72 Hz, 1H) 8.33 (s, 1H) 8.67 (s, 1H) 8.97 (d, J=8.48 Hz, 1H) 11.10 (br s, 1H) 12.28 (br s, 1H); LC-MS (ESI) m/z 449 (M+H)$^+$.

Example 39

Preparation of 2-(difluoro(5-fluoropyridin-2-yl)methyl)-4-((5-methyl-1H-pyrazol-3-yl)amino)quinazoline-8-carboxamide

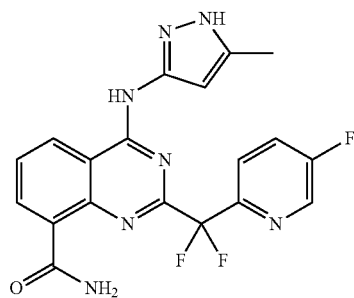 [SMILES: Cc1cc(Nc2nc(C(F)(F)c3ccc(F)cn3)nc3c(C(N)=O)cccc23)n[nH]1]

Step A:

To 2-(difluoro(5-fluoropyridin-2-yl)methyl)-4-(methylthio)quinazoline-8-carbonitrile from Example 35 step C (200 mg, 0.57 mmol) were added concentrated sulfuric acid (2.88 mL) and water (0.32 mL). The mixture was stirred at 65° C. for 1 h and then allowed to cool to rt. The mixture was neutralized by slow addition of saturated aq sodium bicarbonate and then extracted with EtOAc. The organic layer was washed with brine, dried over sodium sulfate, and concentrated under reduced pressure to afford 2-(difluoro(5-fluoropyridin-2-yl)methyl)-4-(methylthio)quinazoline-8-carboxamide (191 mg, 92%) as a yellow solid. $^1$H NMR (300 MHz, DMSO-$d_6$) δ ppm 2.60 (s, 3H) 7.89-8.15 (m, 4H) 8.36-8.44 (m, 1H) 8.62-8.69 (m, 1H) 8.71-8.79 (m, 1H) 9.28-9.39 (m, 1H).

Step B:

To 2-(difluoro(5-fluoropyridin-2-yl)methyl)-4-(methylthio)quinazoline-8-carboxamide (191 mg, 0.52 mmol) in DCM (8 mL) at 0° C. was added 3-chloroperbenzoic acid (70%, 192 mg, 0.78 mmol) and the mixture was stirred for 90 min. The mixture was diluted with DCM and then aq sodium thiosulfate was added, followed by addition of saturated aq sodium bicarbonate. The organic layer was dried over sodium sulfate and concentrated under reduced pressure. To the residue were added THF (5 mL) and 5-methyl-1H-pyrazol-3-amine (153 mg, 1.58 mmol) and the mixture was stirred at rt for 15 min. The mixture was concentrated under reduced pressure and purified by preparative HPLC (Varian diphenyl reverse phase column, eluted with gradient of solvent B=0.05% AcOH/ACN and solvent A=5% ACN/0.05% AcOH/H$_2$O) to afford 2-(difluoro(5-fluoropyridin-2-yl)methyl)-4-((5-methyl-1H-pyrazol-3-yl)amino)quinazoline-8-carboxamide (108 mg, 50%). $^1$H NMR (300 MHz, DMSO-$d_6$) δ ppm 2.20 (s, 3H) 6.08 (s, 1H) 7.76 (t, J=7.82 Hz, 1H) 7.92 (d, J=3.39 Hz, 1H) 7.98-8.11 (m, 2H) 8.58-8.75 (m, 2H) 8.89 (d, J=7.54 Hz, 1H) 9.91 (d, J=3.20 Hz, 1H) 10.80-11.38 (m, 1H) 12.17 (br s, 1H); LC-MS (ESI) m/z 414 (M+H)$^+$.

Example 40

Preparation of 8-chloro-2-(difluoro(5-fluoropyrimidin-2-yl)methyl)-N-(5-methyl-1H-pyrazol-3-yl)quinazolin-4-amine

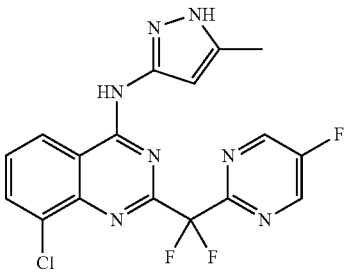 [SMILES: Cc1cc(Nc2nc(C(F)(F)c3ncc(F)cn3)nc3c(Cl)cccc23)n[nH]1]

Step A:

To sodium 2,2-difluoro-2-(5-fluoropyrimidin-2-yl)acetate from Example 3 step C (2.97 g, 13.87 mmol) was added EtOAc (100 mL) and 4 N HCl (100 mL) and the mixture shaken and partitioned. The organic phase was dried over sodium sulfate and concentrated under reduced pressure. Hexanes was added to the residue and the mixture again concentrated under reduced pressure to afford 2,2-difluoro-2-(5-fluoropyrimidin-2-yl)acetic acid (2.08 g, 78%), which was used without further purification.

Step B:

To 2,2-difluoro-2-(5-fluoropyrimidin-2-yl)acetic acid (700 mg, 3.64 mmol) and 2-amino-3-chlorobenzoic acid (625 mg, 3.64 mmol) in pyridine (10 mL) was added triphenyl phosphite (1.05 mL, 4 mmol) and the mixture heated in a microwave synthesizer at 150° C. for 10 min. The mixture was allowed to cool to rt and then ethyl 3-aminopropanoate hydrochloride (615 mg, 4 mmol) was added. The mixture was heated in a microwave synthesizer at 190° C. for 4 min, and then concentrated under reduced pressure. The residue was partitioned between EtOAc and 4 N HCl, and the organic layer was dried over sodium sulfate and concentrated under reduced pressure. To the residue was added THF (10 mL) followed by sodium ethoxide (21% in EtOH, 1 mL) and the mixture was stirred at 65° C. for 0.5 h. An additional amount of sodium ethoxide (21% in EtOH, 1 mL) was added and the mixture was stirred at 60° C. for 30 min. The mixture was allowed to cool to rt, and then partitioned between EtOAc and 4 N HCl. The organic phase was dried over sodium sulfate and concentrated under reduced pressure. The residue was triturated with hexanes and Et$_2$O, and the solid was collected by filtration to afford 8-chloro-2-(difluoro(5-fluoropyrimidin-2-yl)methyl)quinazolin-4-ol (420 mg, 35%) as a tan solid. LC-MS (ESI) m/z 327 (M+H)$^+$.

Step C:

To 8-chloro-2-(difluoro(5-fluoropyrimidin-2-yl)methyl)quinazolin-4-ol (200 mg, 0.61 mmol) were added phosphoryl tribromide (1.2 g) and toluene (2 mL) followed by DIEA (0.214 mL, 1.22 mmol). The mixture was heated at 105° C. for 45 min. The mixture was allowed to cool and was partitioned between EtOAc and saturated aq sodium bicarbonate. The organic layer was dried over sodium sulfate and concentrated under reduced pressure. To the crude residue was added a solution of 5-methyl-1H-pyrazol-3-amine (137 mg, 1.41 mmol) in DMF (4 mL) and the mixture was stirred at rt for 45 min. The crude mixture was purified by preparative HPLC (Varian diphenyl reverse phase column, eluting with a gradient of solvent B=0.05% HOAc/ACN and solvent A=0.05% HOAc/H$_2$O) to afford 8-chloro-2-(difluoro(5-fluoropyrimidin-2-yl)methyl)-N-(5-methyl-1H-pyrazol-3-yl)quinazolin-4-amine (75 mg, 30%). $^1$H NMR (300 MHz, DMSO-d$_6$) δ ppm 2.18 (s, 3H) 5.91 (s, 1H) 7.63 (t, J=8.01 Hz, 1H) 8.07 (d, J=7.54 Hz, 1H) 8.67 (d, J=8.29 Hz, 1H) 9.14 (s, 2H) 10.91 (br s, 1H) 12.24 (br s, 1H); LC-MS (ESI) m/z 406 (M+H)$^+$.

Example 41

Preparation of 2-(difluoro(5-fluoropyridin-2-yl)methyl)-4-((5-methyl-1H-pyrazol-3-yl)amino)quinazoline-7-carboxamide

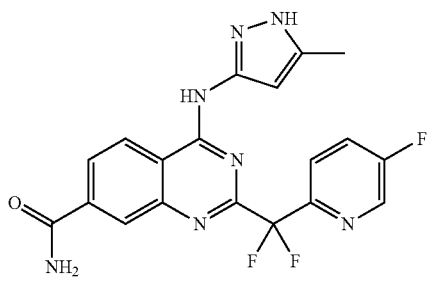 [SMILES: Cc1cc(Nc2nc(C(F)(F)c3ccc(F)cn3)nc3cc(C(N)=O)ccc23)n[nH]1]

Step A:

To 2-(difluoro(5-fluoropyridin-2-yl)methyl)-4-(methylthio)quinazoline-7-carbonitrile from Example 8 step A (174 mg, 0.5 mmol) were added concentrated sulfuric acid (2.88 mL) and water (0.32 mL). The mixture was stirred at 65° C. for 1 h and then allowed to cool to rt. The mixture was neutralized by slow addition of saturated aq sodium bicarbonate and then extracted with EtOAc. The organic layer was separated, washed with brine, dried over sodium sulfate, and concentrated under reduced pressure to afford 2-(difluoro(5-fluoropyridin-2-yl)methyl)-4-(methylthio)quinazoline-7-carboxamide (178 mg, 98%), which was used without further purification. LC-MS (ESI) m/z 365 (M+H)$^+$.

Step B:

To 2-(difluoro(5-fluoropyridin-2-yl)methyl)-4-(methylthio)quinazoline-7-carboxamide (203 mg, 0.55 mmol) in DCM (5 mL) at 0° C. was added 3-chloroperbenzoic acid (70%, 205 mg, 0.84 mmol) and the mixture was stirred for 90 min. An additional amount of 3-chloroperbenzoic acid (70%, 68 mg, 0.28 mmol) was then added and the mixture was stirred for 15 min. The mixture was diluted with DCM and then aq sodium thiosulfate was added, followed by saturated aq sodium bicarbonate. The organic layer was separated, dried over sodium sulfate, and concentrated under reduced pressure. To the residue were added THF (5 mL) and 5-methyl-1H-pyrazol-3-amine (160 mg, 1.65 mmol) and the mixture was stirred at rt for 20 min and then concentrated under reduced pressure. The residue was purified by preparative HPLC (Varian diphenyl reverse phase column, eluted with gradient of solvent B=0.05% AcOH/ACN and solvent A=5% ACN/0.05% AcOH/H$_2$O) to afford 2-(difluoro(5-fluoropyridin-2-yl)methyl)-4-((5-methyl-1H-pyrazol-3-yl)amino)quinazoline-7-carboxamide (21 mg, 10%). $^1$H NMR (300 MHz, DMSO-d$_6$) δ ppm 2.19 (s, 3H) 6.04 (s, 1H) 7.69 (s, 1H) 7.97-8.10 (m, 3H) 8.26-8.42 (m, 2H) 8.67 (s, 1H) 8.76 (d, J=8.67 Hz, 1H) 10.85 (br s, 1H) 12.20 (br s, 1H); LC-MS (ESI) m/z 414 (M+H)$^+$.

Example 42

Preparation of 4-(2-(difluoro(5-fluoropyridin-2-yl)methyl)-4-((5-methyl-1H-pyrazol-3-yl)amino)quinazolin-8-yl)morpholin-3-one

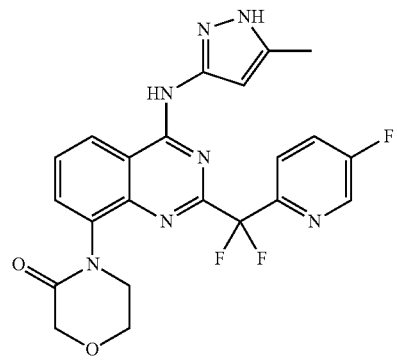 [SMILES: Cc1cc(Nc2nc(C(F)(F)c3ccc(F)cn3)nc3c(N4CCOCC4=O)cccc23)n[nH]1]

Step A:

To a mixture of 8-bromo-2-(difluoro(5-fluoropyridin-2-yl)methyl)-4-(methylthio)quinazoline from Example 35 step B (336 mg, 0.84 mmol), tris(dibenzylideneacetone)dipalladium (73 mg, 0.08 mmol), 4,5-bis(diphenylphosphino)-9,9-dimethylxanthene (144 mg, 0.25 mmol), morpholin-3-one (102 mg, 1 mmol) and Cs$_2$CO$_3$ (383 mg, 1.18 mmol) was added dioxane (5 mL). The reaction vessel was evacuated and flushed with argon (3×), and the mixture was heated at 100° C. overnight. The mixture was diluted with MeOH and DCM and concentrated under reduced pressure onto Celite. The mixture was purified by silica gel chromatography eluting with 0-100% EtOAc/hexanes to afford 4-(2-(difluoro(5-fluoropyridin-2-yl)methyl)-4-(methylthio)quinazolin-8-yl)morpholin-3-one (203 mg, 57%) as a mixture which was used without further purification. LC-MS (ESI) m/z 421 (M+H)$^+$.

Step B:

To 4-(2-(difluoro(5-fluoropyridin-2-yl)methyl)-4-(methylthio)quinazolin-8-yl)morpholin-3-one (180 mg, 0.428 mmol) in DCM (5 mL) at 0° C. was added 3-chloroperbenzoic acid (70%, 158 mg, 0.64 mmol) and the mixture was stirred for 30 min. The mixture was diluted with DCM and then aq sodium thiosulfate was added, followed by saturated aq sodium bicarbonate solution. The organic layer was separated, dried over sodium sulfate, and concentrated under reduced pressure. To the residue were added THF (3 mL) and 5-methyl-1H-pyrazol-3-amine (124 mg, 1.28 mmol) and the mixture was stirred at rt for 5 min. A precipitate formed which was collected by filtration and then purified by preparative HPLC (Varian C-18 reverse phase column, eluted with gradient of solvent B=0.05% formic acid/ACN and solvent A=5% ACN/0.05% formic acid/H$_2$O) to afford 4-(2-(difluoro(5-fluoropyridin-2-yl)methyl)-4-((5-methyl-1H-pyrazol-3-yl)amino)quinazolin-8-yl)morpholin-3-one (40 mg, 20%). $^1$H NMR (300 MHz, DMSO-d$_6$) δ ppm 2.21 (s, 3H) 3.65 (d, J=4.52 Hz, 2H) 3.85-3.93 (m, 2H) 4.18 (s, 2H) 6.20 (s, 1H) 7.63-7.71 (m, 1H) 7.82 (d, J=7.16 Hz, 1H) 7.93-8.05 (m, 2H) 8.57-8.73 (m, 2H) 10.84 (br s, 1H) 12.24 (br s, 1H); LC-MS (ESI) m/z 470 (M+H)$^+$.

Example 43

Preparation of 2-(difluoro(5-fluoropyridin-2-yl)methyl)-8-methoxy-N-(5-methyl-1H-pyrazol-3-yl)quinazolin-4-amine

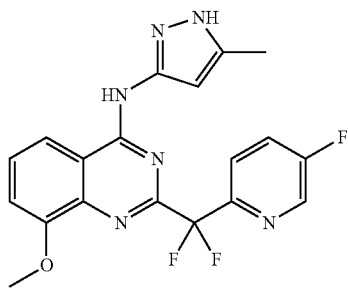 [SMILES: COc1cccc2c(Nc3cc(C)[nH]n3)nc(C(F)(F)c3ccc(F)cn3)nc12]

Step A:

To 2,2-difluoro-2-(5-fluoropyridin-2-yl)acetic acid from Example 33 step A (1 g, 5.23 mmol) and 2-amino-3-methoxybenzoic acid (875 mg, 5.23 mmol) in pyridine (15 mL) was added triphenyl phosphite (1.51 mL, 5.75 mmol) and the mixture was heated in a microwave synthesizer at 150° C. for 10 min. The mixture was allowed to cool to rt and then ethyl 3-aminopropanoate hydrochloride (883 mg, 5.75 mmol) was added. The mixture was heated in a microwave synthesizer at 190° C. for 4 min and then concentrated under reduced pressure. THF (10 mL) and sodium ethoxide (21% in EtOH, 4 mL) were added, and the mixture was stirred at 60° C. for 0.5 h. The mixture was allowed to cool and concentrated under reduced pressure. The residue was dissolved in water and the pH was adjusted to <4 by addition of 4 N HCl. The precipitate was collected by filtration, washed with water, and dried on the funnel to afford 2-(difluoro(5-fluoropyridin-2-yl)methyl)-8-methoxyquinazolin-4-ol (1.19 g, 71%). LC-MS (ESI) m/z 322 (M+H)$^+$.

Step B:

To 2-(difluoro(5-fluoropyridin-2-yl)methyl)-8-methoxyquinazolin-4-ol (450 mg, 1.4 mmol) were added phosphoryl tribromide (3.14 g) and toluene (4 mL) followed by DIEA (0.488 mL, 2.8 mmol). The mixture was heated at 105° C. for 1 h. The mixture was allowed to cool and was partitioned between EtOAc and saturated aq sodium bicarbonate. The organic layer was dried over sodium sulfate and concentrated under reduced pressure. To the residue was added a solution of 5-methyl-1H-pyrazol-3-amine (300 mg, 3.1 mmol) in DMF (4 mL) and the mixture was stirred at rt for 3 days. The crude mixture was purified by preparative HPLC (Varian C-18 reverse phase column, eluting with a gradient of solvent B=0.05% formic acid/ACN and solvent A=0.05% formic acid/H$_2$O/5% ACN) to afford 2-(difluoro(5-fluoropyridin-2-yl)methyl)-8-methoxy-N-(5-methyl-1H-pyrazol-3-yl)quinazolin-4-amine (170 mg, 30%). $^1$H NMR (300 MHz, DMSO-d$_6$) δ ppm 2.16 (s, 3H) 3.95 (s, 3H) 5.91 (s, 1H) 7.38 (d, J=7.91 Hz, 1H) 7.56 (t, J=8.10 Hz, 1H) 7.93-8.06 (m, 2H) 8.19 (d, J=8.10 Hz, 1H) 8.66 (s, 1H) 10.53 (br s, 1H) 12.15 (br s, 1H); LC-MS (ESI) m/z 401 (M+H)$^+$.

Example 44

Preparation of N-(2-(difluoro(5-fluoropyridin-2-yl)methyl)-4-((5-methyl-1H-pyrazol-3-yl)amino)quinazolin-8-yl)formamide

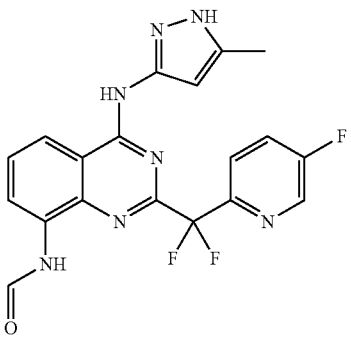 [SMILES: Cc1cc(Nc2nc(C(F)(F)c3ccc(F)cn3)nc3c(NC=O)cccc23)n[nH]1]

Step A:

To a mixture of 8-bromo-2-(difluoro(5-fluoropyridin-2-yl)methyl)-4-(methylthio)quinazoline from Example 35 step B (250 mg, 0.63 mmol), tris(dibenzylideneacetone)dipalladium (58 mg, 0.063 mmol), 4,5-bis(diphenylphosphino)-9,9-dimethylxanthene (109 mg, 0.19 mmol), formamide (0.075 mL, 1.875 mmol) and Cs$_2$CO$_3$ (284 mg, 0.875 mmol) was added dioxane (4 mL). The reaction vessel was evacuated and flushed with argon (3×) and the mixture was heated at 90° C. overnight. The mixture was diluted with DCM and concentrated under reduced pressure onto Celite. The residue was purified by silica gel chromatography eluting with 0-50% EtOAc/hexanes to afford N-(2-(difluoro(5-fluoropyridin-2-yl)methyl)-4-(methylthio)quinazolin-8-yl)formamide (168 mg, 74%).

$^1$H NMR (300 MHz, CHLOROFORM-d) δ ppm 2.55 (s, 3H) 7.54-7.68 (m, 2H) 7.77 (d, J=7.72 Hz, 1H) 7.99 (dd, J=8.67, 4.33 Hz, 1H) 8.46 (d, J=2.45 Hz, 1H) 8.68 (d, J=1.13 Hz, 1H) 8.93 (d, J=7.72 Hz, 1H) 9.50 (br s, 1H).

Step B:

To N-(2-(difluoro(5-fluoropyridin-2-yl)methyl)-4-(methylthio)quinazolin-8-yl)formamide (168 mg, 0.462 mmol) in DCM (5 mL) at 0° C. was added 3-chloroperbenzoic acid (70%, 171 mg, 0.69 mmol) and the mixture stirred for 40 min. The mixture was diluted with DCM and then aq sodium thiosulfate and saturated aq sodium bicarbonate were added. The organic layer was separated, dried over sodium sulfate, and concentrated under reduced pressure. To the residue were added THF (4 mL) and 5-methyl-1H-pyrazol-3-amine (135 mg, 1.38 mmol) and the mixture was stirred at rt for 20 min. The mixture was concentrated under reduced pressure and purified by preparative HPLC (Varian C-18 reverse phase column, eluted with gradient of solvent B=0.05% formic acid/ACN and solvent A=5% ACN/0.05% formic acid/H$_2$O) to afford N-(2-(difluoro(5-fluoropyridin-2-yl)methyl)-4-((5-methyl-1H-pyrazol-3-yl)amino)quinazolin-8-yl)formamide (66 mg, 35%). $^1$H NMR (300 MHz, DMSO-d$_6$) δ ppm 2.17 (s, 3H) 5.89 (s, 1H) 7.61 (t, J=8.10 Hz, 1H) 7.96-8.11 (m, 2H) 8.37 (d, J=8.29 Hz, 1H) 8.66 (d, J=11.87 Hz, 2H) 8.79 (d, J=7.72 Hz, 1H) 10.24 (s, 1H) 10.77 (br s, 1H) 11.81-12.73 (m, 1H); LC-MS (ESI) m/z 414 (M+H)$^+$.

Example 45

Preparation of 2-(difluoro(5-fluoropyridin-2-yl)methyl)-4-((5-methyl-1H-pyrazol-3-yl)amino)-N-(oxetan-3-yl)quinazoline-8-carboxamide

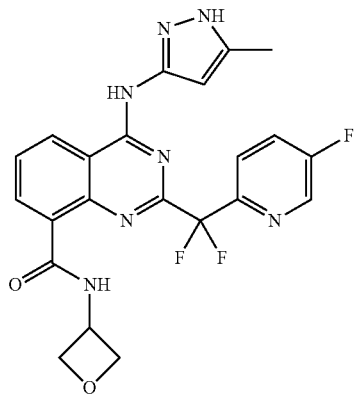 [SMILES: Cc1cc(Nc2nc(C(F)(F)c3ccc(F)cn3)nc3c(C(=O)NC4COC4)cccc23)n[nH]1]

Step A:

To a mixture of 8-bromo-2-(difluoro(5-fluoropyridin-2-yl)methyl)-4-(methylthio)quinazoline from Example 35 step B (200 mg, 0.5 mmol), palladium acetate (6 mg, 0.025 mmol), 4,5-bis(diphenylphosphino)-9,9-dimethylxanthene (29 mg, 0.05 mmol), oxetan-3-amine (55 mg, 0.75 mmol) and $K_3PO_4$ (320 mg, 1.5 mmol) was added toluene (2 mL). The vial was evacuated and flushed with carbon monoxide (2×) and the mixture was heated at 110° C. overnight under an atmosphere of carbon monoxide. The mixture was diluted with DCM/MeOH and concentrated under reduced pressure onto Celite. The residue was purified by silica gel chromatography eluting with 10-100% EtOAc/hexanes to afford 2-(difluoro(5-fluoropyridin-2-yl)methyl)-4-(methylthio)-N-(oxetan-3-yl)quinazoline-8-carboxamide (56 mg, 26%). LC-MS (ESI) m/z 421 (M+H)$^+$.

Step B:

To 2-(difluoro(5-fluoropyridin-2-yl)methyl)-4-(methylthio)-N-(oxetan-3-yl)quinazoline-8-carboxamide (56 mg, 0.13 mmol) in DCM (5 mL) at 0° C. was added 3-chloroperbenzoic acid (70%, 42 mg, 0.17 mmol) and the mixture was stirred for 60 min. The mixture was diluted with DCM and then aq sodium thiosulfate and saturated aq sodium bicarbonate solution were added. The organic layer was separated, dried over sodium sulfate, and concentrated under reduced pressure. To the residue were added THF (3 mL) and 5-methyl-1H-pyrazol-3-amine (96 mg, 1 mmol), and the mixture was stirred at rt for 45 min. The mixture was concentrated under reduced pressure and then purified by preparative HPLC (Varian C-18 reverse phase column, eluted with gradient of solvent B=0.05% formic acid/ACN and solvent A=5% ACN/0.05% formic acid/$H_2O$) to afford N-(2-(difluoro(5-fluoropyridin-2-yl)methyl)-4-((5-methyl-1H-pyrazol-3-yl)amino)quinazolin-8-yl)formamide (20 mg, 33%). $^1$H NMR (300 MHz, DMSO-$d_6$) δ ppm 2.20 (s, 3H) 4.47 (t, J=6.31 Hz, 2H) 4.89 (t, J=6.88 Hz, 2H) 5.09 (sxt, J=6.67 Hz, 1H) 6.07 (s, 1H) 7.77 (t, J=7.82 Hz, 1H) 7.99-8.13 (m, 2H) 8.61 (d, J=6.97 Hz, 1H) 8.71 (d, J=2.26 Hz, 1H) 8.90 (d, J=8.10 Hz, 1H) 11.10 (br s, 1H) 11.45 (d, J=6.40 Hz, 1H) 12.28 (br s, 1H); LC-MS (ESI) m/z 470 (M+H)$^+$.

Example 46

Preparation of 2-(difluoro(5-fluoropyridin-2-yl)methyl)-4-((5-methyl-1H-pyrazol-3-yl)amino)quinazolin-8-ol

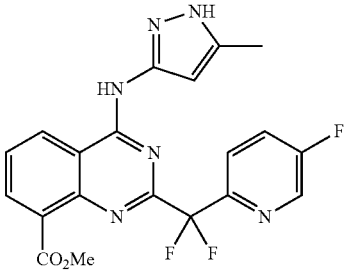 [SMILES: COC(=O)c1cccc2c(Nc3cc(C)[nH]n3)nc(C(F)(F)c3ccc(F)cn3)nc12]

Step A:

To 2-(difluoro(5-fluoropyridin-2-yl)methyl)-8-methoxy-N-(5-methyl-1H-pyrazol-3-yl)quinazolin-4-amine from Example 43 step B (150 mg, 0.375 mmol) in DCM (10 mL) at −78° C. under argon was added boron tribromide (1M in DCM, 3.75 mL, 3.75 mmol). The mixture was stirred at −78° C. for 20 min, and then allowed to warm slowly to rt. Additional boron tribromide (1M in DCM, 4 mL, 4 mmol) was added and the mixture was stirred at rt for 6 days. MeOH was added slowly and then the mixture was concentrated under reduced pressure to afford a mixture of brominated products. The mixture was partially purified by preparative HPLC (Varian C-18 reverse phase column, eluted with gradient of solvent B=0.05% formic acid/ACN and solvent A=5% ACN/0.05% formic acid/$H_2O$). To the recovered product were added a 1:1 mixture of THF/MeOH (8 mL) and palladium hydroxide (20% on carbon, 50 mg) and the mixture was heated under an atmosphere of hydrogen at 50° C. for 1 h. The mixture was filtered, and the filtrate was concentrated under reduced pressure, and then purified by preparative HPLC (Varian C-18 reverse phase column, eluted with gradient of solvent B=0.05% formic acid/ACN and solvent A=5% ACN/0.05% formic acid/$H_2O$) to afford 2-(difluoro(5-fluoropyridin-2-yl)methyl)-4-((5-methyl-1H-pyrazol-3-yl)amino)quinazolin-8-ol (3 mg, 2%). $^1$H NMR (300 MHz, DMSO-$d_6$) δ ppm 2.16 (s, 3H) 5.91 (s, 1H) 7.25 (d, J=7.54 Hz, 1H) 7.45 (t, J=8.10 Hz, 1H) 7.89-8.19 (m, 3H) 8.66 (s, 1H) 9.80 (br s, 1H) 10.52 (br s, 1H) 12.16 (br s, 1H). LC-MS (ESI) m/z 387 (M+H)$^+$.

Example 47

Preparation of methyl 2-(difluoro(5-fluoropyridin-2-yl)methyl)-4-((5-methyl-1H-pyrazol-3-yl)amino)quinazoline-8-carboxylate Step A:

2-Amino-3-(trifluoromethyl)benzamide (15 g, 73.47 mmol) and 2,2-difluoro-2-(5-fluoropyridin-2-yl)acetic acid (12.6 g, 66.1 mmol) were suspended in polyphosphoric acid (100 mL) and the mixture was heated at 115° C. with mechanical stirring for 24 h, and then cooled to room temperature. The reaction mixtures from this batch and several similar batches (total 245 mmol) were combined and quenched with cold water (4 L). The resulting suspension was triturated with DCM (2 L) and the solid product was collected by filtration to afford 3-carbamoyl-2-(2,2-difluoro-2-(5-fluoropyridin-2-yl)acetamido)benzoic acid (25 g, 32%). LC-MS (ESI) m/z 354 (M+H$^+$). The aqueous layer was separated from the two phase filtrate and extracted with DCM (2×0.5 L). The DCM extracts were combined and saved. The aqueous layer was extracted several times with EtOAc (total 2 L). The EtOAc extracts were combined, washed with water (3×500 mL), and concentrated. The residue was dissolved in DCM (50 mL) and extracted with 10% NaHCO$_3$. The aqueous layer was acidified to pH 1, and the precipitate was collected by filtration to afford additional 3-carbamoyl-2-(2,2-difluoro-2-(5-fluoropyridin-2-yl)acetamido)benzoic acid (3.5 g, 5%). The saved DCM fraction from above was concentrated to 20% of the original volume. The solid precipitate was collected by filtration and washed with cold DCM to afford 2-(difluoro(5-fluoropyridin-2-yl)methyl)-4-hydroxyquinazoline-8-carboxylic acid (3.5 g, 5%). LC-MS (ESI) m/z 336 (M+H$^+$). The filtrate was extracted with 10% NaHCO$_3$, and the aqueous layer was adjusted to pH 8-9, filtered, and acidified to pH 1. The resulting precipitate was collected by filtration to afford additional 2-(difluoro(5-fluoropyridin-2-yl)methyl)-4-hydroxyquinazoline-8-carboxylic acid (7.0 g, 10%). From the organic phase could be recovered intermediate 2-(difluoro(5-fluoropyridin-2-yl)methyl)-8-(trifluoromethyl)quinazolin-4(3H)-one (~3.5 g), which was resubjected to heating in polyphosphoric acid followed by quenching with water to afford additional 2-(difluoro(5-fluoropyridin-2-yl)methyl)-4-hydroxyquinazoline-8-carboxylic acid as a solid (3.0 g).

Step B:

2-(2,2-difluoro-2-(5-fluoropyridin-2-yl)acetamido)-3-carbamoylbenzoic acid (28.5 g, 81 mmol) in MeOH (1000 mL) was treated with 2M HCl/ether (4 mL) and then heated at reflux overnight. The mixture was concentrated to 10% of the original volume and the resulting precipitate was collected by filtration and washed with a small amount of MeOH to afford methyl 2-(difluoro(5-fluoropyridin-2-yl)methyl)-4-oxo-3,4-dihydroquinazoline-8-carboxylate (17.5 g, 62%). Separately, 2-(difluoro(5-fluoropyridin-2-yl)methyl)-4-hydroxyquinazoline-8-carboxylic acid (10.5 g, 31 mmol) in MeOH (200 mL) was treated with 2M HCl/ether (1 mL) and was heated at reflux overnight. The mixture was concentrated to 10% of the original volume and the resulting precipitate was collected by filtration and washed with a small amount of MeOH to afford methyl 2-(difluoro(5-fluoropyridin-2-yl)methyl)-4-oxo-3,4-dihydroquinazoline-8-carboxylate (5.5 g, 51%). The filtrates from the two procedures above were concentrated at 65° C. and allowed to cool. The solid was collected by filtration to afford additional methyl 2-(difluoro(5-fluoropyridin-2-yl)methyl)-4-oxo-3,4-dihydroquinazoline-8-carboxylate (3 g). Purification of the filtrate by silica gel chromatography eluting with EtOAc/hexanes afforded additional methyl 2-(difluoro(5-fluoropyridin-2-yl)methyl)-4-oxo-3,4-dihydroquinazoline-8-carboxylate (4 g). The isolated solids were combined to afford methyl 2-(difluoro(5-fluoropyridin-2-yl)methyl)-4-oxo-3,4-dihydroquinazoline-8-carboxylate as a solid (30 g). LC-MS (ESI) m/z 350 (M+H$^+$).

Step C:

A mixture of methyl 2-(difluoro(5-fluoropyridin-2-yl)methyl)-4-oxo-3,4-dihydroquinazoline-8-carboxylate (30 g, 85.9 mmol), POBr$_3$ (3.7 g, 429.5 mmol), TEA (43.5 g, 429.5 mmol) and DMF (0.1 mL) in toluene (300 mL) was heated with stirring at 100° C. for 4 h. The mixture was concentrated and the residue was suspended in water (1 L) and extracted with EtOAc (3×200 mL). The combined organic layers were washed with water (2×50 mL) and brine, and then concentrated at 35° C. under reduced pressure until a solid began to precipitate. The mixture was allowed to cool, and the solid was collected by filtration and washed with a small quantity of cold EtOAc to afford methyl 4-bromo-2-(difluoro(5-fluoropyridin-2-yl)methyl)quinazoline-8-carboxylate (23 g, 65%). LC-MS (ESI) m/z 412.7, 414.7 (M+H$^+$). The filtrate was concentrated and the residue was purified by silica gel chromatography eluting with EtOAc/hexanes to afford additional methyl 4-bromo-2-(difluoro(5-fluoropyridin-2-yl)methyl)quinazoline-8-carboxylate (3.0 g, 8%).

Step D:

To a solution of methyl 4-bromo-2-(difluoro(5-fluoropyridin-2-yl)methyl)quinazoline-8-carboxylate (27 g, 65.5 mmol) in dioxane (300 mL) was added 5-methyl-1H-pyrazol-3-amine (12.7 g, 131 mmol) and the mixture was stirred at 50° C. overnight. The mixture was concentrated and the residue was triturated with water (1 L). The solid was collected by filtration, washed with water, and dried in air to afford methyl 2-(difluoro(5-fluoropyridin-2-yl)methyl)-4-((5-methyl-1H-pyrazol-3-yl)amino)quinazoline-8-carboxylate as a solid. (26.7 g, 95%). LC-MS (ESI) m/z 429.6 (M+H$^+$). $^1$H NMR (500 MHz, DMSO-d$_6$) δ 12.23 (1H, s), 10.86 (1H, s), 8.82 (1H, d, J=8.2 Hz), 8.67 (1H, d, J=2.6 Hz), 7.99 (3H, m), 7.68 (1H, t, J=8.0 Hz), 6.05 (1H, s), 3.83 (3H, s), 2.19 (3H, s).

Example 48

Preparation of N-(2-(difluoro(5-fluoropyridin-2-yl)methyl)-4-((5-methyl-1H-pyrazol-3-yl)amino)quinazolin-8-yl)acetamide

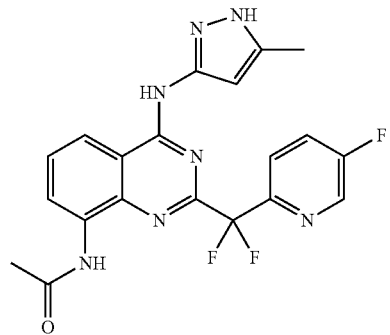 [SMILES: CC(=O)Nc1cccc2c(Nc3cc(C)[nH]n3)nc(C(F)(F)c3ccc(F)cn3)nc12]

Step A:

To a mixture of 8-bromo-2-(difluoro(5-fluoropyridin-2-yl)methyl)-4-(methylthio)quinazoline from Example 35 step B (200 mg, 0.5 mmol), tris(dibenzylideneacetone)dipalladium (46 mg, 0.05 mmol), 4,5-bis(diphenylphosphino)-9,9-dimethylxanthene (87 mg, 0.15 mmol), acetamide (89 mg, 1.5 mmol) and Cs$_2$CO$_3$ (230 mg, 0.7 mmol) was added dioxane (4 mL). The reaction vessel was evacuated and flushed with argon (3×), and the mixture was heated at 90° C. overnight. The mixture was diluted with DCM and concentrated under reduced pressure onto Celite. The residue was purified by silica gel chromatography eluting with 0-50% EtOAc/hexanes to afford N-(2-(difluoro(5-fluoropyridin-2-yl)methyl)-4-(methylthio)quinazolin-8-yl)acetamide (90 mg, 48%). LC-MS (ESI) m/z 379 (M+H)⁺.

Step B:

To N-(2-(difluoro(5-fluoropyridin-2-yl)methyl)-4-(methylthio)quinazolin-8-yl)acetamide (90 mg, 0.24 mmol) in DCM (5 mL) at 0° C. was added 3-chloroperbenzoic acid (70%, 77 mg, 0.3 mmol) and the mixture stirred for 40 min. The mixture was diluted with DCM and then aq sodium thiosulfate and saturated aq sodium bicarbonate were added. The organic layer was separated, dried over sodium sulfate, and concentrated under reduced pressure. To the residue were added THF (3 mL) and 5-methyl-1H-pyrazol-3-amine (107 mg, 1.1 mmol) and the mixture was stirred at rt for 1 h. The mixture was concentrated under reduced pressure and purified by preparative HPLC (Varian diphenyl reverse phase column, eluting with a gradient of solvent B=0.05% HOAc/ACN and solvent A=0.05% HOAc/H₂O) to afford N-(2-(difluoro(5-fluoropyridin-2-yl)methyl)-4-((5-methyl-1H-pyrazol-3-yl)amino)quinazolin-8-yl)acetamide (37 mg, 36%). ¹H NMR (300 MHz, DMSO-d₆) δ ppm 2.17 (s, 3H) 2.24 (s, 3H) 5.93 (s, 1H) 7.59 (t, J=8.10 Hz, 1H) 7.92-8.12 (m, 2H) 8.34 (d, J=8.29 Hz, 1H) 8.57-8.75 (m, 2H) 9.52 (s, 1H) 10.76 (br s, 1H) 12.20 (br s, 1H); LC-MS (ESI) m/z 428 (M+H)⁺.

Example 49

Preparation of 2-(difluoro(5-fluoropyridin-2-yl)methyl)-N-(5-methyl-1H-pyrazol-3-yl)-8-nitroquinazolin-4-amine

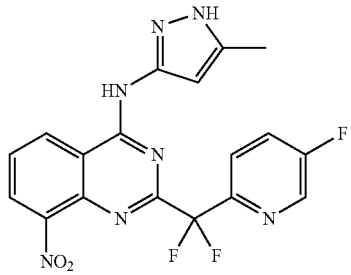

Step A:

To a mixture of 2,2-difluoro-2-(5-fluoropyridin-2-yl)acetic acid from Example 33 step A (1.05 g, 5.49 mmol) and 2-amino-3-nitrobenzoic acid (1 g, 5.49 mmol) in pyridine (15 mL) was added triphenyl phosphite (1.59 mL, 6.03 mmol), and the mixture heated in a microwave synthesizer at 150° C. for 10 min. The mixture was allowed to cool to rt, and then ethyl 3-aminopropanoate hydrochloride (945 mg, 6.03 mmol) was added. The mixture was heated in a microwave synthesizer at 190° C. for 4 min, and then concentrated under reduced pressure. THF (20 mL) and sodium ethoxide (21% in EtOH, 10 mL) were added and the mixture was heated at 50° C. for 0.5 h with stirring. The mixture was concentrated under reduced pressure and then partitioned between EtOAc and 4 N HCl. The organic layer was dried over sodium sulfate, concentrated under reduced pressure, and then purified by silica gel chromatography eluting with 10-100% EtOAc/hexanes. The residue was triturated with Et₂O and the solid was collected by filtration to afford 2-(difluoro(5-fluoropyridin-2-yl)methyl)-8-nitroquinazolin-4-ol (566 mg, 31%). ¹H NMR (300 MHz, DMSO-d₆) δ ppm 7.77 (t, J=7.91 Hz, 1H) 7.97-8.11 (m, 2H) 8.30-8.48 (m, 2H) 8.68 (s, 1H) 13.61 (br s, 1H).

Step B:

To 2-(difluoro(5-fluoropyridin-2-yl)methyl)-8-nitroquinazolin-4-ol (312 mg, 0.92 mmol) were added phosphoryl tribromide (1.66 g), toluene (3 mL), and DIEA (0.325 mL, 1.85 mmol), and the mixture was heated at 90° C. for 0.75 h. The mixture was allowed to cool and was partitioned between EtOAc and a saturated aq sodium bicarbonate. The organic layer was dried over sodium sulfate and concentrated. To the residue was added a solution of 5-methyl-1H-pyrazol-3-amine (220 mg, 2.3 mmol) in DMF (4 mL) and the mixture was stirred at rt for 0.5 h. Water was added and the resulting precipitate was collected by filtration and dried on the funnel to give a crude solid (406 mg, quantitative). An analytical sample was prepared by purification with preparative HPLC (Varian diphenyl reverse phase column, eluting with a gradient of solvent B=0.05% HOAc/ACN and solvent A=0.05% HOAc/H₂O) to afford 2-(difluoro(5-fluoropyridin-2-yl)methyl)-N-(5-methyl-1H-pyrazol-3-yl)-8-nitroquinazolin-4-amine. ¹H NMR (300 MHz, DMSO-d₆) δ ppm 2.18 (s, 3H) 5.95 (s, 1H) 7.78 (t, J=8.01 Hz, 1H) 7.95-8.07 (m, 2H) 8.38 (d, J=7.54 Hz, 1H) 8.67 (s, 1H) 8.94 (d, J=8.10 Hz, 1H) 11.18 (br s, 1H) 12.25 (br s, 1H); LC-MS (ESI) m/z 416 (M+H)⁺.

Example 50

Preparation of 2-(difluoro(5-fluoropyridin-2-yl)methyl)-N4-(5-methyl-1H-pyrazol-3-yl)quinazoline-4,8-diamine

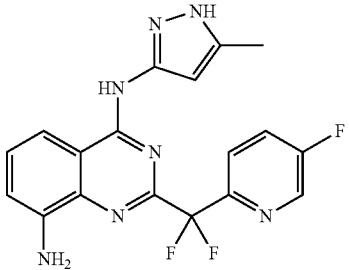 [SMILES: Cc1cc(Nc2nc(C(F)(F)c3ccc(F)cn3)nc3c([N+](=O)[O-])cccc23)n[nH]1]

To crude 2-(difluoro(5-fluoropyridin-2-yl)methyl)-N-(5-methyl-1H-pyrazol-3-yl)-8-nitroquinazolin-4-amine from Example 49 step B (210 mg, 0.5 mmol) in EtOH (10 mL) was added palladium hydroxide (20% on carbon, 70 mg) and the mixture was stirred under an atmosphere of hydrogen for 1 h at rt, then 0.5 h at 75° C. The mixture was filtered washing with MeOH, and then the filtrate was concentrated under reduced pressure to afford a residue (140 mg). A portion (70 mg) of the residue was purified by preparative HPLC (Varian diphenyl reverse phase column, eluting with a gradient of solvent B=0.05% HOAc/ACN and solvent A=0.05% HOAc/H₂O) to afford 2-(difluoro(5-fluoropyridin-2-yl)methyl)-N4-(5-methyl-1H-pyrazol-3-yl)quinazoline-4,8-diamine (17 mg, 9%). ¹H NMR (300 MHz, DMSO-d₆) δ ppm 2.16 (s, 3H) 5.81 (s, 2H) 5.94 (s, 1H) 7.00 (d, J=7.72 Hz, 1H) 7.31 (t, J=8.01 Hz, 1H) 7.72 (d, J=8.29 Hz, 1H) 7.92-8.09 (m, 2H) 8.66 (s, 1H) 10.33 (br s, 1H) 12.09 (br s, 1H); LC-MS (ESI) m/z 386 (M+H)⁺.

Example 51

Preparation of 8-cyclopropyl-2-(difluoro(5-fluoropyridin-2-yl)methyl)-N-(5-methyl-1H-pyrazol-3-yl)quinazolin-4-amine

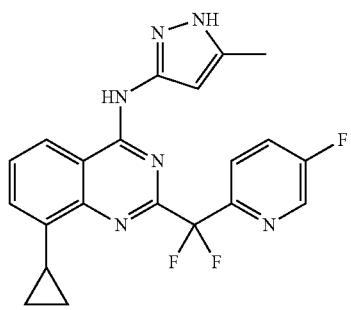 [SMILES: Cc1cc(Nc2nc(C(F)(F)c3ccc(F)cn3)nc3c(C4CC4)cccc23)n[nH]1]

Step A:

To a mixture of 8-bromo-2-(difluoro(5-fluoropyridin-2-yl)methyl)-4-(methylthio)quinazoline from Example 35 step B (200 mg, 0.5 mmol), dichlorobis(tricyclohexylphosphine) palladium(II) (37 mg, 0.05 mmol), cyclopropylboronic acid (65 mg, 0.75 mmol) and $K_3PO_4$ (371 mg, 1.75 mmol) were added toluene (6 mL) and water (0.5 mL). The reaction vessel was evacuated and flushed with argon (3×), and then the mixture was heated at 100° C. for 4 h. The mixture was concentrated under reduced pressure onto Celite and the residue was purified by silica gel chromatography eluting with 10-50% EtOAc/hexanes to afford impure 8-cyclopropyl-2-(difluoro(5-fluoropyridin-2-yl)methyl)-4-(methylthio)quinazoline (150 mg, 84%) which was used without further purification.

Step B:

To 8-cyclopropyl-2-(difluoro(5-fluoropyridin-2-yl)methyl)-4-(methylthio)quinazoline (150 mg, 0.41 mmol) in DCM (5 mL) cooled to 0° C. was added 3-chloroperbenzoic acid (70%, 42 mg, 0.17 mmol) and the mixture stirred for 15 min. The mixture was diluted with DCM and then a sodium thiosulfate solution, followed by a saturated sodium bicarbonate solution was added. The organic layer was dried over sodium sulfate and concentrated under reduced pressure. To the obtained residue was added THF (4 mL) and 5-methyl-1H-pyrazol-3-amine (185 mg, 1.9 mmol) and the mixture stirred at rt for 30 min. The crude mixture was concentrated under reduced pressure and then purified by preparative HPLC (Varian C-18 reverse phase column, eluted with gradient of solvent B=0.05% formic acid/ACN and solvent A=5% ACN/0.05% formic acid/$H_2O$) to afford 8-cyclopropyl-2-(difluoro(5-fluoropyridin-2-yl)methyl)quinazolin-4-ol (50 mg, 37%). LC-MS (ESI) m/z 332 (M+H)$^+$.

Step C:

To 8-cyclopropyl-2-(difluoro(5-fluoropyridin-2-yl)methyl)quinazolin-4-ol (50 mg, 0.15 mmol) were added phosphoryl tribromide (0.86 g) and toluene (2 mL) followed by DIEA (0.053 mL, 0.3 mmol). The mixture was heated at 95° C. for 0.5 h. The mixture was cooled and partitioned between EtOAc and a saturated aq sodium bicarbonate. The organic layer was dried over sodium sulfate and concentrated. To the residue was added a solution of 5-methyl-1H-pyrazol-3-amine (100 mg, 1 mmol) in DMF (3 mL) and the mixture was stirred at rt overnight. The mixture was purified by preparative HPLC (Varian diphenyl reverse phase column, eluting with a gradient of solvent B=0.05% HOAc/ACN and solvent A=0.05% HOAc/$H_2O$) to afford 8-cyclopropyl-2-(difluoro(5-fluoropyridin-2-yl)methyl)-N-(5-methyl-1H-pyrazol-3-yl)quinazolin-4-amine (30 mg, 48%). $^1$H NMR (300 MHz, DMSO-$d_6$) δ ppm 0.79-0.90 (m, 2H) 1.04-1.16 (m, 2H) 2.17 (s, 3H) 2.95-3.10 (m, 1H) 5.97 (s, 1H) 7.32 (d, J=7.35 Hz, 1H) 7.52 (t, J=7.91 Hz, 1H) 7.96-8.06 (m, 2H) 8.43 (d, J=8.10 Hz, 1H) 8.67 (s, 1H) 10.57 (br s, 1H) 12.15 (br s, 1H); LC-MS (ESI) m/z 411 (M+H)$^+$.

Example 52

Preparation of N-(2-(difluoro(5-fluoropyridin-2-yl)methyl)-4-((5-methyl-1H-pyrazol-3-yl)amino)quinazolin-8-yl)methanesulfonamide

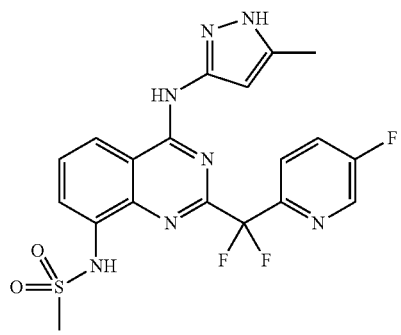 [SMILES: Cc1cc(Nc2nc(C(F)(F)c3ccc(F)cn3)nc3c(NS(C)(=O)=O)cccc23)n[nH]1]

Step A:

To a mixture of 8-bromo-2-(difluoro(5-fluoropyridin-2-yl)methyl)-4-(methylthio)quinazoline from Example 35 step B (250 mg, 0.625 mmol), tris(dibenzylideneacetone)dipalladium (57 mg, 0.063 mmol), 4,5-Bis(diphenylphosphino)-9,9-dimethylxanthene (108 mg, 0.187 mmol), methanesulfonamide (83 mg, 0.87 mmol) and $Cs_2CO_3$ (284 mg, 0.87 mmol) was added dioxane (5 mL). The reaction vessel was evacuated and flushed with argon (3×), and the mixture was heated at 100° C. overnight. The mixture was allowed to cool and was then diluted with DCM and concentrated under reduced pressure onto Celite. The residue was purified by silica gel flash chromatography eluting with 10-100% EtOAc/hexanes to afford impure N-(2-(difluoro(5-fluoropyridin-2-yl)methyl)-4-(methylthio)quinazolin-8-yl)methanesulfonamide (220 mg, 85%). LC-MS (ESI) m/z 415 (M+H)$^+$.

Step B:

To N-(2-(difluoro(5-fluoropyridin-2-yl)methyl)-4-(methylthio)quinazolin-8-yl)methanesulfonamide (220 mg, 0.53 mmol) in DCM (5 mL) at 0° C. was added 3-chloroperbenzoic acid (70%, 160 mg, 0.64 mmol) and the mixture was stirred for 1 h. The mixture was diluted with DCM and then aq sodium thiosulfate and saturated aq sodium bicarbonate were added. The organic layer separated, dried over sodium sulfate, and concentrated under reduced pressure. To the residue were added THF (5 mL) and 5-methyl-1H-pyrazol-3-amine (excess) and the mixture was stirred at rt overnight. The mixture was concentrated under reduced pressure and purified by preparative HPLC (Varian C-18 reverse phase column, eluted with gradient of solvent B=0.05% formic acid/ACN and solvent A=5% ACN/0.05% formic acid/$H_2O$) to afford N-(2-(difluoro(5-fluoropyridin-2-yl)methyl)-4-((5-methyl-1H-pyrazol-3-yl)amino)quinazolin-8-yl)methanesulfonamide (3 mg, 1%). $^1$H NMR (300 MHz, DMSO-$d_6$) δ ppm 2.17 (s, 3H) 3.18 (s, 3H) 5.96 (s, 1H) 7.57-7.67 (m, 1H) 7.79 (d, J=7.72 Hz, 1H) 7.98-8.08 (m, 2H) 8.43 (d, J=8.29 Hz, 1H) 8.67 (s, 1H) 9.08 (br s, 1H) 10.81 (br s, 1H) 12.23 (br s, 1H); LC-MS (ESI) m/z 464 (M+H)+.

Example 53

Preparation of 2-(difluoro(5-fluoropyridin-2-yl)methyl)-4-((5-methyl-1H-pyrazol-3-yl)amino)quinazoline-8-carboxylic acid

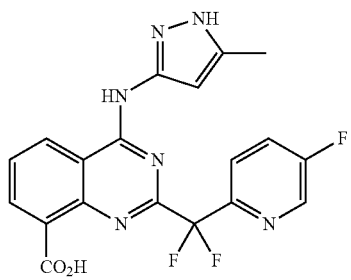

A solution of methyl 2-(difluoro(5-fluoropyridin-2-yl)methyl)-4-((5-methyl-1H-pyrazol-3-yl)amino)quinazoline-8-carboxylate (26.7 g, 62.3 mmol) in 1:1 3N NaOH/dioxane (200 mL) was stirred at rt for 2 h. The mixture was concentrated under reduced pressure, and the resulting aqueous solution was acidified with 3N HCl. The resulting precipitate was collected by filtration, washed with water, and dried in air to afford 2-(difluoro(5-fluoropyridin-2-yl)methyl)-4-((5-methyl-1H-pyrazol-3-yl)amino)quinazoline-8-carboxylic acid as a solid (24.1 g, 93%). LC-MS (ESI) m/z 415.6 (M+H). $^1$H NMR (500 MHz, DMSO-$d_6$) δ 15.61 (1H, br s), 12.39 (1H, br s), 11.41 (1H, br s), 9.00 (1H, d, J=8.2 Hz), 8.71 (1H, s), 8.59 (1H, d, J=7.36 Hz), 8.09-8.03 (2H, m), 7.83 (1H, t, J=7.86 Hz), 6.07 (1H, s), 2.20 (3H, s).

Example 54

Competition Binding Assay to Determine Binding Constants ($K_d$) of the Compounds Against JAK Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at rt to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17×PBS, 0.05% Tween 20, 6 mM DTT). Test compounds were prepared as 100× stocks in DMSO and rapidly diluted into the aqueous environment. DMSO was added to control assays lacking a test compound. Primary screen interactions were performed in polypropylene 384-well plates in a final volume of 34 μL, while $K_d$ determinations were performed in polystyrene 96-well plates in a final volume of 135 μL. The assay plates were incubated at room temperature with shaking for 1 hour, long enough for binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 2 μM non-biotinylated affinity ligand) and incubated at room temperature with shaking for 30 min. The kinase concentration in the eluates was measured by quantitative PCR. Each kinase was tested individually against each compound. Kds were determined using eleven serial threefold dilutions. A selectivity score, which is a quantitative measure of selectivity of a compound against a panel of enzymes, may be calculated for a compound by dividing the number of enzymes for which a compound meets a set criteria, (for example, a binding constant of 100 nM or less), by the total number of enzymes tested. A kinase selectivity score, S10, for example, is calculated for each compound by dividing the number of kinases for which a compound at a certain concentration (for example, 10 μM) displayed inhibition of 90% or greater compared to negative control lacking inhibitors (DMSO only), divided by the number of distinct kinases tested excluding mutant variants, typically 359 or 386 kinases.

In one embodiment, the compounds provided herein were found to have Kds of less than about 20 μM against JAK2. In another embodiment, the compounds provided herein were found to have Kds of less than about 10 μM against JAK2. In another embodiment, the compounds provided herein were found to have Kds of less than about 1 μM against JAK2.

In another embodiment, the compounds provided herein were found to have Kds of less than about 20 μM against JAK3. In another embodiment, the compounds provided herein were found to have Kds of less than about 10 μM against JAK3. In another embodiment, the compounds provided herein were found to have Kds of less than about 1 μM against JAK3.

Example 55 csTF-1 Cell-Based Reporter Assay csTF-1 cells are derived from the human erythroleukemia cell line that is growth dependent on GM-CSF and has an intact GM-CSFR/JAK2/STAT5 pathway. The cell line contains stably integrated beta-lactamase reporter gene under the control of the regulatory factor 1 (irf 1) response element recognized by the activated transcription factor STATS. csTF-1 cells (Invitrogen K1219) were washed with assay media (97% OPTIMEM/0.5% dialyzed FBS/0.1 mM NEAA/1 mM Na pyr/P/S) and seeded in the same media at 5×10$^5$ cell/mL in T150 flask. After 16 hour incubation, cells were seeded at 2×10$^5$ cell/well in 50 μl volume, into Costar, clear bottom, 96-well assay plates. Serial dilutions of compounds were added to the plates with final DMSO concentration at 0.5% and GM-CSF at 2 ng/mL and the plates were then incubated at 30° C. and 5% $CO_2$ for 4 hours. The plates were brought to room temperature before adding Substrate Mixture according to manufacturer's protocol (Invitrogen, Catalog #K1085). The assay plates containing the substrate mixture were incubated in the dark at room temperature for 2 hours. Blue and green fluorescence was measured with excitation at 409 nm and emission at 460 nm (for blue) and excitation at 409 nm and emission at 530 nm (for green) using Spectra Max Gemini EM. The compounds provided herein were found to have IC$_{50}$ of less than about 5 μM. In another embodiment, the compounds provided herein were found to have activity IC$_{50}$ of less than about 500 nM.

The compounds provided herein were found to have the following activity shown in Table 1:

TABLE 1

| Compound | Cell Assay: CS TF-1 reporter assay IC50 (nM) | Binding Assay: JAK2 Kd (nM) | Binding Assay: JAK3 Kd (nM) | Binding Assay: Tyk2 Kd (nM) | S-Score: S(10) at 10 μM |
|---|---|---|---|---|---|
| Example 1 | A | B | B | A | A |
| Example 2 | A | A | A | A | C |
| Example 3 | A | A | B | A | D |
| Example 4 | A | A | A | A | A |
| Example 5 | B | A | B | A | C |
| Example 6 | A | A | A | A | C |
| Example 7 | A | A | A | A | B |
| Example 8 | A | B | B | A | A |
| Example 9 | A | A | A | A | C |
| Example 10 | A | A | A | A | C |
| Example 11 | B | A | B | A | A |
| Example 12 | A | A | A | A | C |
| Example 13 | A | A | A | A | B |
| Example 14 | A | A | A | A | D |
| Example 15 | A | A | B | A | C |
| Example 16 | A | A | B | A | B |
| Example 30 | B | B | C | B | A |
| Example 31 | C | C | C | B | A |
| Example 33 | B | B | C | B | A |
| Example 34 | B | B | B | A | A |
| Example 35 | B | A | B | A | A |
| Example 36 | B | A | B | A | A |
| Example 37 | B | B | B | A | A |
| Example 38 | B | A | A | A | D |
| Example 39 | A | A | A | A | C |
| Example 40 | A | A | B | A | B |
| Example 41 | C | A | A | A | D |
| Example 42 | B | A | A | A | B |
| Example 43 | A | A | A | A | C |
| Example 44 | A | A | A | A | D |
| Example 45 | A | A | A | A | B |
| Example 46 | C | A | A | A | D |
| Example 47 | ND | A | A | A | ND |
| Example 48 | A | A | A | A | C |
| Example 49 | B | B | B | B | A |
| Example 50 | A | A | A | A | D |
| Example 51 | B | A | B | A | A |
| Example 52 | A | A | A | A | ND |
| Example 53 | B | A | A | A | A |

In Table 1,
CSTF-1 reporter assay IC$_{50}$ (nM): A ≤ 100, 100 < B ≤ 500, C > 500;
JAK2 Kd (nM): A ≤ 1, 1 < B ≤ 10, C > 10;
JAK3 Kd (nM): A ≤ 10, 10 < B ≤ 100, C > 100;
Tyk2 Kd (nM): A ≤ 10, 10 < B ≤ 100, C > 100;
S score: A ≤ 0.3, 0.3 < B ≤ 0.4, 0.4 < C ≤ 0.5, D > 0.5;
and ND = no data.

In certain embodiments, the compounds provided herein bind to JAK2 kinase with higher specificity as compared to non-mutant and non-JAK family kinases. For certain compounds provided herein, binding constants for less than 10 non-mutant and non-JAK family kinases are within 100-fold of the binding constant for JAK2 kinase for compounds provided herein. For certain compounds provided herein, binding constants for less than 8 non-mutant and non-JAK family kinases are within 100-fold of the binding constant for JAK2 kinase for compounds provided herein. For certain compounds provided herein, binding constants for 6 non-mutant and non-JAK family kinases are within 100-fold of the binding constant for JAK2 kinase.

Example 56

Adenosine A$_3$ Receptor Antagonist Cell-Based Assay

Adenosine A$_3$ receptor, also known as A$_3$AR or ADORA$_3$, is a G protein-coupled receptor (GPCR). One of the compounds of Formula I provided herein was assayed in an antagonist mode using cell lines specifically expressing human ADORA$_3$ in an assay utilizing enzyme fragment complementation with β-galactosidase (β-Gal) as the functional reporter (PathHunter β-Arrestin assay, DiscoveRx Corporation).

For this assay, a human ADORA$_3$-expressing PathHunter cell line was grown according to standard procedures and maintained in selective growth media prior to assay. Cells were seeded in 384-well microplates at a density of 5000 cells per well in a total volume of 20 μL and were allowed to adhere and recover overnight prior to compound addition. 2-Cl-IB-MECA agonist dose curves were performed the morning of profiling to determine the EC80 value that was used for the following antagonist compound testing. For antagonist determination, cells were preincubated with one of the compound of Formula I (5 μL of 5× compound added to cells for 30 minutes at 37° C.) followed by 2-Cl-IB-MECA agonist challenge at the EC80 concentration (5 μL of 6× EC80 agonist incubated at 37° C. for 90 minutes). Assay signal was generated by addition of 15 μL of PathHunter Detection reagent cocktail for 1 hour at room temperature. Microplates were read with a Perkin Elmer Envision instrument for chemiluminescent signal detection. Percentage inhibition was calculated using the following formula: % Inhibition=100%×(1−(Mean RLU of test sample−mean RLU of vehicle control)/(mean RLU of EC80 control−mean RLU of vehicle control)). One of the compounds of Formula I provided herein was found in this assay to have an IC$_{50}$ of 29.6 nM.

Since modifications will be apparent to those of skill in the art, it is intended that the claimed subject matter be limited only by the scope of the appended claims.

What is claimed is:

1. A compound having formula (I):

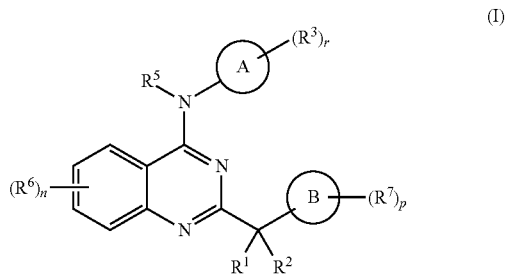

or a pharmaceutically acceptable salt thereof, wherein
A is azolyl;
B is 6-membered nitrogen containing heteroaryl;
R$^1$ and R$^2$ are selected from (i), (ii), (iii), (iv) and (v) as follows:
(i) R$^1$ and R$^2$ together form =O, =S, =NR$^9$ or =CR$^{10}$R$^{11}$;
(ii) R$^1$ and R$^2$ are both —OR$^8$, or R$^1$ and R$^2$, together with the carbon atom to which they are attached, form cycloalkyl or heterocyclyl wherein the cycloalkyl is substituted with one to four substitutents selected from halo, deutero, alkyl, cycloalkyl, heterocyclyl, aryl, heteroaryl, cyano, =O, =N—OR$^{21}$, —R$^x$OR$^{21}$, —R$^x$N(R$^{22}$)$_2$, —R$^x$S(O)$_q$R$^{23}$, —C(O)R$^{21}$, —C(O)OR$^{21}$ and —C(O)N(R$^{22}$)$_2$ and wherein the heterocyclyl contains one to two heteroatoms wherein each heteroatom is independently selected from O, NR$^{24}$, S, S(O) and S(O)$_2$;
(iii) R$^1$ is hydrogen or halo; and R$^2$ is halo; and
(iv) R$^1$ is alkyl, alkenyl, alkynyl, cycloalkyl or aryl, wherein the alkyl, alkenyl, alkynyl, cycloalkyl and aryl are each optionally substituted with one to four substitutents selected from halo, cyano, alkyl, —R$^x$-OR$^w$, —R$^x$S(O)$_q$R$^v$, —R$^x$NR$^y$R$^z$ and —C(O)OR$^w$; and R$^2$ is hydrogen, halo or —OR$^8$; and (v) R$^1$ is halo, deutero, —OR$^{12}$, —NR$^{13}$R$^{14}$, or —S(O)$_q$R$^{15}$; and R$^2$ is hydrogen, deutero, alkyl, alkenyl, alkynyl, cycloalkyl or aryl, wherein the alkyl, alkenyl, cycloalkyl and aryl are each optionally substituted with one to four substituents selected from halo, cyano, alkyl, —R$^x$OR$^w$, —R$^x$S(O)$_q$R$^v$ and —R$^x$-NR$^y$R$^z$;

each R$^3$ is independently hydrogen, deutero, halo, alkyl, cyano, haloalkyl, deuteroakyl, cycloalkyl, cycloalkylalkyl, hydroxy or alkoxy;

R$^5$ is hydrogen or alkyl;

each R$^6$ is independently selected from deutero, halo, nitro, cyano, alkyl, alkenyl, alkynyl, haloalkyl, cycloalkyl, aryl, arylalkyl, heteroaryl, heteroarylalkyl, heterocyclyl, heterocyclylalkyl, —R$^x$OR$^{18}$, —R$^x$NR$^{19}$R$^{20}$, —R$^x$C(O)NR$^y$R$^z$, —R$^x$S(O)$_q$R$^v$, —R$^x$NR$^{19}$C(O)R$^{18}$, —R$^x$C(O)OR$^{18}$ and —R$^x$NR$^{19}$S(O)$_q$R$^v$; where the alkyl, alkenyl, alkynyl, haloalkyl, cycloalkyl, aryl, heteroaryl and heterocyclyl groups are optionally substituted with one, two or three halo, oxo, hydroxy, alkoxy, alkyl, alkenyl, alkynyl, haloalkyl, or cycloalkyl groups;

each R$^7$ is independently halo, alkyl, haloalkyl. or —R$^x$-OR$^w$;

R$^8$ is alkyl, alkenyl or alkynyl;

R$^9$ is hydrogen, alkyl, haloalkyl, hydroxy, alkoxy or amino;

R$^{10}$ is hydrogen or alkyl;

R$^{11}$ is hydrogen, alkyl, haloalkyl or —C(O)OR$^8$;

R$^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)OR$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one to four substituents independently selected from halo, oxo, alkyl, hydroxy, alkoxy, amino and alkylthio;

R$^{13}$ and R$^{14}$ are selected as follows:

(i) R$^{13}$ is hydrogen or alkyl; and R$^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one to four substituents independently selected from halo, oxo, alkyl, hydroxy, alkoxy, amino and alkylthio; or (ii) R$^{13}$ and R$^{14}$, together with the nitrogen atom to which they are attached, form heterocyclyl or heteroaryl wherein the heterocyclyl or heteroaryl are substituted with one to four substituents independently selected from halo, alkyl, hydroxy, alkoxy, amino and alkylthio and wherein the heterocyclyl is optionally substituted with oxo;

R$^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkenyl, alkynyl, cycloalkyl, cycloalkylalkyl, heterocyclyl, heterocyclylalkyl, aryl, aralkyl, heteroaryl and heteroaralkyl are each optionally substituted with one to four substituents independently selected from halo, oxo, alkyl, hydroxy, alkoxy, amino and alkylthio;

R$^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein R$^{18}$ is optionally substituted with 1 to 3 groups Q$^1$, each Q$^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

R$^{19}$ and R$^{20}$ are selected as follows:

(i) R$^{19}$ and R$^{20}$ are each independently hydrogen or alkyl; or (ii) R$^{19}$ and R$^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

R$^{21}$ is hydrogen, alkyl, alkenyl, alkynyl, haloalkyl or cycloalkyl;

each R$^{22}$ is independently hydrogen, alkyl, alkenyl, alkynyl, haloalkyl or cycloalkyl; or both R$^{22}$, together with the nitrogen atom to which they are attached, form a heterocyclyl optionally substituted with oxo;

R$^{23}$ is alkyl, alkenyl, alkynyl or haloalkyl;

R$^{24}$ is hydrogen or alkyl;

each R$^x$ is independently alkylene or a direct bond;

R$^v$ is hydrogen, alkyl, alkenyl or alkynyl;

R$^w$ is independently hydrogen, alkyl, alkenyl, alkynyl or haloalkyl;

R$^y$ and R$^z$ are selected as follows:

(i) R$^y$ and R$^z$ are each independently hydrogen, alkyl, alkenyl, alkynyl, cycloalkyh haloalkyl or heterocyclyl;

(ii) R$^y$ and R$^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;

r is 1-3;

p is 0-4; and each q is independently 0, 1 or 2.

2. The compound of claim 1, wherein and R$^2$ together form =O.

3. The compound of claim 1, wherein R$^1$ and R$^2$ are both fluoro.

4. The compound of claim 1, wherein R$^3$ is hydrogen, alkyl or alkoxy.

5. The compound of claim 1, wherein each R$^6$ is independently deutero, cyano, halo, alkyl, alkoxy, haloalkoxy, cycloalkyl, alkylsulfonyl, alkylsulfonylamino, aminocarbonyl, heterocyclylaminocarbonyl, oxo-substituted heterocyclyl, carboxyl, formylamino or acetylamino.

6. The compound of claim 1, wherein n is 0 or 1.

7. The compound of claim 1, wherein p is 1.

8. The compound of claim 1, wherein A is pyrazolyl, imidazolyl, oxazolyl, thiazolyl, thiadiazolyl, or triazotyl.

9. The compound of claim 1, wherein A is

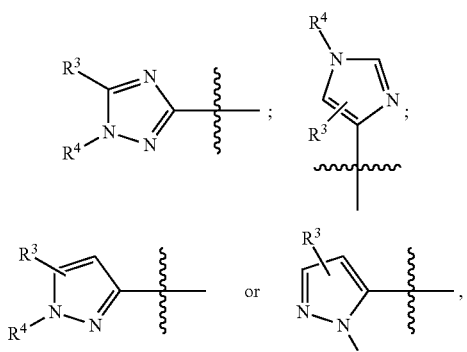

wherein each $R^3$ is independently hydrogen, halo, alkyl, hydroxy or alkoxy; and each $R^4$ is independently hydrogen, or alkyl.

10. The compound of claim 1, wherein $R^7$ is halo.

11. The compound of claim 1 having formula (III)

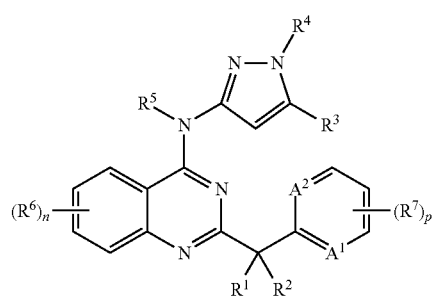

(III)

or a pharmaceutically acceptable salt thereof wherein $A^1$ and $A^2$ are selected from N and CH, such that at least one of $A^1$ or $A^2$ is N.

12. The compound of claim 1 having formula (VIIIa), (VIIIb) or (VIIIc)

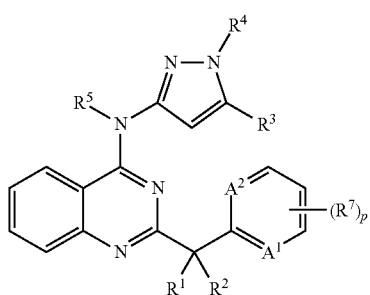

(VIIIa)

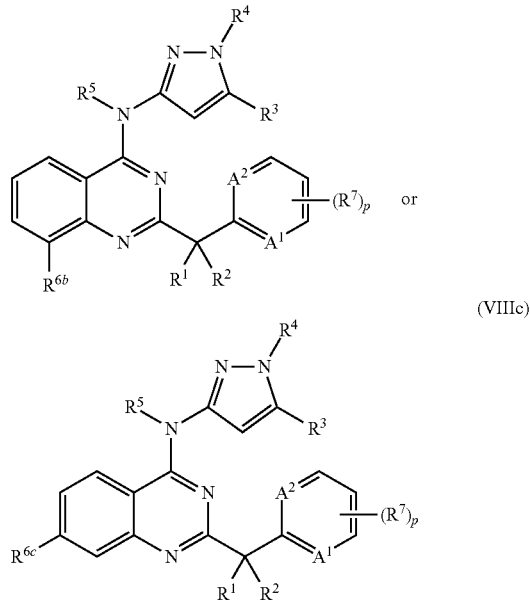

or a pharmaceutically acceptable salt thereof, wherein:
  $A^1$ and $A^2$ are selected from N and CH, such that at least one of $A^1$ or $A^2$ is N;
  $R^1$ and $R^2$ are selected as follows:
    (i) $R^1$ and $R^2$ together form =O; or
    (ii) $R^1$ is hydrogen or halo, and $R^2$ is halo;
  $R^3$ is hydrogen, alkyl or cycloalkyl,
  $R^4$ and $R^5$ are each independently hydrogen or alkyl;
  $R^{6c}$ is selected from deutero, halo, cyano, alkyl, haloalkyl, haloalkoxy and alkoxy;
  $R^{6d}$ is selected from deutero, halo, cyano, alkyl, haloalkyl, haloalkoxy, alkoxy, alkylsulfonylamino, aminocarbonyl, heterocyclylaminocarbonyl, oxo-substituted heterocylyl, carboxyl, formaylamino and acetylamino;
  each $R^7$ independently halo, alkyl or haloalkyl; and
  p is 1 or 2.

13. The compound of claim 12, wherein $A^1$ and $A^2$ are selected from N and CH, such that at least one of $A^1$ or $A^2$ is N;
  $R^1$ and $R^2$ together form =O; or $R^1$ and $R^2$ are both halo;
  $R^3$ is hydrogen, alkyl or cycloalkyl;
  $R^4$ and $R^5$ are each independently hydrogen or alkyl;
  $R^{6c}$ is selected from deutero, halo, cyano, alkyl, haloalkyl, haloalkoxy and alkoxy;
  $R^{6d}$ is selected from deutero, halo, cyano, alkyl, haloalkyl, haloalkoxy, alkoxy, alkylsulfonylamino, aminocarbonyl, heterocyclylaminocarbonyl, oxo-substituted heterocylyl, carboxyl, formylamino and acetylamino;
  each $R^7$ is independently halo, alkyl or haloalkyl; and
  p is 1.

14. The compound of claim 13, wherein $A^1$ and $A^2$ are selected from N and CH, such that at least one of A' or $A^2$ is N;
  $R^1$ and $R^2$ together form =O; or $R^1$ and $R^2$ are both fluoro;
  $R^3$ is hydrogen, alkyl or cycloalkyl,
  $R^4$ and $R^5$ are each independently hydrogen or alkyl;
  $R^{6c}$ is selected from halo, cyano, alkyl and alkoxy;
  $R^{6d}$ is selected from halo and alkyl;
  $R^7$ is fluoro; and
  p is 1.

15. The compound of claim 1 having formula (XIa), (XIb) or (XIc)

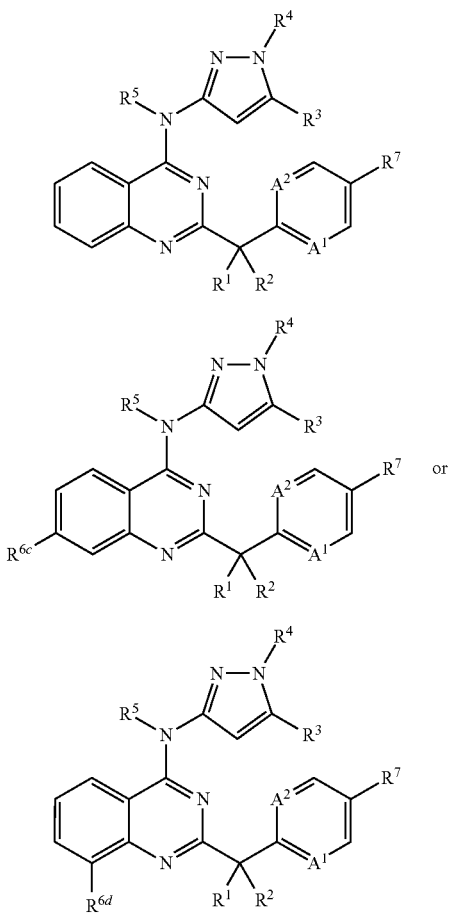

(XIa)

(XIb)

(XIc)

or a pharmaceutically acceptable salt thereof, wherein $A^1$ and $A^2$ are selected from N and CH, such that at least one of $A^1$ or $A^2$ is N;

$R^3$ is hydrogen or alkyl;

$R^{6c}$ is selected from deutero, halo, cyano, alkyl, haloalkyl, haloalkoxy and alkoxy; and $R^{6d}$ is selected from deutero, halo, cyano, alkyl, haloalkyl, haloalkoxy, alkoxy, alkylsulfonyl, alkylsulfonylamino, aminocarbonyl, heterocyclylaminocarbonyl, oxo-substituted heterocylyl, carboxyl, formylamino and acetylamino.

16. The compound of claim 1 having formula (XIIa), (XIIb) or (XIIc)

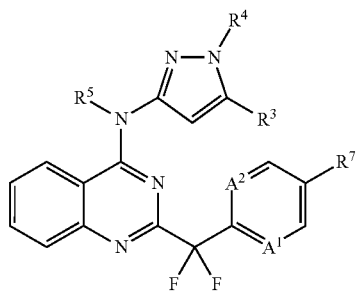

(XIIa)

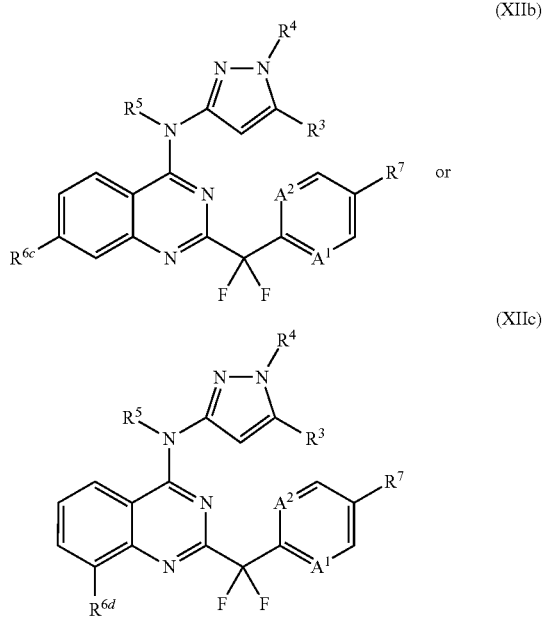

(XIIb)

(XIIc)

or a pharmaceutically acceptable salt thereof, wherein $A^1$ and $A^2$ are selected from N and CH, such that at least one of A or$^1$ $A^2$ is N;

$R^3$ is hydrogen or alkyl;

$R^{6c}$ is selected from deutero, halo, cyano, alkyl, haloalkyl, haloalkoxy and alkoxy; and $R^{6d}$ is selected from deutero, halo, cyano, alkyl, haloalkyl, haloalkoxy, alkoxy, alkylsulfonylamino, aminocarbonyl, heterocyclylaminocarbonyl, oxo-substituted heterocylyl, carboxyl, forinylamino and acetylamino.

17. The compound of claim 1 selected from:

(5-fluoropyridin-2-yl)(4-((5-methyl-1H-pyrazol-3-yl)amino)quinazolin-2-methathone;

2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-N-(5-methyl-1H-pyrazol-3-yl)quinazolin-4-amine;

2-(difluoro(5-fluoropyrimidin-2-yl)methyl)-N-(5-methyl-1H-pyrazol-3-yl)quinazolin-4-amine;

2-(difluoro(5-fluoropyridin-2-yl)methyl)-N-(1H-pyrazol-3-yl)quinazolin-4-amine;

N-(2-(difluoro(5-fluoropyridin-2-yl)methyl)quinazolin-methylthiazol-2-amine;

2-(difluoro(5-fluoropyridin-2-yl)methyl)-N-(1H-1,2,4-triazol-3-yl)quinazolin-4-amine;

2-(difluoro(5-fluoropyridin-2-yl)methyl)-N-(5-methoxy-1H-pyrazol-3-yl)quinazolin-4-amine;

2-(difluoro(5-fluoropyridin-2-yl)methyl)-7-methoxy-N-(5-methyl-1H-pyrazol-3-yl)quinazolin-4-amine;

7-bromo-2-(difluoro(5-fluoropyridin-2-ylmethyl)-N-(5-methyl-1H-pyrazol-3-yl)quinazolin-4-amine;

2-(difluoro(5-fluoropyridin-2-yl)methyl)-8-methyl-N-(5-methyl-1H-pyrazol-3-yl)quinazol-4-amine;

8-bromo-2-(difluoro(5-fluoropyridin-2-yl)methyl)-N-(5-methyl-1H-pyrazol-3-yl)quinazolin-4-amine;

2-(difluoro(5-fluoropyridin-2-yl)methyD-8-fluoro-N-(5-methy 1-1H-pyrazol-3-yl)quinazolin-4-amine;

7-cyclopropyl-2-(difluoro(5-fluoropyridin-2-yl)methyl)-N-(5-methyl-1H-pyrazol-3-yl)quinazolin-4-amine;

2-(difluoro(5-fluoropyridin-2-yl)methyl)-4-((5-methyl-1H-pyrazol-3-yl)amino)quinazoline-7-carbonitrite;

8-chloro-2-(difluoro(5-fluoropyridin-2-yl)methyl)-N-(5-methyl-1H-pyrazol-3-yl)quinazolin-4-amine;
2-(difluoro(5-fluoropyridin-2-yl)methyl)-7-methyl-N-(5-methyl-1H-pyrazol-3-yl)quinazolin-4-amine;
2-(difluoro(5-fluoropyridin-2-yl)methyl)-7-fluoro-N-(5-methyl-1H-pyrazol-3-yl)quinazolin-4-amine;
7-chloro-2-(difluoro(5-fluoropyridin-2-yl)methyl)-N-(5-methyl-1H-pyrazol-3-yl)quinazolin-4-amine;
2-(difluoro(5-fluoropyridin-2-yl)methyl)-N-(5-methyl-1H-pyrazol-3-yl)-8-(trifluoromethy)quinazolin-4-amine;
2-(difluoro(5-fluoropyridin-2-yl)methyl)-N-(5-methyl-1H-pyrazol-3-yl)-8-(trifluoromethoxy)quinazollin-4-amine;
2-(difluoro(5-fluoropyridin-2-yl)methyl)-4-((5-methyl-1H-pyrazol-3-yl)amino)quinazoline-8-carbonitrile;
2-(difluoro(5-fluoropyridin-2-yl)methyl-8-ethyl-N-(5-methyl-1H-pyrazol-3-yl)quinazolin-4-amine;
2-(difluoro(5-fluoropyridin-2-yl)methyl)-N-(5-methyl-1H-pyrazol-3-yl)-8-(methylsulfonyl)quinazolin-4-amine;
2-(difluoro(5-fluoropyridin-2-yl)methyl)-N-(5-methyl-1H-pyrazol-3-yl)-7-(methylsulthnyl)quinazolin-4-amine;
2-(difluoro(5-fluoropyridin-2-yl)methyl)-4-((5-methyl-1H-pyrazol-3-yl)amino)quinazoline-8-carboxamide;
8-chloro-2-(difluoro(5-fluoropyrimidin-2-yl)methyl)-N-(5-methyl-1H-pyrazol-3-yl)quinazolin-4-amine;
2-(difluoro(5-fluoropyridin-2-yl)methyl)-4-((5-methyl-1H-pyrazol-3-4)amino)quinazoline-7-carboxamide;
4-(2-(difluoro(5-fluoropyridin-2-yl)methyl)-4-((5-methyl-1H-pyrazol-3-yl)amino)quinazolin-8-yl)morpholin-3-one;
2-(difluoro(5-fluoropyridin-2-yl)methyl)-8-methoxy-N-(5-methyl)-1H-pyrazol-3-yl)quinazolin-4-amine;
N-(2-(difluoro(5-fluoropyridin-2-yl)methyl)-4-((5-methyl-1H-pyrazol-3-yl)amino)quinazolin-8-yl)formamide;
2-(difluoro(5-fluoropyridin-2-yl)methyl)-4-((5-methyl-1H-pyrazol-3-yl)amino)-N-(oxetan-3-yl)quinazoline-8-carboxamide;
2-(difluoro(5-fluoropyridin-2-yl)methyl)-4-((5-methyl-1H-pyrazol-3-yl)amino)quinazolin-8-ol;
methyl 2-(difluoro(5-fluoropyridin-2-yl)methyl)-4-((5-methyl-1H-pyrazol-3-yl)amino)quinazoline-8-carboxylate;
N-(2-difluoro(5-fluoropyridin-2-yl)methyl)-4-((5-methyl-1H-pyrazol-3-yl)amino)quinazolin-8-yl)acetamide;
2-(difluoro(5-fluoropyridin-2-yl)methyl)-N-(5-methyl-1H-pyrazol-3-yl)-8-nitroquinazolin-4-amine;
2-(difluoro(5-fluoropyridin-2-yl)methyl)-N4-(5-methyl-1H-pyrazol-3-yl)quinazoline-4,8-diamine;
8-cyclopropyl-2-(difluoro(5-fluoropyridin-2-yl)methyl)-N-(5-methyl-1H-pyrazol-3-yl)quinazolin-4-amine;
N-(2-(difluoro(5-fluoropyridin-2-yl)methyl)-4-((5-methyl-1H-pyrazol-3-yl)amino)quinazolin-8-yl)methanesulfonamide; and
2-(difluoro(5-fluoropyridin-2-yl)methyl)-4-((5-methyl-1H-pyrazol-3-yl)amino)quinazoline-8-carboxylic acid;
or a pharmaceutically acceptable salt thereof.

18. A pharmaceutical composition comprising a compound of claim 1 and a pharmaceutically acceptable carrier, diluent or excipient.

* * * * *